(12) United States Patent
Insana et al.

(10) Patent No.: US 11,294,052 B2
(45) Date of Patent: Apr. 5, 2022

(54) ULTRASONIC IMAGING WITH CLUTTER FILTERING FOR PERFUSION

(71) Applicant: The Board of Trustees of the University of Illinois, Urbana, IL (US)

(72) Inventors: Michael F. Insana, Urbana, IL (US); Minwoo Kim, Seattle, WA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 471 days.

(21) Appl. No.: 16/442,729

(22) Filed: Jun. 17, 2019

(65) Prior Publication Data
US 2019/0380684 A1    Dec. 19, 2019

Related U.S. Application Data

(60) Provisional application No. 62/686,232, filed on Jun. 18, 2018.

(51) Int. Cl.
*G06K 9/00* (2006.01)
*G01S 15/89* (2006.01)
(Continued)

(52) U.S. Cl.
CPC ............ *G01S 15/8981* (2013.01); *A61B 8/06* (2013.01); *A61B 8/488* (2013.01); *A61B 8/52* (2013.01);
(Continued)

(58) Field of Classification Search
None
See application file for complete search history.

(56) References Cited

U.S. PATENT DOCUMENTS 7,257,244 B2    8/2007  Miga
8,070,679 B2    12/2011 Ghaboussi et al.
(Continued)

FOREIGN PATENT DOCUMENTS

WO    2010078520    7/2010
WO    2015063721    5/2015

OTHER PUBLICATIONS

L. A. F. Ledoux, P. J. Brands, and A. P. G. Hoeks, "Reduction of the clutter component in Doppler ultrasound signals based on singular value decomposition: A simulation study," Ultrasonic Imaging, vol. 19, No. 1, pp. 1-18, 1997.
(Continued)

*Primary Examiner* — Randolph I Chu
(74) *Attorney, Agent, or Firm* — FisherBroyles LLP; Anthony J DoVale

(57) ABSTRACT

Described herein are methods and apparatus for increasing sensitivity of ultrasound imaging of fluid flow in an object of interest. Ultrasound imaging of blood perfusion can be performed without contrast enhancement. Embodiments include transforming a spatiotemporal echo data array into a three-dimensional perfusion data array having a spatial dimension, a slow-time dimension, and a frame-time dimension, and filtering the perfusion data array with an eigen passband clutter filter. The clutter filter can increase sensitivity and utility of ultrasound imaging of fluid flow. In some aspects, the method can yield blood flow signal power and perfusion values well separated from tissue clutter. In an example, enhancements to ischemic tissue perfusion maps in a murine model are shown.

29 Claims, 35 Drawing Sheets
(30 of 35 Drawing Sheet(s) Filed in Color)

(51) Int. Cl.
  *A61B 8/08* (2006.01)
  *A61B 8/06* (2006.01)
  *G06T 5/00* (2006.01)
(52) U.S. Cl.
  CPC .... *G06T 5/002* (2013.01); *G06T 2207/20182* (2013.01)

(56) References Cited

U.S. PATENT DOCUMENTS

| | | | |
|---|---|---|---|
| 2017/0281094 | A1 | 10/2017 | Ghaboussi et al. |
| 2018/0103912 | A1 | 4/2018 | Canfield et al. |
| 2019/0029651 | A1* | 1/2019 | Patil .................. A61B 8/485 |
| 2021/0267577 | A1* | 9/2021 | Trzasko ............... A61B 8/5207 |

OTHER PUBLICATIONS

F. W. Mauldin, D. Lin, and J. A. Hossack, "The singular value filter: A general filter design strategy for PCA-based signal separation in medical ultrasound imaging," IEEE Transactions on Medical Imaging, vol. 30, No. 11, pp. 1951-1964, 2011.

C. Demen'e, T. Deffieux, M. Pernot, B. F. Osmanski, V. Biran, J. L. Gennisson, L.-A. Sieu, A. Bergel, S. Franqui, J. M. Correas, I. Cohen, O. Baud, and M. Tanter, "Spatiotemporal clutter filtering of ultrafast ultrasound data highly increases Doppler and fUltrasound sensitivity," IEEE Trans Med Imag, vol. 34, No. 11, pp. 2271-2285, 2015.

V. Cantisani, M. Bertolotto, H. Weskott, L. Romanini, H. Grazhdani, M. Passamonti, F. Drudi, F. Malpassini, A. Isidori, F. Meloni, F. Calliada, and F. D'Ambrosio, "Growing indications for CEUS: The kidney, testis, lymph nodes, thyroid, prostate, and small bowel," European Journal of Radiology, vol. 84, No. 9, p. 1675 1684, 2015.

W. Yang and P. Dempsey, "Diagnostic breast ultrasound: current status and future directions," Radiol Clin North Am, vol. 45, No. 5, pp. 845-861, 2007.

N. Oebisu, M. Hoshi, M. Ieguchi, J. Takada, T. Iwai, M. Ohsawa, and H. Nakamura, "Contrast-enhanced color Doppler ultrasonography increases diagnostic accuracy for soft tissue tumors," Oncol Rep, vol. 32, No. 4, pp. 1654-1660, 2014.

S. Bjærum, H. Torp, and K. Kristoffersen, "Clutter filter design for ultrasound color flow imaging," IEEE Trans Ultrason Ferroelectr Freq Control, vol. 49, No. 2, pp. 204-216, 2002.

L. Løvstakken, S. Bjærum, K. Kristoffersen, R. Haaverstad, and H. Torp, "Real-time adaptive clutter rejection filtering in color flow imaging using power method iterations,".

A. Yu and L. Løvstakken, "Eigen-based clutter filter design for ultrasound color flow imaging: a review," IEEE Trans Ultrason Ferroelectr Freq Control, vol. 57, No. 5, pp. 1096-1111, 2010.

L. D. Lathauwer, B. D. Moor, and J. Vandewalle, "A multilinear singular value decomposition," SIAM Journal on Matrix Analysis and Applications, vol. 21, No. 4, pp. 1253-1278, 2000.

G. Bergqvist and E. Larsson, "The higher-order singular value decomposition: Theory and an application [lecture notes]," IEEE Signal Processing Magazine, vol. 27, No. 3, pp. 151-154, 2010.

S. Bjærum, H. Torp, and K. Kristoffersen, "Clutter filters adapted to tissue motion in ultrasound color flow imaging," IEEE Trans Ultrason Ferroelectr Freq Control, vol. 49, No. 6, pp. 693-704, 2002.

Z.-P. Liang, "Spatiotemporal imaging with partially separable functions," in Proc. IEEE Int Symp Biomed Imaging. IEEE, 2007, pp. 988-991.

D. Muti and S. Bourennane, "Multidimensional filtering based on a tensor approach," Signal Processing, vol. 85, No. 12, pp. 2238-2353, 2005.

L. D. Lathauwer, B. D. Moor, and J. Vandewalle, "On the best rank-1 and rank-(r1, r2,:, m) approximation of higher-order tensors," SIAM Journal on Matrix Analysis and Applications, vol. 21, No. 4, pp. 1324-1342, 2000.

N. Vannieuwenhoven, R. Vandebril, and K. Meerbergen, "A new truncation strategy for the higher-order singular value decomposition," SIAM Journal on Scientific Computing, vol. 34, No. 2, pp. A1027-A1052, 2012.

J. Hua, L. Dobrucki, M. Sadeghi, J. Zhang, B. Bourke, P. Cavaliere, J. Song, and et al., "Noninvasive imaging of angiogenesis with a 99mTc-labeled peptide targeted at _v_3 integrin after murine hindlimb ischemia," Circulation, vol. 111, No. 6, pp. 3255-3260, 2005.

D. Bertoldi, P. L. de Sousa, Y. Fromes, C. Wary, and P. Carlier, "Quantitative, dynamic and noninvasive determination of skeletal muscle perfusion in mouse leg by NMR arterial spin-labeled imaging," Magn Reson Imaging, vol. 26, No. 9, pp. 1259-1265, 2008.

Michael Insana, MinWoo Kim, Craig K. Abbey; Efficiency of U.S. Tissue Perfusion Estimators; IEEE Transactions on Ultrasonics, Ferroelectrics, and Frequency Control (vol. 63, Issue: 8, Aug. 2016).

CH. Kargel, G. Hoebenreich, G. Plevnik, B. Trummer, M.F. Insana Velocity Estimation and Adaptive Clutter Filtering for Color Flow Imaging Univ. of CA Davis; Graz Univ. of Technology, Graz, Austria, 2002.

Pengfei Song ; Armando Manduca ; Joshua D. Trzasko ; Shigao Chen Ultrasound Small Vessel Imaging With Block-Wise Adaptive Local Clutter Filtering IEEE Transactions on Medical Imaging (vol. 36, Issue: 1, Jan. 2017).

Zhiyuan Shen ; Naizhang Feng Clutter Rejection methods in Doppler color flow imaging: Single-ensemble vs. multi-ensemble Engineering in Medicine and Biology Society (EMBC), 2015 37th Annual Int'l Conf. of the IEEE, Aug. 25-29, 2015.

Adrian J. Y. Chee ; Billy Y. S. Yiu ; Alfred C. H. Yu A GPU-Parallelized Eigen-Based Clutter Filter Framework for Ultrasound Color Flow Imaging IEEE Transactions on Ultrasonics, Ferroelectrics, and Frequency Control (vol. 64, Issue: 1, Jan. 2017).

Siyuan Wei, et al. Low-Cost 3-D Flow Estimation of Blood with Clutter IEEE Transactions on Ultrasonics, Ferroelectrics, and Frequency Control (vol. 64, Issue: 5, May 2017).

Zoetermeer; Seeing the Unseen, New Techniques in Vascular Imaging: Superb Micro-Vascular Imaging. Medical Review Toshiba Medical Systems Corporation 2014.

Ghaboussi, et al. Computers and Geotechnics, vol. 22, No. 1, pp. 29-52, 1998.

Ghaboussi, et al. Int. J. Numer. Meth. Engng. 42, 105-126 (1998).

Hashash et al. Int. J. Numer. Meth. Engng 2004; 59:989-1005 (DOI: 10.1002/nme.905).

The Journal of the Acoustical Society of America; Published Online: Jun. 9, 2017; https://asa.scitation.org/doi/abs/10.1121/1.4987976.

Hoerig et al. An information-based machine learning approach to elasticity imaging; Biomech Model Mechanobiol (2017) 16:805-822.

Hoerig et al. Data-Driven Elasticity Imaging Using Cartesian Neural Network Constitutive Models and the Autoprogressive Method; IEEE Transactions on Medical Imaging, vol. 38, No. 5, May 2019.

Tyagi et al. Algorithms for quantitative quasi-static elasticity imaging using force data; Int. J. Numer. Meth. Biomed. Engng. 2014; 30:1421-1436.

H. Niiyama, N. Huang, M. Rollins, and J. Cooke, "Murine model of hindlimb ischemia," Journal of Visualized Experiments, vol. 23, No. e1035, 2009.

Alfred C.H. Yu Eigen-based clutter filter design for ultrasound color flow imaging: a review IEEE Transactions on Ultrasonics, Ferroelectrics, and Frequency Control (vol. 57, Issue: 5, May 2010).

Charlie Demené et al. Spatiotemporal Clutter Filtering of Ultrafast Ultrasound Data Highly Increases Doppler and Ultrasound Sensitivity IEEE Transactions on Medical Imaging (vol. 34, Issue: 11, Nov. 2015).

* cited by examiner (a) Source power in each eigen-mode (b) Eigen-images and similarity function (c) Mean correlation coefficient $q[k]$ (d) Rigid-motion corruption coefficient $r_{i_3}$

ULTRASONIC IMAGING WITH CLUTTER FILTERING FOR PERFUSION

BACKGROUND

Ultrasonic imaging with beamformed echo data has become a conventional medical tool. Drawbacks of using beamformed echo data include low signal-to-noise ratio, as well as clutter effects. Clutter artifacts overlay an image of interest, which causes loss of contrast and obscures the image of interest. Clutter artifacts also result in false image components and can be more intense than the image of interest. Clutter artifacts limit the use of ultrasonic imaging for measuring anatomical features, especially for slow movement of tissues and fluids, as well as observing the depth of the features of interest. Because of these drawbacks, among others, some anatomical features may be entirely invisible to ultrasonic imaging methods.

Beamformed echo data for ultrasonic imaging can be filtered to improve image quality. However, filtering is generally ineffective for many anatomical features, including slow movement of tissues and fluids. For example, imaging of ischemia is often intractable in conventional ultrasonic imaging, such as power doppler methods. Regions of slow blood perfusion are poorly characterized. Quantification of slow and weakly-scattering intrinsic perfusion signals cannot be robustly accomplished.

Conventional filtering of echo data under conditions of slow flow may fail because a significant portion of the perfusion signal may fall into the attenuated frequency channels of the clutter filter.

Contrast enhancement has been used to increase signal-to-noise and contrast in imaging methods. However, contrast agents have severe drawbacks including potential tissue or cell damage, toxicity, and lack of means for their delivery to anatomical sites of interest.

What is needed are methods and apparatus for ultrasonic imaging that can reduce the effects of clutter by suppressing clutter image components. It is also desirable to increase the signal-to-noise ratio to improve ultrasonic image quality.

There is an urgent need for methods and devices to measure and display the magnitude of blood perfusion in tissue at each point in a scan plane. What is needed are methods and apparatus for ultrasonic imaging that can detect and quantify slow blood perfusion.

There has long been a need to achieve these goals without the use of contrast agents.

BRIEF SUMMARY

This invention can provide methods and apparatus for increasing sensitivity of ultrasound imaging of fluid flow in an object of interest. The ultrasonic imaging of blood perfusion can advantageously be performed without the use of contrast agents. Embodiments of this invention include steps for clutter filtering, including transforming a spatiotemporal echo data array into a three-dimensional perfusion data array having a spatial dimension, a slow-time dimension, and a frame-time dimension, and filtering the perfusion data array with an eigen passband clutter filter. The clutter filter can increase sensitivity and utility of ultrasound imaging of fluid flow. In some aspects, the method can yield blood flow signal power and perfusion values well separated from tissue clutter. In an example, enhancements to ischemic tissue perfusion maps in a murine model are shown.

Embodiments of this invention may include methods for imaging flow of a fluid in an object of interest, the method comprising: acquiring beamformed ultrasound echo data from the object of interest comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension; re-ordering the spatiotemporal data array into a three-dimensional perfusion data array having one combined spatial dimension, one slow-time dimension, and one frame-time dimension, wherein the axial and lateral dimensions are combined into the one combined spatial dimension; filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array. The fluid can be blood and the method may be performed without the use of a contrast agent. The echo data can be acquired upon transmitting a focused ultrasound beam into the object of interest.

In some embodiments, filtering the perfusion data array with an eigen passband clutter filter may comprise the steps: unfolding the perfusion data array into three empirical correlation matrices based on slow-time signals, spatial signals, and frame-time signals; calculating eigenvectors for each of the three empirical correlation matrices of the perfusion data array, wherein the eigenvectors are columns of a core tensor; and selecting a subspace within the core tensor that contains signals from the slowly moving and/or spatially disorganized fluid in the object of interest and zeroing the rest of the core tensor.

In further embodiments, the clutter filter can partition an echo data subspace of spatially coherent tissue movements from an echo data subspace of spatially incoherent fluid perfusion. In certain embodiments, the filtering can enhance the sensitivity of imaging perfusion of the fluid within the object of interest by identifying a subspace in the perfusion array data that isolates perfusion signals and by projecting the echo data onto the subspace before computing the image of the object of interest.

Aspects of this invention may further include selecting a subspace within the core tensor that contains signals from the slowly moving and/or spatially disorganized fluid in the object of interest comprises visually selecting an eigenvector passband according to the steps: a) eliminating one or more initial spatial eigenvectors having a uniform spatial signal spectrum, which are dominated by clutter; b) selecting a passband range of slow-time signal eigenvectors, wherein the passband range begins after initial eigenvectors having non-zero signals only at zero frequency, and wherein the passband range ends before a linear slow-time spectral pattern appears in a spectral region of the slow-time eigenvectors of a comparative control sample; c) selecting a passband range of frame-time signal eigenvectors, wherein the passband range spans an asymmetric linear frame-time spectral pattern in the object of interest.

In certain aspects, selecting a subspace within the core tensor that contains signals from the slowly moving and/or spatially disorganized fluid in the object of interest may comprise using a classifier which identifies and eliminates core elements of the core tensor that are predominantly from a clutter source based on energy and similarity features according to the following steps performed on comparative training data similar to the echo data of the object of interest: a) calculating normalized eigenvalue energy of the slow-time, spatial, and frame-time dimensions and discarding a high eigenvalue energy region; b) calculating a Pearson's correlation coefficient to quantify similarity of spatial images from spatial eigenvectors of the slow-time dimension and discarding a high similarity region; c) calculating a coherent motion corruption scalar factor from the frame-time dimension echo power images and discarding a corrupt region; d) classifying and eliminating core elements above a classifier threshold as being clutter dominated, wherein the classifier threshold is calculated from a combination of steps a), b), and c) using the comparative training data.

In additional aspects, selecting a subspace within the core tensor that contains signals from the slowly moving and/or spatially disorganized fluid in the object of interest may comprise visually selecting core tensor eigenimages of the perfusion data array according to the steps: a) averaging slow-time spatial eigenimages 3-5 and discarding others; b) retaining a series of fluid flow spatial eigenimages which appear visibly dark and appear after initial eigenimages that are bright, and discarding noise eigenimages beyond the fluid flow spatial eigenimages; and c) discarding the first two frame-time eigenimages and discarding frame-time eigenimages having the appearance of aliasing.

In some embodiments, a step of noise filtering after clutter filtering may be performed, wherein noise filtering may be done by discarding noise dominated subspace of the core tensor.

In further embodiments, echo data can be acquired by Doppler mode, the imaging may be color-flow or power-Doppler imaging, and the frame-time dimension can be sampled at a rate about 100 to 1,000 times slower than the slow-time dimension. Echo data may be acquired over a period up to about 10 seconds, or up to about 30 seconds, or longer. Echo data may be obtained from transducer ultrasound pulses having from 3 to 32 MHz center frequency. The ultrasound pulses may have at least 5 mm tissue penetration.

In some aspects, forming an image of the object of interest can comprise the steps: calculating the signal power of the subspace of spatially incoherent fluid perfusion; and mapping the signal power into the image of the object of interest.

In certain embodiments, fluid velocity discrimination may be performed, wherein fluid velocity can be calculated from a post-filtered slow-time echo signal.

The object of interest may be a tissue, a blood vessel, a microvascular structure, a vascular network, an organ, an appendage, or a tumor. The imaging may show peripheral muscle blood perfusion to assess microvascular damage from ischemia or chronic metabolic disorders.

Embodiments of this invention can further provide an apparatus for ultrasound imaging, comprising: an ultrasound probe for transmitting ultrasound pulses and receiving ultrasound echo signals and transferring ultrasound echo signals to a processor; a processor for carrying out the steps: acquiring beamformed ultrasound echo data from the ultrasound probe, the data comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension; re-ordering the spatiotemporal data array into a three-dimensional perfusion data array having one combined spatial dimension, one slow-time dimension, and one frame-time dimension, wherein the axial and lateral dimensions are combined into the one combined spatial dimension; filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array; and a display for displaying the ultrasound image.

An apparatus of this invention can perform filtering of the perfusion data array with an eigen passband clutter filter which may comprise the steps: unfolding the perfusion data array into three empirical correlation matrices based on slow-time signals, spatial signals, and frame-time signals; calculating eigenvectors for each of the three empirical correlation matrices of the perfusion data array, wherein the eigenvectors are columns of a core tensor; and selecting a subspace within the core tensor that contains signals from the slowly moving and/or spatially disorganized fluid in the object of interest and zeroing the rest of the core tensor.

An apparatus of this invention can select a subspace within the core tensor that contains signals from the slowly moving and/or spatially disorganized fluid in the object of interest by using a classifier which identifies and eliminates core elements of the core tensor that are predominantly from a clutter source based on energy and similarity features according to the following steps performed using comparative training data similar to the echo data from object of interest: a) calculating normalized eigenvalue energy of the slow-time, spatial, and frame-time dimensions and discarding a high eigenvalue energy region; b) calculating a Pearson's correlation coefficient to quantify similarity of spatial images from spatial eigenvectors of the slow-time dimension and discarding a high similarity region; c) calculating a coherent motion corruption scalar factor from the frame-time dimension echo power images and discarding a corrupt region; d) classifying and eliminating core elements above a classifier threshold as being clutter dominated, wherein the classifier threshold is calculated from a combination of steps a), b), and c) using the comparative training data. The apparatus may further comprise the processor executing noise filtering after clutter filtering, wherein noise filtering is performed by discarding noise dominated subspace of the core tensor.

In additional embodiments, this invention provides a non-transitory machine-readable storage medium having stored therein instructions for execution by a processor which cause the processor to perform the steps of a method for imaging an object of interest containing a fluid, the method comprising: acquiring beamformed ultrasound echo data comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension; re-ordering the spatiotemporal data array into a three-dimensional perfusion data array having one combined spatial dimension, one slow-time dimension, and one frame-time dimension, wherein the axial and lateral dimensions are combined into the one combined spatial dimension; filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array.

A storage medium of this disclosure can perform filtering the perfusion data array with an eigen passband clutter filter by the steps: unfolding the perfusion data array into three empirical correlation matrices based on slow-time signals, spatial signals, and frame-time signals; calculating eigenvectors for each of the three empirical correlation matrices of the perfusion data array, wherein the eigenvectors are columns of a core tensor; and selecting a subspace within the core tensor that contains signals from the slowly moving and/or spatially disorganized fluid in the object of interest and zeroing the rest of the core tensor.

A storage medium of this disclosure can perform selecting a subspace within the core tensor that contains signals from the slowly moving and/or spatially disorganized fluid in the object of interest by using a classifier which identifies and eliminates core elements of the core tensor that are predominantly from a clutter source based on energy and similarity features according to the following steps performed on comparative training data similar to the object of interest: a) calculating normalized eigenvalue energy of the slow-time, spatial, and frame-time dimensions and discarding a high eigenvalue energy region; b) calculating a Pearson's correlation coefficient to quantify similarity of spatial images from spatial eigenvectors of the slow-time dimension and discarding a high similarity region; c) calculating a coherent motion corruption scalar factor from the frame-time dimension echo power images and discarding a corrupt region; d) classifying and eliminating core elements above a classifier threshold as being clutter dominated, wherein the classifier threshold is calculated from a combination of steps a), b), and c) using the comparative training data.

BRIEF DESCRIPTION OF THE DRAWINGS

This patent or application file contains at least one drawing executed in color. Copies of this patent or patent application publication with color drawings will be provided by the US Patent Office upon request and payment of the necessary fee.

DETAILED DESCRIPTION

Figure 1:
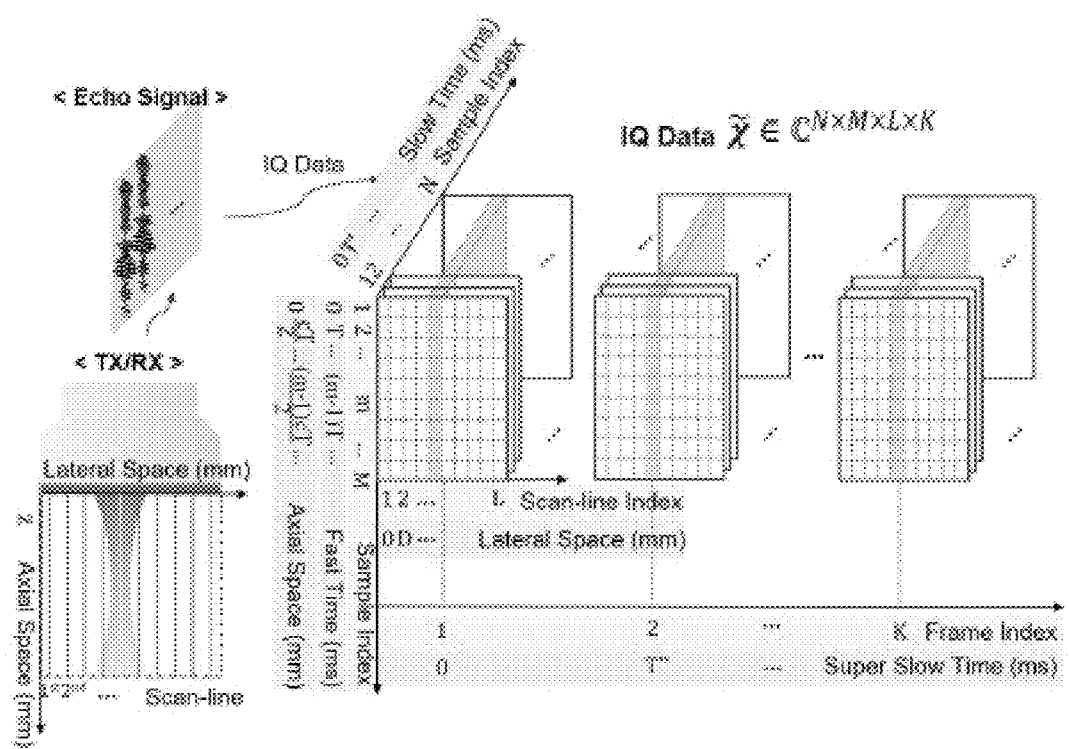
FIG. 1: Illustration of an embodiment of data acquisition for imaging. One quadrature IQ echo vector is recorded for each pulse transmission. The fast-time sampling interval is T, generating an M×1 vector. N echo vectors are recorded with interval T' at each line of site. Repeating the acquisition process over L lateral lines of site with spatial interval D makes one Doppler frame array. Recording K frames at time interval T" results in the 4-D array of IQ echo data $X \in \mathbb{C}^{N \times M \times L \times K}$. The array is reformed as a 3rd-order tensor $X \in \mathbb{C}^{N \times S \times K}$ where S=ML.

This invention can provide methods for increasing the sensitivity of ultrasound power-Doppler imaging without the use of contrast enhancement or contrast agents.

In some aspects, this invention can provide an eigenfilter, which preserves all three dimensions of a transformed echo data array and yields power estimates for blood flow and perfusion that are well separated from tissue clutter.

Methods disclosed herein can be applied at high frequency, for example, with 24 MHz center frequency pulses.

Surprising enhancements to tissue perfusion maps in normal and ischemic tissues are found in a murine model of an ischemic hindlimb.

In certain aspects, the methods of this invention can be used with any ultrasonic beamformed RF echo data.

This invention provides extended-dimension singular-value decomposition filters for 3D data arrays. The filtering facilitates isolation of echo power from slowly-moving and spatially disorganized fluid movement in an object of interest, for example red blood cell (RBC) movement in tissue.

In some embodiments, filter construction yields one set of basis vectors for each of the three data dimensions within a region of interest. Retaining all three data dimensions can enable the adaptive filter to effectively separately signal components. By analyzing data along the frame-time axis, the sensitivity of ultrasound imaging to blood perfusion echo signals can be surprisingly enhanced.

A subspace in a transformed data core array that isolates perfusing blood signals can be found and utilized. Projecting the recorded echo data onto that subspace before computing the signal power at each pixel can dramatically increase ultrasound sensitivity to perfusion.

The process of filter formation can include signal averaging that improves filter stability. Spatial regions can be selected that include only wide-sense stationary echo data.

In some aspects, this invention provides echo-acquisition and data filtering that surprisingly improves signal-to-noise-plus-clutter-ratio (SNCR) and Doppler-frequency resolution in ultrasonic imaging.

The filtering can be tuned to show regions of slower perfusion that are not visible using conventional ultrasound techniques. The acquired data at each spatial location may be arranged to have two temporal dimensions: a slow-time sampled dimension on the order of kHz and a frame time sampled dimension on the order of Hz. Temporal sampling may be adjusted to increase the density of independent samples in the low-frequency Doppler spectrum where the weak perfusion signal may be strongest. The dimension of the clutter filter can be increased to fully exploit the expanded dimensionality of the data.

In certain embodiments, high-frequency pulses can be used to further increase SNCR.

The recorded data array initially may have two spatial dimensions (axial and lateral) and two temporal dimensions (slow-time and frame-time). These data can be re-ordered to combine the two spatial axes into one, resulting in a 3D data array with one spatial and two temporal axes. Information contained within this 3D data array can be filtered with a 3D clutter filter that separates blood components from clutter and noise.

This invention can expand the filter dimension to use information from both space and time to isolate the blood signal. Filtering exploits the spatial coherence of clutter echoes as distinct from the more incoherent flow patterns of perfusion when separating clutter and blood signals. Data can be filtered along spatial and temporal axes, including frame-time data.

In some embodiments, the methods of this invention may be applied to muscle-perfusion imaging of healthy and ischemic mouse hindlimbs. Perfusion in this model of surgically-induced ischemia can generate spatial patterns of perfusion/ischemia.

In further aspects, this invention can extend SVD filters to 3D data arrays using a higher-order SVD methodology (HOSVD). The methods of this invention can provide surprisingly increased SNCR and Doppler frequency resolution in ultrasound imaging, especially for perfusion, based on novel echo acquisition and data filtering strategies described herein. Embodiments of this disclosure include tuning the filtering process to identify regions of slower perfusion, which are not visible using conventional methods of ultrasound imaging.

In some embodiments, methods and apparatus of this disclosure can be used to adjust temporal sampling during data acquisition to increase the density of independent samples in the low-frequency Doppler spectrum where the weak perfusion signal may be the strongest.

In additional aspects, this invention can increase the dimension of the clutter filter to fully exploit the expanded dimensionality of the acquired data, by finding a subspace in an HOSVD filter core array that isolates perfusion signals.

Methods and apparatus described herein can employ high frequency pulses to further increase SNCR.

Embodiments of this invention provide steps for filtering echo data arrays to provide improved methods and apparatus for ultrasound imaging. Improvements can be obtained in part by consolidating two spatial axes into one spatial axis, resulting in a 3D data array. The initially recorded data array can have two spatial (axial and lateral) and two temporal (slow-time and frame-time) dimensions. Improvements in ultrasound imaging can also be obtained by analyzing the consolidated 3D data array against a novel 3D clutter filter to separate the blood components from clutter and noise, thereby allowing weak perfusion signals to be observed with greater ease.

Methods and apparatus of this invention can enable the user to generate 3D spatiotemporal data arrays to detect slow blood flow using ultrasonic imaging with surprisingly advantageous signal to noise.

In certain aspects, pulse transmission can be a focused beam. Focused transmission can provide peripheral perfusion imaging with improved data quality and advantageously superior perfusion estimates.

In some embodiments, a transmitted ultrasound beam of this disclosure can be focused. A beam can be focused mechanically by use of a lens, for example, or electronically by use of transmission delays in a transducer array. A focused beam may have a fixed focal depth or may have a modulated focal depth. In certain embodiments, a transmitted ultrasound beam of this disclosure can be dynamically focused. A transducer array can be linear, planar, or annular, and may have the capability for focusing and/or steering an ultrasound beam.

In further aspects, methods and apparatus of this invention can employ a spatial region data window that can be modulated for a clutter filter. In some embodiments, a data window can be reduced for regions in the object of interest where flow is spatially variable. For objects of interest with broad regions of uniform flow, a spatial window can be enlarged, which reduces computational time.

In further embodiments, the ultrasonic imaging of slow blood flow can be done entirely without the use of contrast agents.

In additional embodiments, methods for acquisition and filtering can greatly increase the sensitivity of ultrasonic power-Doppler perfusion imaging without contrast enhancement. The filtering can allow separation fast and slow flows as indicated with blue and red color maps in FIG. 10 (arrows in top row of FIG. 11 also indicate arterial flows). A portion of the femoral artery in the ischemic image was captured. This ligated vessel appears prominently in the perfusion image because it can be weakly fed from collateral vessels. Also, at 24 MHz, the ischemic hindlimb perfusion image inset in FIG. 10(E) clearly displays vessels with diameter smaller than 200 µm. These small vessels are less visible in the control hindlimb FIG. 10 (F) where surrounding capillary perfusion reduces small-vessel contrast.

In general, baseline perfusion, which is 17 ml/min/100 g in the normal hindlimb, falls to 60-70% of that value following femoral ligation. Consequently, a 5-10 g hindlimb muscle has normal capillary flow in the range of 1-3 ml/min.

Embodiments of this invention can provide successful filtering by selection of clutter and blood subspaces within a core tensor, G. In some embodiments, the selection method can be based on eigenvalue information and echogenic properties of the sources. By separating the prominent elements in G, filter ranges can be determined which surprisingly and advantageously improve resulting PD images. In some methods, eigenvector information can be utilized to guide an objective and automated partitioning of G.

Figure 10:
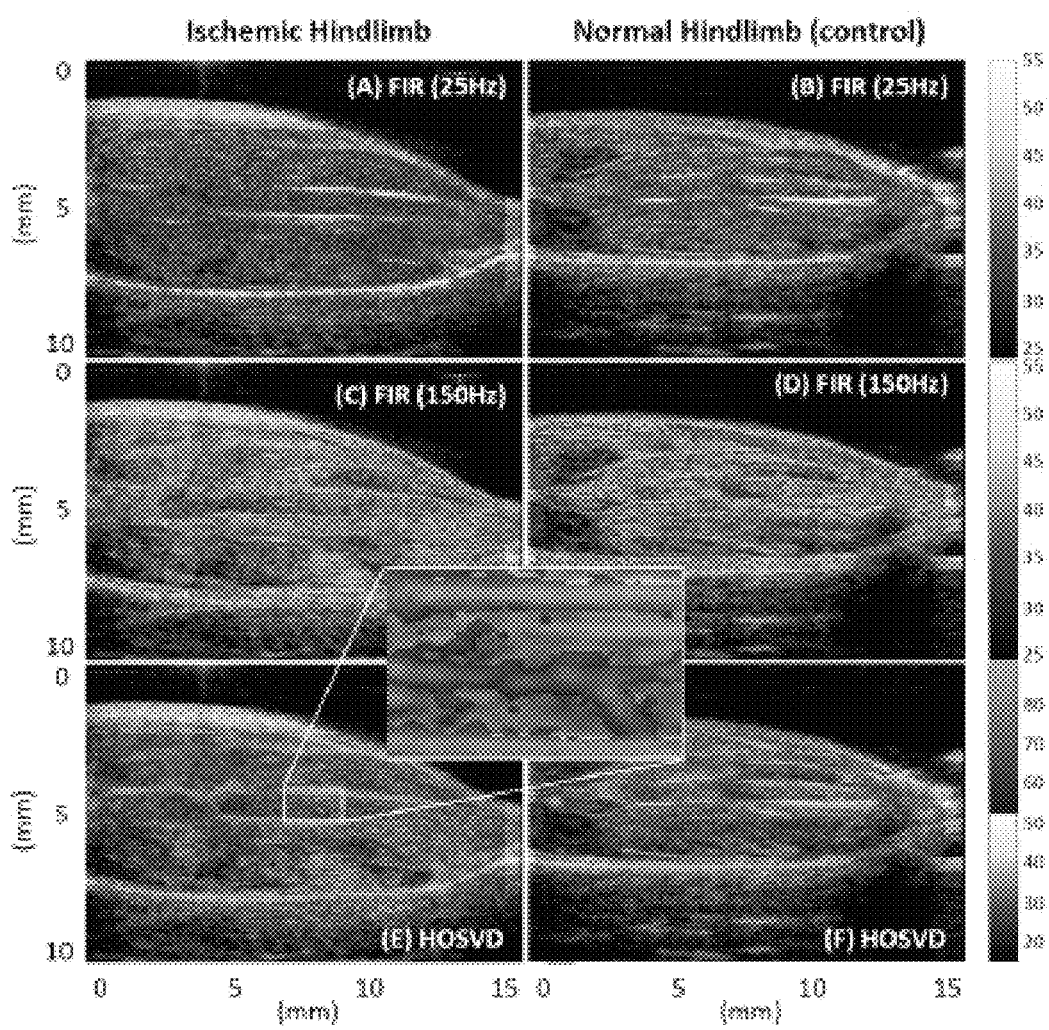
FIG. 10. PD images are compared using standard FIR clutter filtering (first row: 25 Hz high-pass, second row: 150 Hz high-pass) and adaptive HOSVD filtering (third row) applied to the same data array. Notice that perfusion in the control limb is fairly uniform, except in distal regions where the SNCR is low. Conversely, the ischemic limb shows patchy perfusion throughout. The inset shows an enlargement of microvessels. Given that the PD pixel dimensions are 32 µm axially and 60 µm laterally, we are resolving 160 µm-dia vessels axially and 300 µm-dia vessels laterally. Axial resolution for 24 MHz pulses with 12 MHz bandwidth is ~128 µm. The blue and red colorbars indicate, respectively, color maps related to slow-time power (dB) and frame-time power (dB).
Figure 11:
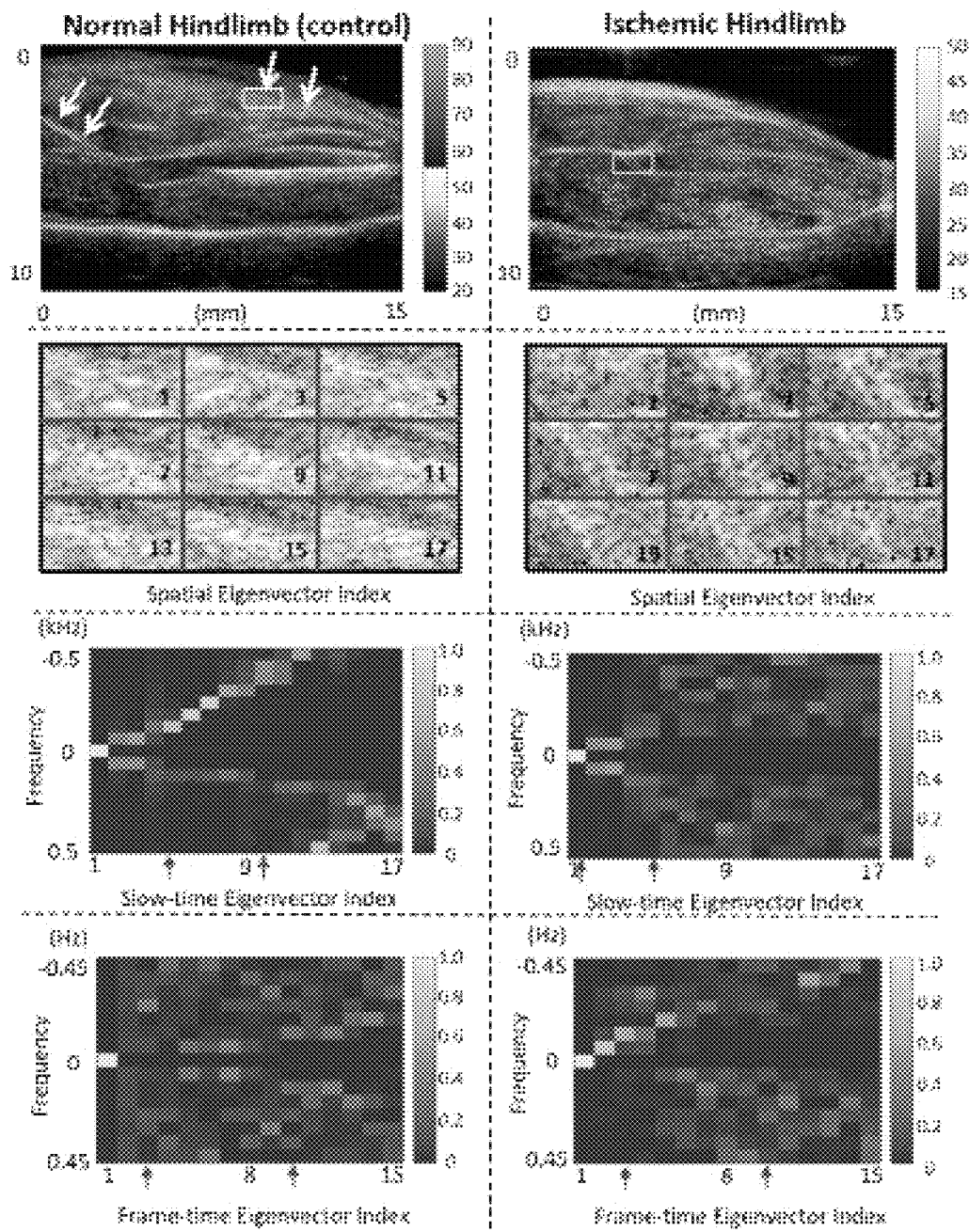
FIG. 11. The two columns illustrate analyses of data within local regions of three images. Top row shows adaptive HOSVD images of normal and ischemic hindlimbs. White arrows indicate arterial flows, and boxes indicate analysis regions that include a vessel. The second row shows 9 of the first 18 spatial eigenvectors, some showing linear shapes similar to vessels seen in top row images. Third and fourth rows depict the power spectrum of slow-time and frame-time eigenvectors, respectively. The vertical axis is temporal frequency with the origin at the center, and the horizontal axis indicates eigenvectors along the corresponding axes, of which there are 17. Each column of the four spectral images is the absolute-square Fourier transform of the corresponding eigenvector. Eigenvectors between the red arrows were passed by the HOSVD filter for the images displayed in this report. Eigenvectors outside these ranges were removed by the filter.
Figure 12:
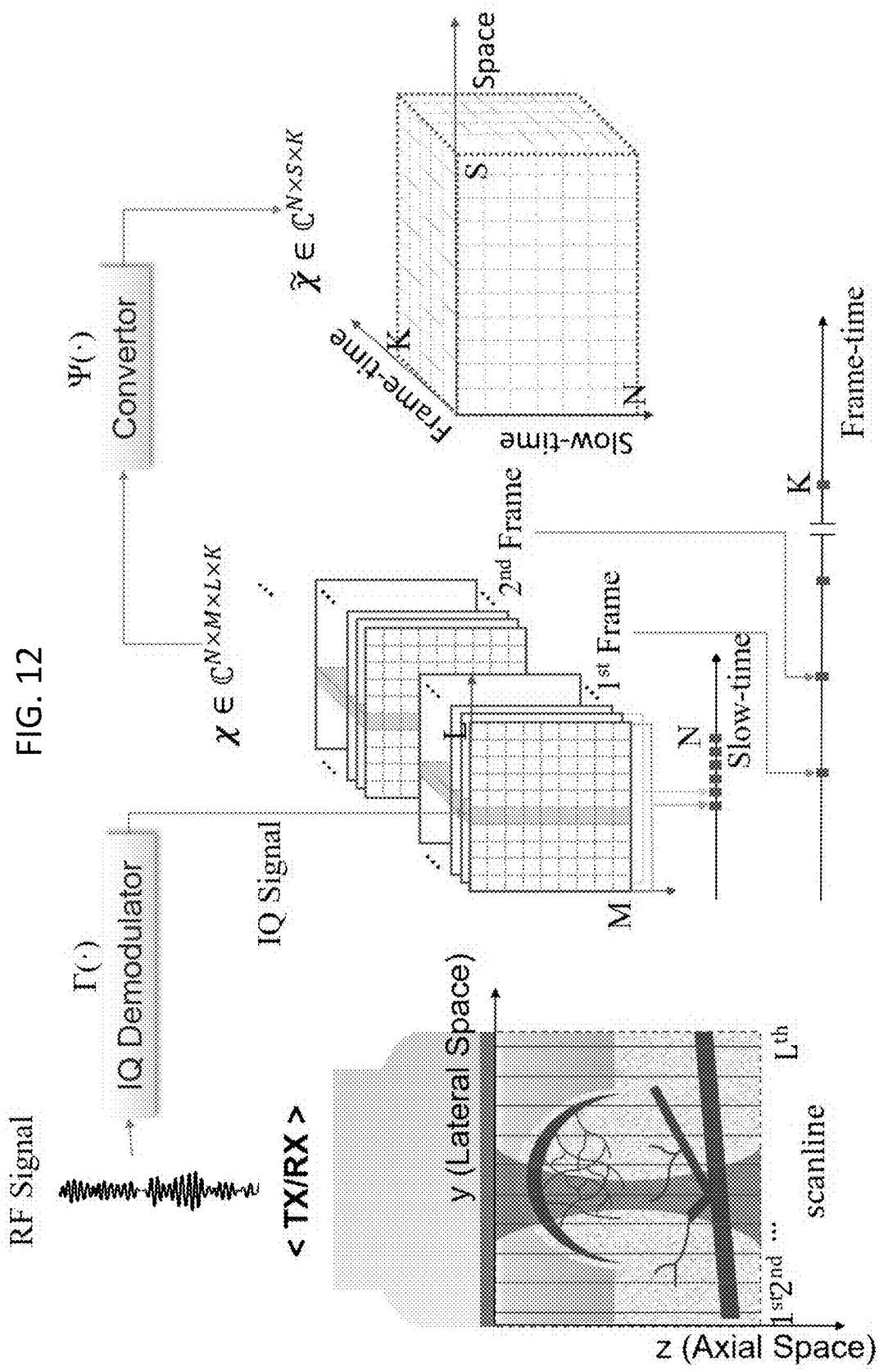
FIG. 12. Color-flow acquisition is illustrated resulting in multidimensional data array $\mathcal{X}$. A linear array transmits sound pulses into tissue and receives echoes along a line of site. Signals from the receive aperture are beamformed, fast-time sampled, decomposed into baseband quadrature signals and stored as an M-point complex IQ vector. N transmissions in slow time at a ~1 kHz pulse repetition frequency were made for each of L lateral lines to compose one 3D Doppler frame. Recording K frames at a 10-Hz frame repetition frequency yields the 4D data array $\mathcal{X} \in \mathbb{C}^{N \times M \times L \times K}$. The 4-D array is re-ordered to form 3D array $\mathcal{X}' \in \mathbb{C}^{N \times S \times K}$, where S=ML.
Figure 13:
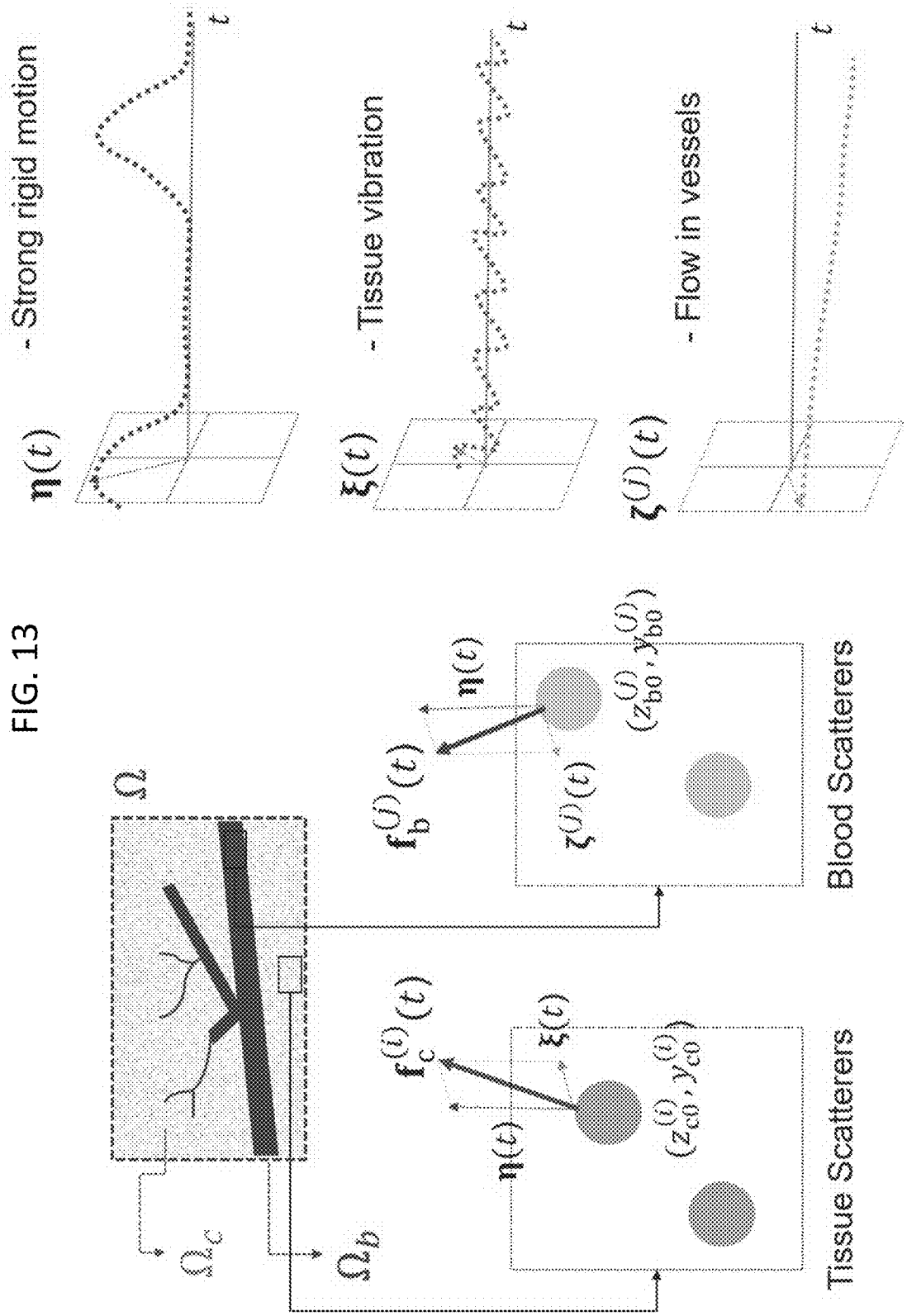
FIG. 13. Simulation of tissue perfusion is illustrated. Scattering field $\Omega$ consists of nonoverlapping regions of tissue scatterers in $\Omega_c$ and moving RBCs in $\Omega_b$. A time series (top right) for the entire field $\Omega$ in which all scatterers (bottom left) undergo large-scale low-frequency periodic rigid motion mimicking respiration. In addition, scatterers in regions $\Omega_c$ undergo rigid-body vibration at higher frequency and smaller amplitude, while vascular RBCs in regions $\Omega_b$ undergo blunt-flow translation with known velocity.
Figure 14:
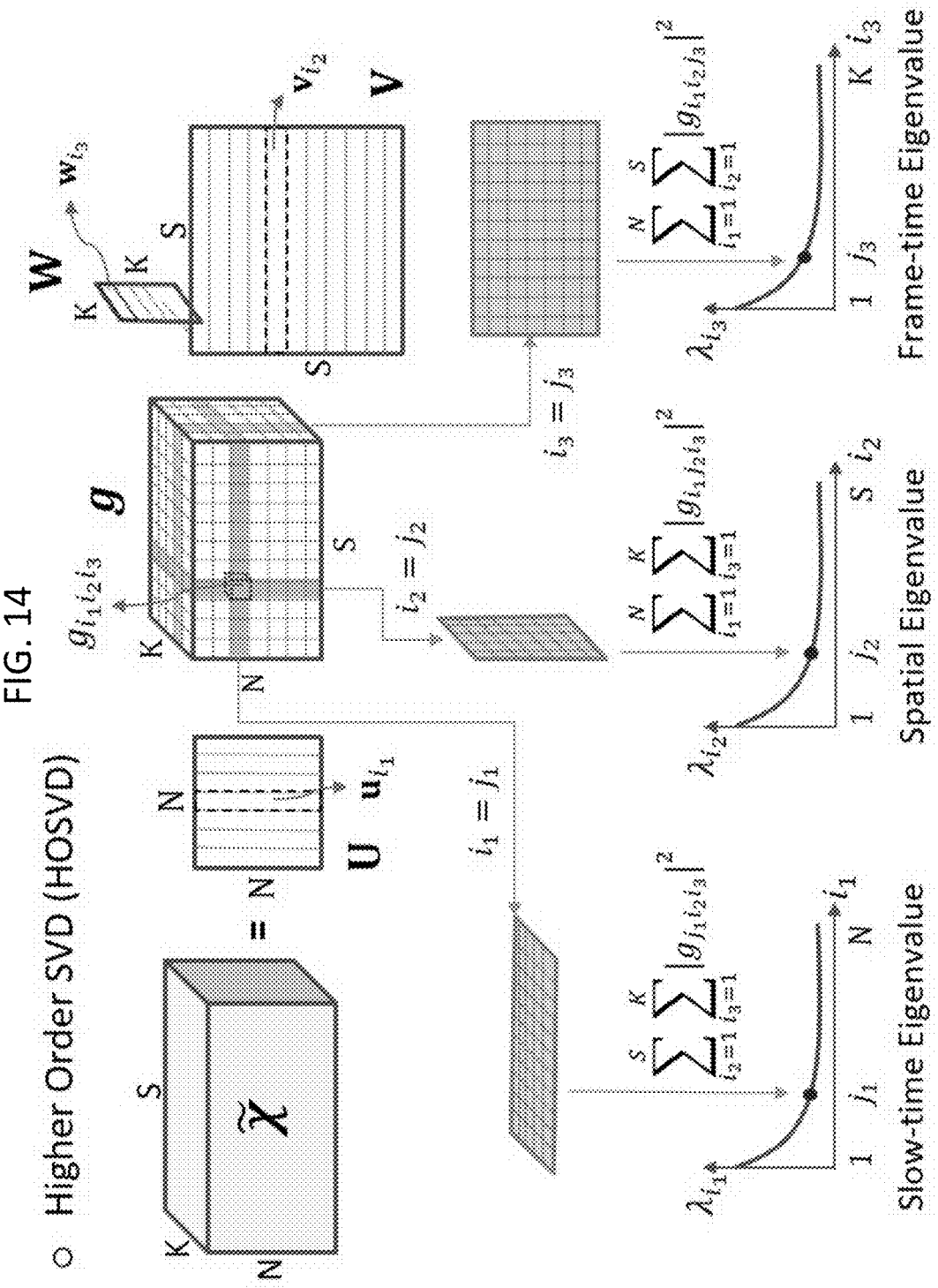
FIG. 14. Decomposition of 3D data array $\mathcal{X}'$ using HOSVD is illustrated. Element $g_{i1, i2, i3}$ is an element of the 3D core tensor G. That element is associated with slow-time eigenvector $u_{i1}$ and eigenvalue $\lambda_{i1}$, spatial eigenvector $v_{i2}$ and eigenvalue $\lambda_{i2}$, and frame-time eigenvector $w_{i3}$ and eigenvalue $\lambda_{i3}$.

For example, the top left PD image in FIG. 11 represents a different normal mouse hindlimb. Here we see two segments of arterial flow as indicated by arrows and the blue-green color. On the right, the ischemic hindlimb image from FIG. 10 is shown that displays no fast blood flow patterns. In both images, a region of interest is boxed that includes directed vascular flows away from the transducer; on the left, flow velocity is in the range 2-15 mm/s and on the right the flow velocity is in the range ±0.2 mm/s.

In the second row of FIG. 11, the first nine odd spatial eigenvectors are displayed as gray scale images. These are taken from data in the boxed regions in the figures above. The absolute values of elements in each spatial eigenvector are reshaped back into the shapes of the 2D image patches. The linear shape of the vessel within each eigenvector that is similar to that in the boxed image region above, except for the first eigenvector. The uniformity of spatial eigenvector 1 suggests it may be dominated by clutter, while the appearance of a vessel-like structure in the other eigenvectors suggest they are influenced by directional blood flow in the vessel. For this reason, at least the first spatial eigenmode through HOSVD filtering can be eliminated.

Images of the slow-time eigenvector spectra (third row in FIG. 11) and frame-time eigenvector spectra (fourth row) further reveal information about blood flow. In the first eigenvector spectrum (left-most column of the spectral images) the only nonzero value is at zero-frequency; consequently the first eigenvector offers no information about movement and should be discarded. The linear spectral pattern in the normal hindlimb slow-time spectral image between eigenvectors 5-10 (third row, left in FIG. 11) suggests a strong signal is present for fast directed blood flow. Because this flow is away from the transducer, the linear pattern appears along the negative-frequency axis, which shows there is directional flow information available. Notice the spectrum shows evidence of aliasing as the linear structure wraps from negative to positive frequencies at eigenvector 13. There is no linear spectral pattern for the normal hindlimb image in the corresponding frame-time spectrum (fourth row, left in FIG. 11) as expected for the slow, disorganized RBC movement associated with capillary perfusion. The red arrows along the abscissa indicate the upper and lower bounds on the eigenvector pass band set for HOSVD filtering.

There is also an asymmetric linear spectral pattern in the ischemic hindlimb image between eigenvectors 3-9 in the frame-time spectrum (fourth row, right in FIG. 11). This corresponds to the relatively-slow but downward-directed flow within the large vessel in the ischemic tissue. It is slow flow because it is found in the frame-time spectrum and the linear pattern indicates the flow is directed. Conversely, the slow-time eigenvector spectrum for the ischemic leg (third row, right in FIG. 11) is symmetric and diffuse, indicating no directed fast flow in this region.

In this example, by expanding the dimension of the acquired echo-data array and then strategically reducing the data dimension using adaptive HOSVD filters leads to images that suggest surprisingly improved perfusion sensitivity. At this point in development, the method offers images of signal power that describes relative flow and perfusion patterns.

Higher-order filtering as described herein can enhance the distinct information provided by each axis of the 3D data array, enabling visualization of blood components of the echo signal while effectively suppressing clutter and noise components.

The addition of frame-time data as a separate array dimension can allows increased sensitivity to slower flows through a longer acquisition period without discarding fast blood flow echoes offered by the slow-time array axis. One 3D acquisition processed via HOSVD effectively displays both blood components.

In this example, power-Doppler processing was used. It is noted that the eigenvector spectra seen in FIG. 11 contain information about the direction and spatial coherence of RBC movement. In principle, color-flow imaging can be performed. Also, 24 MHz ultrasonic pulses were used to couple the method to the small mouse model, which enabled sub-millimeter vessel diameter flows to be imaged with 5-mm tissue penetration.

The price paid for adding the frame-time axis in the echo-power estimator was that each PD frame required more than 1 s worth of data acquisition. Since perfusion can normally steady or slowly varying, the long acquisition could be inconsequential depending on the application. The added sensitivity and lower noise justify the extra time and effort, especially when imaging stationary echo data that describe steady RBC movements, as for the application described herein. The time required to compute one PD image frame was 19.1 s.

Acquisition of echo data can proceed for 1-30 seconds or longer, or from 1-20 seconds, or from 1-10 seconds of echo signals, which can be arranged into a 3D spatiotemporal data array.

Embodiments of this invention can provide a non-transitory machine-readable storage medium having stored therein instructions for execution by a processor which cause the processor to perform the steps of a method for imaging an object of interest containing a fluid. The steps can include acquiring beamformed ultrasound echo data comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension; re-ordering the spatiotemporal data array into a three-dimensional perfusion data array having one combined spatial dimension, one slow-time dimension, and one frame-time dimension, wherein the axial and lateral dimensions are combined into the one combined spatial dimension; filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array.

Examples of a non-volatile, non-transitory machine-readable storage medium include hard drives, read only memory (ROM), flash drives, solid state memory devices, electrically erasable programmable read only memory (EEPROM), DVDs, compact disc read only memory (CD-ROM), optical disks, magnetic disks, or any other storage media which may be used to carry or store program code having computer-executable instructions or data structures. The medium may be accessed by a general purpose or special purpose computer, such as a processor.

In additional embodiments, this invention may provide a computing system, which may include one or more processors, one or more memory devices, a file system, a communication module, an operating system, a user interface, each of which may be communicatively coupled or accessible by each of the other components.

A computing system can have an operating system, which may be arranged to utilize various hardware and software resources. An operating system can be arranged to receive and execute instructions for other components of the system.

Examples of computing systems include desktop computers, laptop computers, server computers, mobile phones or smartphones, wearable computing systems such as a watch, tablet computers, and portable computing systems.

Examples of a computing system include a processor, a special-purpose, or a general-purpose computer.

A processor may be arranged to execute instructions stored on a machine-readable storage medium. A processor may include a one or more microprocessors, various controllers, a digital signal processor, an application-specific integrated circuit, or a field-programmable gate array, which can be used to receive and/or transfer data, as well as execute stored instructions to transform the data. In some embodiments, a processor may receive, interpret, and execute instructions from program code or various media. A processor can receive and transform data, as well as store data in a memory, or file. In certain embodiments, a processor can fetch instructions from a memory or file and receive an instruction into a memory. Received or stored instructions can be executed. Instructions may include having a processor perform one or more steps of the method of this invention.

A memory or medium can store instruction or data files in a file system and can include a machine-readable storage medium. A machine-readable storage medium can be non-volatile. A machine-readable storage medium can be non-transitory. A machine-readable storage medium can have stored therein instructions which can be executable by a processor. A machine-readable storage medium can have stored therein data, which may have one or more of various structures.

A component for communication can be any apparatus, device, system, or combination of components which can transmit and/or receive data. Data can be transmitted and/or received via a communication line, or a network. In some aspects, a component for communication may be communicatively linked to other components at various locations.

Examples of components for communication include, wireless or wired, a modem, a network card, an infrared or visible communication component, an antenna, a communication chipset, a Bluetooth component, an 802.6 or higher device, a wide area network, a WiFi component, and a cellular communication component. A component for communication can exchange data over a line, wire or network to other components, devices or systems.

An apparatus of this invention can have components including one or more non-transitory machine-readable storage media, one or more processors, one or more memory devices, one or more file systems, one or more communication modules, an operating system, one or more user interfaces, each of which may be communicatively linked to one or more other components.

An ultrasound apparatus of this invention can have components including one or more non-transitory machine-readable storage media, one or more processors, one or more memory devices, one or more file systems, one or more communication modules, an operating system, one or more user interfaces, each of which may be communicatively linked to one or more other components. An ultrasound apparatus of this invention can include a processor and components for carry out steps for acquiring beamformed ultrasound echo data, wherein the data may have one or more separate spatial or temporal dimensions.

An ultrasound apparatus can have or more processors with one or more user interfaces for transforming data, for example, by re-ordering a data array into a different dimensionally-arranged data array.

An ultrasound apparatus can have or more processors with one or more user interfaces for transforming data, for example, by filtering a data array to create and store a filtered data array, and thereafter forming an image of an object of interest from the filtered data array.

An ultrasound apparatus of this invention can have a probe comprising a transducer for receiving RF and transmitting ultrasonic waves. A probe may have a transducer for receiving echo signals and transmitting echo data.

An ultrasound apparatus of this invention can comprise a high frequency transmitter or transducer for transmitting RF pulses with a center frequency of from 3 to 32 MHz. In some embodiments, an ultrasound apparatus may have a probe transducer for RF pulses with a center frequency of from 18 to 38 MHz.

Combinations of novel pulse-echo acquisitions and clutter filtering techniques can improve the sensitivity and the specificity of power Doppler (PD) images, thus reducing the need for exogenous contrast agent enhancement. Echoes can be acquired following bursts of Doppler pulse transmissions sparsely applied in regular patterns over long durations. The sensitivity of the acquisition to slow disorganized patterns of motion from the peripheral blood perfusion can be increased.

To counter a concomitant increase in clutter signal power, the temporal echo acquisitions can be arranged into two data-array axes, combine them with a spatial axis for the tissue region of interest, and 3D singular-value decomposition (SVD) clutter filtering can be used. Successful separation of blood echoes from other echo signal sources may require that the 3D SVD core tensor be partitioned. To distinguish clutter and blood subspaces, embodiments of this invention can provide a statistical classifier that may identify the core tensor subspace dominated by tissue clutter power.

In certain embodiments disclosed herein, subspace partitioning as required for improving PD imaging of peripheral perfusion can be performed. Methods of this invention, using echo simulation, flow phantom data, and in vivo data from a murine melanoma model can provide enhanced mapping of phantom flows and tumor perfusion signals at speeds less than 3 mL/min, especially for narrow eigen-bandwidth clutter signals. The methods of this invention can perform peripheral perfusion imaging.

In general, pulse-echo power Doppler (PD) imaging can be sensitive to slow disorganized movements of red blood cells (RBCs), and can be used for microvascular and perfusion imaging. PD signals are insensitive to blood speed and direction but highly vulnerable to tissue clutter and acquisition noise sources. PD methods described herein can provide improved sensitivity of echo signals to RBC movements with clutter filtering.

In general, Fourier-basis clutter filters can be applied, e.g., finite-impulse response, IIR. The Doppler equation provided a direct interpretation between the temporal Fourier coefficients and the blood velocity. However, it may now well accepted that Fourier-basis filters do not provide the best separation between the tissue and the slow-moving blood echoes. Singular-value decomposition (SVD)-basis filters can exploit the spatiotemporal nature of each echo acquisition. The 2D SVD can generate both the temporal and spatial bases so that characteristically strong echoes of spatially coherent tissue movements can be more readily separated from the weaker echoes of spatially incoherent blood perfusion echoes.

Embodiments of this invention can provide eigenfilters from a decomposition of the echo data temporal correlation matrix.

In some aspects, this invention provides peripheral muscle perfusion imaging to assess microvascular damage from ischemia and chronic metabolic disorders. For this task, the blood flow can be steady and nonstationary clutter echoes can arise mostly from small-amplitude muscle vibration and transducer motion.

In some embodiments, probing tissues with bursts of multicycle Doppler pulses over long durations can significantly increase the sensitivity of echo signals to peripheral perfusion RBC movement. RBC sensitivity can be increased by re-ordering the time axis into two array dimensions, labeled slow-time and frame-time axes, to produce a 3D echo-data array.

In such embodiments, a 3D data array can be decomposed using higher order SVD (HOSVD) filtering to produce three orthogonal basis sets corresponding to slow-time, spatial, and frame-time vector spaces.

Observation of perfusion signals could be enhanced and uncoupled from clutter by decomposing the data array and locating the blood subspace within the 3D core tensor elements.

In further embodiments described herein, the eigen-bandwidth for clutter can be transformed to provide clutter-blood subspace separability.

In additional embodiments, a statistical classifier can be applied to each core tensor element, which can identify the eigen-bandwidth for clutter filter design. The classifier can decides if a core element can be predominantly from a clutter source based on a vector of five signal energy and similarity features estimated from the decomposition eigenvalues and eigenvectors.

Embodiments of this invention may identify and utilize signal subspaces for clutter filter designs.

From the simulation, phantom, and in vivo tumor results, a consistent picture was found regarding the performance of the clutter filter for PD imaging from a 3D echo array.

Aspects of this disclosure may provide a classifier-based filter. The classifier-based filter can provide surprisingly improved tumor imaging.

In certain embodiments, for tumor imaging, a clutter filter of this disclosure removes clutter having narrow eigen-bandwidth. In such embodiments, the amplitude of the clutter motion may be small and spatially uniform, e.g., rigid-body motion, and the clutter subspace may be confined to the first few eigenstates. Consequently, the clutter and blood subspaces in G may be largely disjoint and suppressed with little effect on the blood subspace using a hard-threshold filter. In other words, the feature vector z from Equation (37) (below) in conjunction with the classifier of Equation (38) (below) may correctly label core elements of core tensor G.

In contrast, clutter signal power in the phantom data was strongly pulsatile with a broadband clutter subspace that overlapped the TM-blood subspace. The filter classifier was set to capture all of the blood power, and as a result, the postfilter signal power contained more clutter power at slow flows than at fast flows. For this reason, the PD image contrast was reduced in FIG. 21 as more clutter power was introduced. In addition, the resistance to flow through the dialysis fibers at the lowest flow states was highly variable; and few fibers often carried most of the flow at higher speeds. As flow increased above 2 mL/min, flow among fibers became more uniform. In effect, the flow phantom posed more challenges to successful clutter filtering than in vivo tumor imaging.

To improve the clutter filtering when tissues move with high amplitude and eigen-bandwidth, additional z components that can specifically identify those physical attributes can be used.

Figure 23:
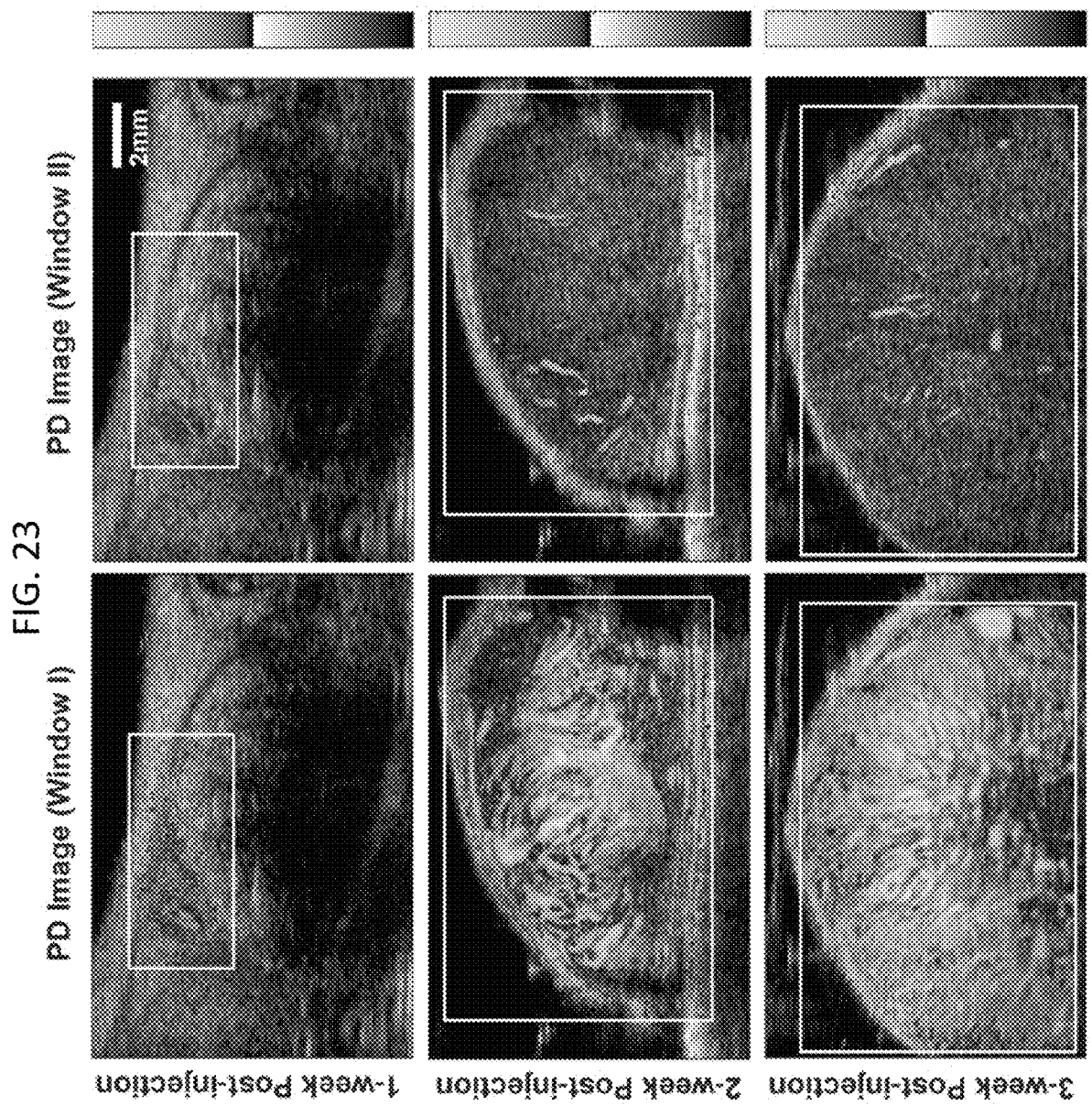
FIG. 23. PD images of a murine melanoma 1-3 weeks after implantation. Tumor size and microvasculature clearly increase with time. The left column displays PD maps of microvascular flow and perfusion for blood speeds <4 mm/min while those in the right column are flows >4 mm/min. All imaging was implemented in MATLAB 2015b on an Intel processor i5-4300U CPU, 2.50 GHz. HOSVD computation was performed using a truncation technique supported by TENSORLAB toolbox to minimize the running time. The time to compute all processing for one PD image (5.4 mm×7 mm, 1 week) is about 1 min. At 24 MHz, the blood-echo SNR is high enough to use two-cycle Doppler pulses, which enhances the spatial resolution sufficiently to see microvessels.

In further embodiments, soft-threshold decision functions can be used that can recognize when more than one signal source is contributing to a core element. The tumor images of FIG. 23 show that peripheral microvascular imaging offers clutter conditions where the methods of this invention succeed. In these studies, the transducer was placed into a fixture so that the transducer motion relative to the tissue was only possible by breathing and not sonographer hand motions. When large rigid-body movements are present, preprocessing techniques can be used to adjust the echo phase and amplitude to minimize the effects of large motion clutter.

Note that the simulation and phantom data provide small-vessel flow conditions but no capillary perfusion-like signal, the latter being characterized by the slowest and most spatially disorganized RBC movements. Both the microvascular flow and the perfusion are present in FIG. 23.

The perfusion was well represented in the PD spectrum that does not depend on the Doppler angle; however, unlike color-flow images, PD images offer no velocity information. In some embodiments, speed ranging data was obtained by partitioning eigenvector spectra.

In embodiments described herein, eigenvector spectral images display distinct linear patterns when RBC movement is directed, as in vessel flows, and diffuse patterns when RBC movement is disorganized, as in capillary perfusion. The 3-D eigenspace provided by HOSVD processing can offer a wealth of specific information about scatterer movement that may be encoded in pulse-echo signal arrays.

The sensitivity of PD images to tissue perfusion was increased by creating a frame-time axis in the acquired echo data array in addition to the slow-time and spatial axes. The frame-time axis provides a high density of Doppler spectrum samples at frequencies corresponding to tissue perfusion signals. The perfusion signal was uncoupled from the tissue clutter using a 3-D SVD that generates a 3-D core tensor and three sets of eigenvectors describing the slow-time, spatial, and frame-time features of the echo signals.

In embodiments of this invention, a feature vector classifier can be described as having elements computed from the 3-D eigenspace. Three of the features report eigenvalue energy and two are similarity measures. This statistical classifier examines each core tensor element to decide if it can be predominantly of clutter or nonclutter origin. Coupling the clutter filter with an acquisition noise filter and the velocity discriminator, we image the fast and slow blood-flow states in vivo. The blood and clutter powers are well separated for narrow eigen-bandwidth clutter signals but the overlap of these subspaces can be progressively increased as the clutter eigen-bandwidth increases.

In this disclosure, novel pulsed-Doppler methods for perfusion imaging are validated using flow phantoms. Techniques tested qualitatively at 24 MHz in vivo were examined quantitatively at 5 and 12.5 MHz using phantoms with known adjustable properties.

Embodiments of this invention utilize eigenstates of higher order singular value decomposition (HOSVD) clutter filters to reveal echo-signal sources such that the blood subspace can be isolated for imaging.

A variety of measurement situations that assess the effectiveness of clutter filters are shown, and the accuracy and precision of flow velocity and signal power estimates are measured.

In some aspects, this invention provides color-flow and power-Doppler phantom imaging showing that perfusion imaging can reliably be obtained without contrast agent enhancement.

The results show that velocity measurements may be much less biased than power-Doppler measurements for flows <4 mL/min generating micro-fiber velocities <1.2 mm/s.

In further embodiments, clutter-filter parameters can be determined to limit power-Doppler images to specific velocity ranges.

Appendix A below describes how pulse sampling can be adjusted to increase blood-echo strength at different velocities.

In some aspects of this invention, combinations of temporal pulse sequences can expand data dimensionality, and clutter filtering techniques can be used to enhance the sensitivity and specificity of pulsed-Doppler echoes to slow-moving blood flows.

In certain embodiments, perfusion imaging can be improved using commercial instrumentation without the use of contrast media.

In additional embodiments, sensitivity to perfusion echoes can be improved by sampling each location in tissue over time using sparse packets of Doppler pulses. Long-duration (1-20 s) pulse-echo acquisitions sample the Doppler frequency axis within the range of slow-moving red blood cell (RBC) velocities. The relationship between pulse sequence parameters and Doppler frequency-domain sampling can be described. Long-duration acquisitions can be acceptable if the echo statistics are wide-sense stationary in time, as often occurs with peripheral perfusion imaging.

In general, as sensitivity to slow flow increases, so may the sensitivity to tissue-clutter echoes. Thus, effective clutter filtering can be used to improve the specificity of perfusion imaging to slow-moving blood echoes.

Embodiments of this invention show that 2-D singular-value decomposition (SVD) filtering may be effective at separating clutter-blood subspaces in echo data when characteristic differences between blood and tissue motions are recorded.

The process for 2-D echo-data arrays considers an S×N array of complex in-phase/quadrature (IQ) samples, $X \in \mathbb{C}^{S \times N}$ arranged as a Casorati matrix. That is, spatial signals at fixed time are indexed along columns and temporal signals at fixed position are indexed along rows. Decomposing 2D X via SVD, a low-rank approximation can be found to the singular value matrix with singular values arranged in decreasing order.

The first few singular values can be the largest, arising from tissue scatterers having echogenicity significantly greater than that from RBCs. These singular values may define the clutter subspace for the echo data. When they are few in number (narrow eigenbandwidth), tissue motion may be unidirectional and low-amplitude, e.g., from vascular pulsatility, breathing, and probe movements.

The next few singular values can be from blood echoes captured within the frequency bandwidth of the pulse. Singular values within the blood subspace may tend to be lower in magnitude and more numerous than those found in the clutter subspace. This can indicate the weak echogenicity and less spatially-coherent movement of RBCs relative to clutter. Examples include laminar flow in larger vessels but not capillaries as the pulse repetition frequency can often be too high and the acquisition too short to sense and separate perfusing RBCs from clutter.

Tissue and blood subspaces of data array X may typically occupy a small fraction of its total eigenbandwidth, in contrast with broadband acquisition noise that contributes to each singular value. The tissue and blood subspaces are not independent of each other but their dependence may usually lower in an SVD spectrum than in other basis decompositions, e.g., Fourier, in part because the basis adapts to each set of data. SVD clutter filtering may be superior to Fourier and temporal eigenfilters if the clutter and blood subspaces are more separable.

Figure 24:
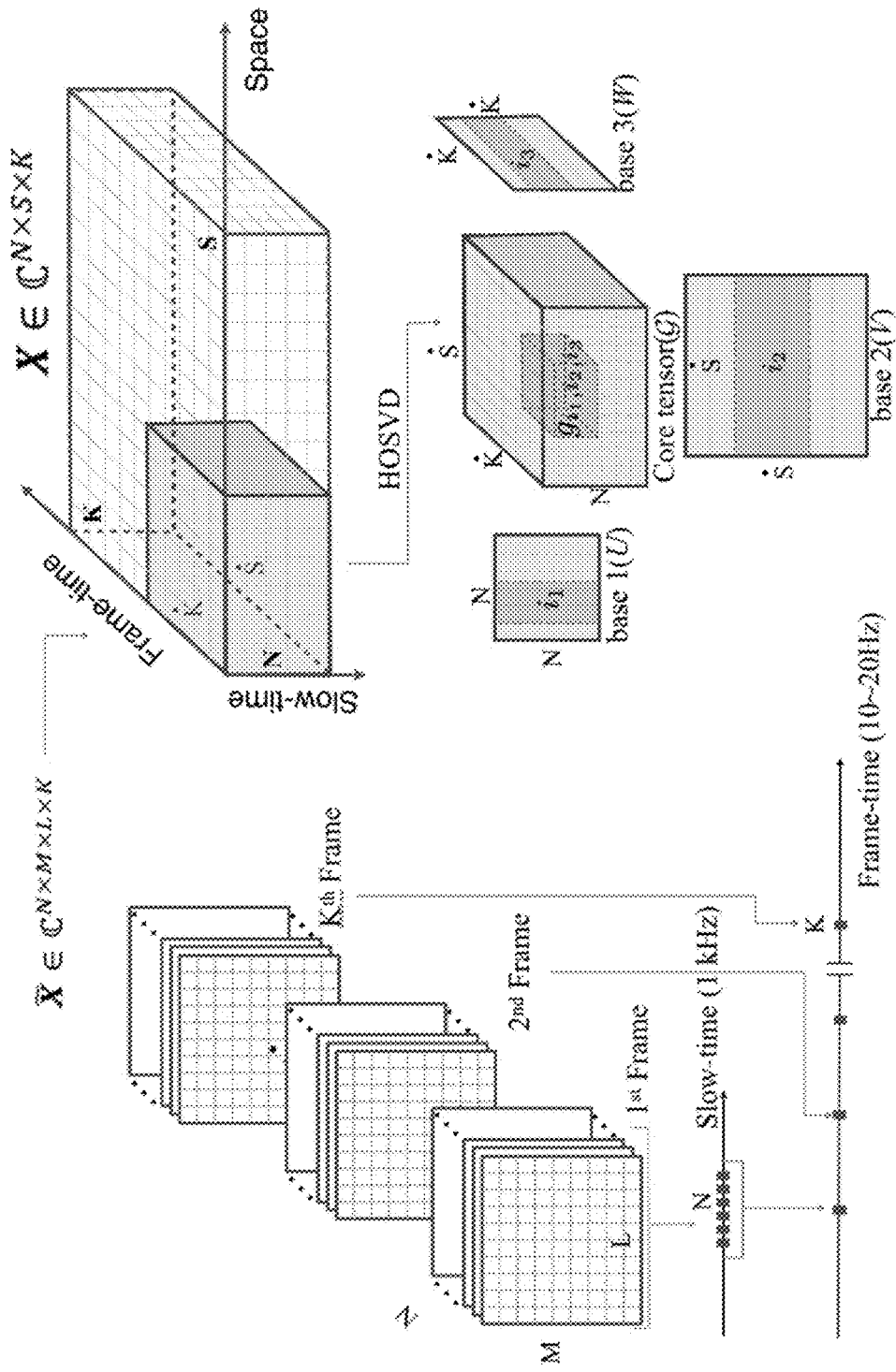
FIG. 24. Each Doppler frame initially consists of an N×M×L array of complex-valued IQ echo samples, where M×L are, respectively, the numbers of fast-time (axial) samples and lateral scan lines recorded; they form the power-Doppler image plane. N is the number of pulse transmissions in the Doppler frame at each spatial location—the slow-time dimension. Lexicographical reordering of the two spatial dimensions into one, M×L->S, results in data array $\mathcal{X}' \in \mathbb{C}^{N \times S}$. Recording K Doppler frames adds a frame-time data axis, which yields the 3D echo data array $\mathcal{X} \in \mathbb{C}^{N \times S \times K}$. Array $\mathcal{X}$ is further partitioned into small overlapped volumes along the spatial and frame-time axes, d$\mathcal{X}$/dt$\in \mathbb{C}^{N \times dS/dt \times dK/dt}$ and each sub volume is decomposed via HOSVD. We clutter and noise filter the echo data by suppressing singular values within each core tensor G. Filtered G is recombined with eigenvector matrices U, V, W to form (d$\mathcal{X}$/dt)$_B$, the filtered echo signal for CF and PD imaging.

Embodiments of this invention can provide extended SVD clutter filters to 3-D echo-data arrays. Array elements $X_{n,s,k}$ can be organized with N slow-time samples, S spatial samples, and K frame-time samples, as illustrated in FIG. 24. A frame-time sampling rate set about 100 times lower than the slow-time sampling rate increases sensitivity to perfusion echoes. In some embodiments, for effective clutter filtering, the slow-time and frame-time samples can be represented in the echo-data array by separate dimensions. A 3-D basis decomposition exploits characteristic differences among these data dimensions.

Three-dimensional data arrays can be decomposed using higher-order SVD (HOSVD) analysis. HOSVD filtering was implemented on a laptop using a fast algorithm. The decomposition yielded three orthogonal matrices whose columns are eigenvectors of spatial, slow-time, and frame-time array axes. Instead of a diagonal 2-D core matrix of singular values, a 3-D core tensor was found with orthogonal modal planes and singular values arranged in descending order along each axis. For cluttering filtering, core-tensor values and eigenvectors can be parsed to identify echo-source subspaces.

Embodiments of this invention provide flow-phantom echo data under known conditions to validate the reliability of color-flow (CF) and power-Doppler (PD) imaging. Because the flow states are known, we are able to explore their relation to eigenstates to explain how the HOSVD filter operates and to evaluate performance experimentally. These results are compared with other statistical methods for setting SVD clutter filter parameters to explore strengths and weaknesses of different approaches. The results first report on the accuracy and precision of flow estimates to motivate various approaches to filter parameter selection.

Embodiments of this invention can extend methods for imaging and filtering to pulse frequencies as low as 5 MHz to gain depth of penetration. In some aspects, the methods can be sensitive to perfusion changes in ischemic muscle and vascular tumors. Embodiments of this invention provide reliability of in vivo imaging results.

In general, velocity estimation via CF imaging can be quantitative.

The echo-data array may be arranged into distinct spatiotemporal dimensions that provide physical meaning to eigenvectors emerging from the decomposition. Appropriate sampling can ensure the frame-time dimension provides sensitive information about perfusion. The slow-time data axis offers little information regarding perfusion, although it provides noise reduction through signal averaging.

The spatial dimension can provide very specific information needed for clutter rejection. When the spatial features of clutter movement are similar to perfusion, an HOSVD clutter filter may not be able to completely separate clutter from perfusing blood echoes. This occurred in phantom I. Since clutter motion from water pulses propagated along the aligned cellulose fibers, there was little clutter-blood discrimination from the spatial eigenvectors; e.g., see the eigenimages of FIG. 30.

Figure 31:
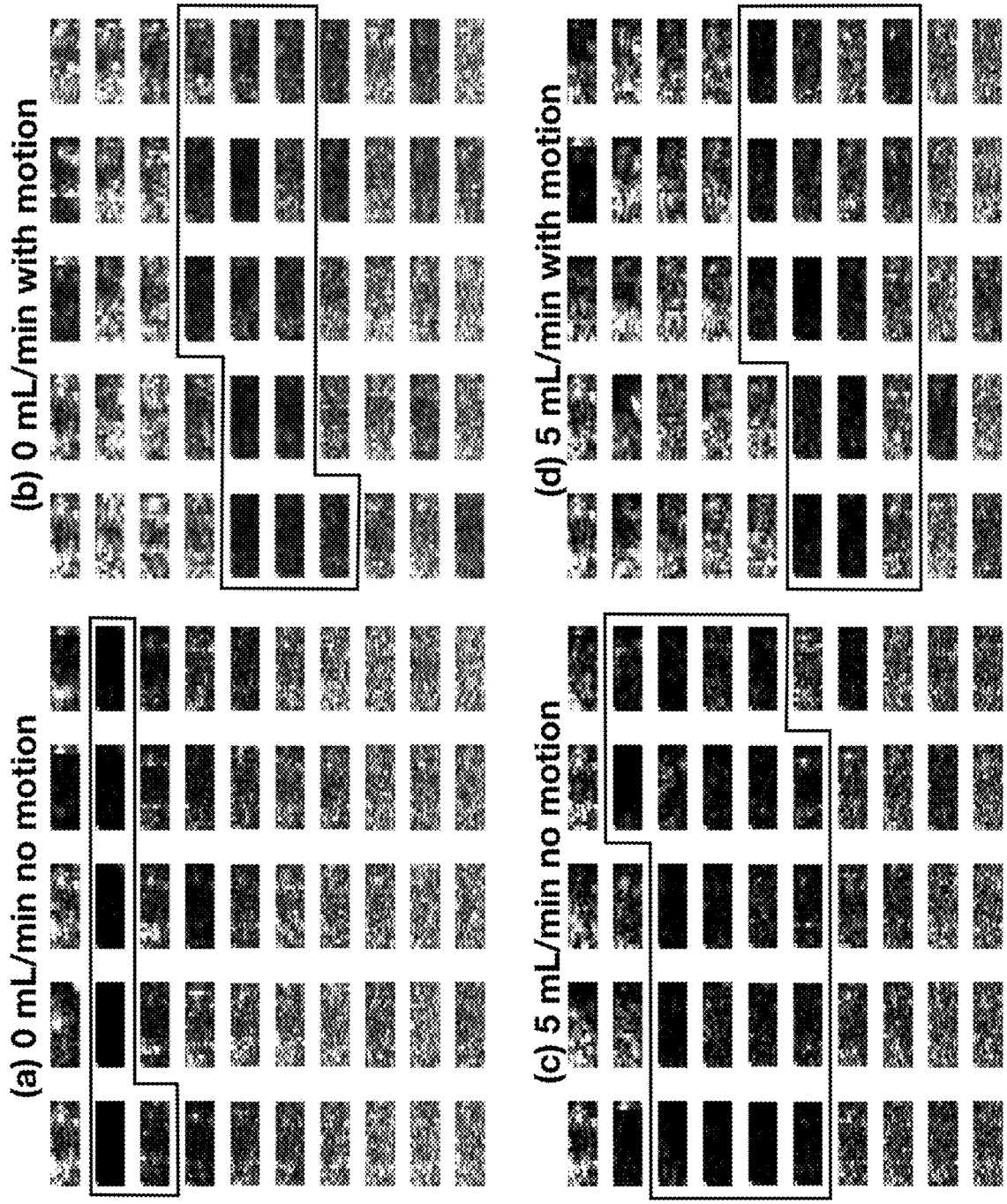
FIG. 31. Eigenimages from the largest 50 spatial eigenvalues for phantom II at 5 MHz. Flow and clutter parameters are indicated. Boxes around images identify our estimation of the blood subspaces for the four experiments.

In contrast, when fibers are less directional, as in phantom II, the eigenimages of FIG. 31 provided greater separability. Fortunately, this latter situation is common in vivo. Hence phantom I presented a more difficult challenge than that expected in peripheral vascular assessments. Also, when a point source of clutter is introduced as in phantom II (tapping on the container), the focal property of the clutter source increased the discriminability of the signal eigenbandwidth (clutter+blood) from noise, which aided in overall subspace separability. This finding does not directly provide an approach to more effective clutter filtering in clinical imaging, but it does underscore the importance of searching for spatial cues.

Figure 26:
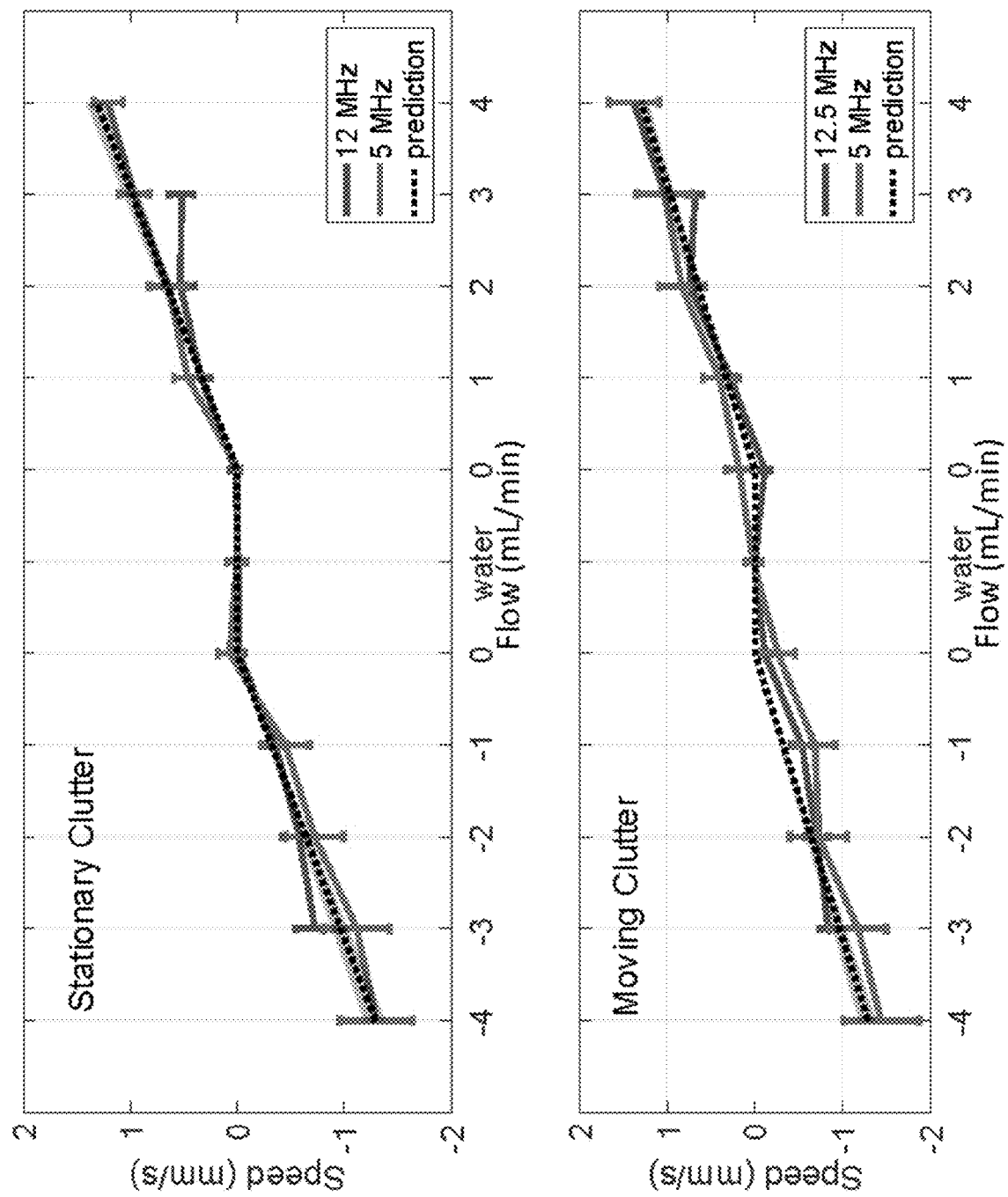
FIG. 26. Spatially-averaged velocities, $\bar{\upsilon}$ for N=3 experiments, are estimated as a function of TM blood flow rate for stationary (top) and moving (bottom) clutter. Error bars indicate ±1 standard deviation. The narrow gray area near the prediction line indicates the range of stopwatch measurements of fluid velocity $\bar{\upsilon}'$. Uncertainty for both measurements increases with flow, reflecting a high variation in individual fiber flows. The center three measurements all indicate a no-flow state. The measurement labeled 'water' has stationary water in the fibers while the other two labeled '0 mL/min' have stationary TM blood in the fibers.
Figure 29:
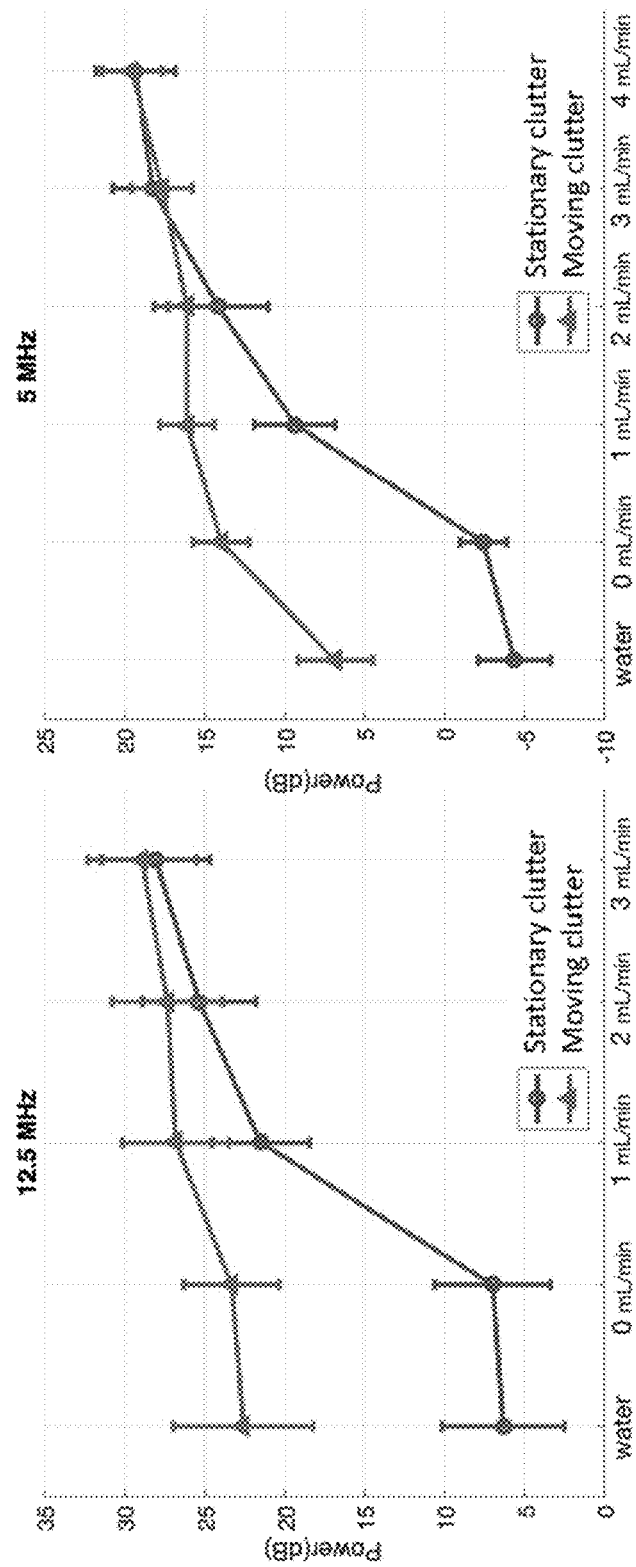
FIG. 29. Spatially averaged post-filtered echo power is plotted versus input flow for stationary and moving clutter. Error bars indicate standard errors for N=3 experiments. There is no flow in the fibers for the first two points plotted. The 0 mL/min values have stationary TM blood present, which can generate more signal power than the stationary water state.

Stationary clutter can generate a narrow eigenbandwidth subspace while periodic clutter motion can generate a broad eigenbandwidth subspace. In both situations, accurate velocity estimates down to 1 mL/min flow were obtained as seen in FIG. 26. Accurate measurements were found despite the inability to completely separate clutter from TM blood-flow signal power, provided aliasing was avoided. Velocity estimates may have been less affected because the clutter power passing through the HOSVD filter adds power symmetrically across the velocity range of blood flow within the Doppler spectrum. Under the same conditions, however, power-Doppler estimates are more significantly biased high, as seen in FIG. 29.

In some embodiments, SVD filtering can adapt to the specifics of each acquired data set. SVD may distinguish spatiotemporal features that characterize blood flow as distinct from clutter echoes.

Embodiments of this invention may first create data-array dimensions rich in task information through pulse sampling (described below). Of course, the transmission frequency of the pulse may play a fundamental role in enhancing task information by determining the spatial resolution for imaging microvascular flow, setting the relative contributions of tissue and blood echoes, and regulating the echo SNR as a function of tissue depth.

Data can be acquired in two spatial and two temporal data dimensions. Finding no distinct clutter information encoded in the two spatial dimensions, data dimensionality was reduced by reordering the two spatial axes into one. The remaining 3-D echo-data array was decomposed in 3D via HOSVD, which can generate a basis set for each data axis. Each set of eigenvectors may provide specific information; i.e., the frame-time basis can be rich in perfusion information, the slow-time dimension may provide information about faster vascular flow, and the spatial dimension may bear significant information needed to distinguish echo-source subspaces when source features are distinctive.

Figure 36:
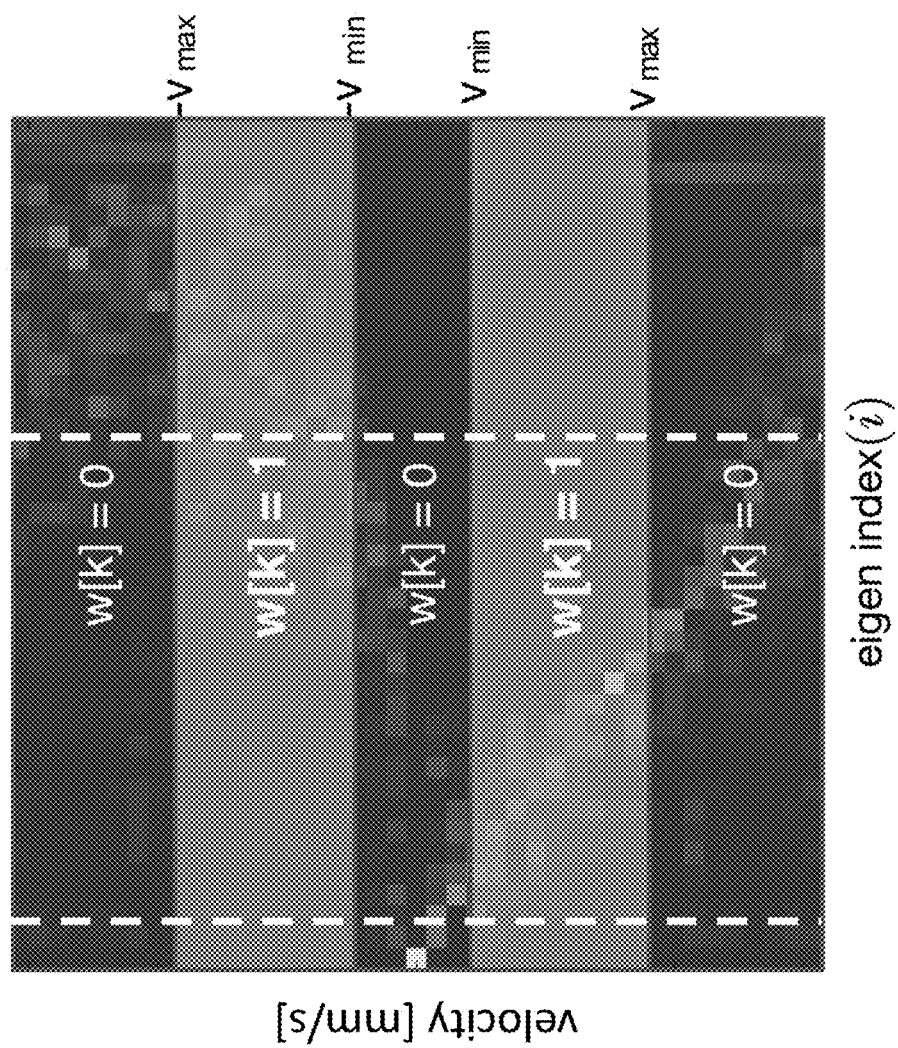
FIG. 36. An eigenspectrum similar to that of FIG. 33 is annotated to illustrate a velocity discrimination method for PD imaging. Left and right dashed lines indicate, respectively, the clutter and anti-aliasing boundaries in the echo filter. The gray regions define the selected Doppler frequency range, $\pm(\upsilon_{min}, \upsilon_{max})$. Echo power within these four bounds form PD images.

In FIGS. 31 and 36, fixed filter thresholds were set by visually inspecting a form of the eigenvectors that provided physical intuition. This approach can validate the results and provide fixed filter thresholds for SVD filters.

In additional embodiments, statistical metrics and classifiers can be used to set clutter and noise filter thresholds automatically, avoiding the need for operator decisions.

In certain aspects of this invention, the sensitivity of blood perfusion imaging with commercial instruments can be surprisingly and advantageously increased by appropriately setting the Doppler pulse acquisition sequence for the expected velocity ranges. Arranging the echo-data array into spatial and temporal dimensions that carry unique signatures for all contributing echosignal sources, the array can then be decomposed using HOSVD methods. Eigenvector matrices resulting from the decomposition can be partitioned for clutter and noise filtering by taking into account the unique characteristics of echo sources along each data dimension. When spatiotemporal features of blood and clutter echoes are quite similar, the SVD filter may be less effective than in situations where the features are distinct. Embodiments of this invention can provide SVD filtering for more fully realizing distinctive spatiotemporal features of the contributing echo sources that are captured along data dimensions.

Notation

The structure of the data array can be central to understanding the method. Arrays may be described using the following notations. Scalars are written as lower-case letters (a, b, . . . ), column vectors as bold lower-case letters (a, b, . . . ), matrices as bold capital letters (A, B . . . ), and multi-dimensional arrays or tensors as bold calligraphic capital letters (A, B, . . . ). Integers $i, i_1, i_2, i_3$ are indices; e.g., the ith element of vector a is denoted as $a_i = a[i]$, the $(i_1, i_2)$th element of matrix A as $a_{i_1,i_2} = A[i_1, i_2]$, and the $(i_1, i_2, i_3)$th element of third-order tensor A as $a_{i_1,i_2,i_3} = A[i_1, i_2, i_3]$.

Echo Data Arrays

Doppler-mode acquisition involves the recording of echoes following a series of narrow-band pulse transmissions along one or more scan lines. After each pulse transmission, M echoes are recorded at fast-time sampling interval T. (See FIG. 1.) Let x represent the complex envelope of the recorded echo signal, i.e., the demodulated analytic signal. Each element of M×1 vector x is a complex number with real and imaginary components given by in-phase and quadrature values. The mth fast-time sample, for $1 \leq m \leq M$, corresponds to axial depth $z = z_0 + (m-1)cT/2$ where $z_0$ is the distance between the transducer surface and the beginning of the recorded signal, and c is the compressional wave speed.

For each line of site, echo vectors are recorded N times following each of N pulse transmissions to form a packet of echo data. Pulses are transmitted on the slow-time interval T'>MT, where 1/T' is the pulse repetition frequency (PRF). Conventional power and color Doppler acquisitions record a packet of echo data for each of L adjacent lines of site separated laterally by the spatial interval D. All packets for one spatial frame form an (N×M x L) array of echo data that we call a Doppler frame. This conventional 3-D array represents two spatial dimensions and a slow-time dimension.

K Doppler frames are recorded on the time interval T''>>T' to generate the frame-time dimension of a 4-D data array. To measure perfusion, we set T=0.042 ρs (24 Msamples/s fast-time sampling rate), T'=1 ms (PRF=1 kHz), and T''=0.11 s (frame-repetition frequency=9 Hz). This 4-D data array is represented by $\mathcal{X} \in \mathbb{C}^{N \times M \times L \times K}$.

The second and third dimension of X are associated with axial and lateral spatial domain, respectively, that are not separately analyzed. Therefore the array is reordered as follows:

$$\mathcal{X} \in \mathbb{C}^{N \times S \times K}, \text{ such that } \mathcal{X}_{n,s,k} = \tilde{x}_{n,m,l,k}, \quad \text{Equation (1)}$$

where s=m+(l−1)M and S=ML.

The common assumption is that echo data arise from three independent physical sources: tissue clutter C, blood scattering B, and acquisition noise N. Thus, X has three components, $$\mathcal{X} = \mathcal{C} + \mathcal{B} + \mathcal{N}, \quad \text{Equation (2)}$$

where each have size N x S x K. White acquisition noise ensures that X is full-rank. Finally, B includes signals from fast arterial flow and slow capillary perfusion.

Eigen-Based Filter

For echo data well represented by a zero-mean Gaussian process, the correlation (and covariance) matrix contains all of the statistical information for that vector space. Eigenfilters decompose the multi-dimensional data array using eigenvectors of the correlation matrix. These eigenvectors are orthogonal and uncorrelated, and, under the Gaussian assumption, their eigen-components are as statistically independent as possible. An eigenvalue divided by the sum of all eigenvalues describes the fraction of variance contributed by that eigenmode. Because tissue scattering is often more echogenic than blood scattering, and both contribute more to the variance than noise, the common assumption is that clutter dominates the first few eigenvalues, blood the next few, and the rest are noise. Eigen-based filters isolate the blood subspace by identifying the clutter-blood and blood-noise interfaces and suppressing eigenvalues outside the blood subspace. The method used to construct the filter depends on how many of the data dimensions we choose to apply, as now explained.

1st-order Eigen-based Filter

Let $X \in \mathbb{C}^{N \times S}$ be a matrix indicating the $\alpha$th Doppler frame of echo data such that $X = X_{i_3 = \alpha} \in \{1, \ldots, K\}$. An empirical correlation matrix of the temporal signal can be computed and then decomposed as follows.

$$R_N = XX^\dagger = U\Lambda U^\dagger \in \mathbb{C}^{N \times N} \qquad \text{Equation (3)}$$

where $\dagger$ denotes conjugate transpose. $\Lambda$ is a diagonal matrix of eigenvalues sorted in descending order. The columns of unitary matrix $U = [u_1, \ldots, u_N]$ are the corresponding eigenvectors for $R_N$. From Eq. (3), X is easily decomposed in terms of temporal eigenvectors using $$X = UU^\dagger X = \Sigma_{i=1}^N u_i u_i^\dagger X. \qquad \text{Equation (4)}$$

Identifying the rank of the clutter and blood subspaces by c and b, respectively, data are processed using the 1-D eigen-based clutter filter, $$\hat{B} = \Sigma_{i=c+1}^{c+b} u_i u_i^\dagger X. \qquad \text{Equation (5)}$$

That is, only those eigenvectors associated with the blood subspace are used to resynthesize the decomposed echo data, which is now represented by matrix $\hat{B}$. Subsequently, the power $\hat{B}$ is mapped into the PD image.

Note that when the echo signals are wide-sense stationary and the impulse response for the pulse-echo system is linear time-invariant such that the system matrix is well approximated by a circulant matrix, then the eigenfilter components are equal to Fourier components. The difference is that finite-impulse response (FIR) clutter filters are generally fixed over the imaged region while the eigenfilter described by Equation (5) adapts to the echo data.

Similarly, an empirical correlation matrix of the spatial signal can be computed and then decomposed using $$R_S = X^\dagger X = V\Lambda' V^\dagger \in \mathbb{C}^{S \times S} \qquad \text{Equation (6)}$$

where eigenvalue matrix $\Lambda'$ has a different size but contains the same nontrivial eigenvalues as $\Lambda$ in Equation (3). The columns of unitary matrix $V = [v_1, \ldots, v_S]$ are eigenvectors in the spatial domain. Equation (6) is not typically used for power estimation although it is an important component of the second-order filters described below.

2nd-Order Eigen-Based Filter

SVD is an analogous tool for decomposing data spanning two vector spaces, in this case time and space. Matrix $X \in \mathbb{C}^{N \times S}$ is decomposed using $$X = U\Sigma V^\dagger = \Sigma_{i=1}^r \sigma_i u_i v_i^\dagger. \qquad \text{Equation (7)}$$

This form of X is known as the Casorati matrix, whose rows comprise vectorized frames of the image series. Assuming white acquisition noise, the rank of X is $r = \min(N, S)$, which is also the rank of $\Sigma \in \mathbb{R}^{N \times S}$, a diagonal matrix of singular values $\sigma_i$ sorted in descending order. Analogous to Eq. (5), the best estimation of the blood-signal matrix, in a least-squared sense, is found by processing $$\hat{B} = \Sigma_{i=c+1}^{c+b} \sigma_i u_i v_i^\dagger = \Sigma_{i=c+1}^{c+b} u_i u_i^\dagger X v_i v_i^\dagger. \qquad \text{Equation (8)}$$

Eqs. (5) and (8) both seek to identify the blood component of echo-signal variance along the slow-time dimension. N is typically small, which may not provide enough eigenmodes to uniquely identify the blood-scattering subspace given the similarity of perfusion and clutter velocities. Adding frame-time samples increases the number of eigenmodes in a way that also increases the SNCR.

Power contained in filtered data $\hat{B} \in \mathbb{C}^{N \times S}$ is computed using $$p[i_2] = \frac{1}{N} \sum_{i_1=1}^N |\hat{B}[i_1, i_2]|^2, \qquad \text{Equation (9)}$$

where $p \in \mathbb{R}^S$ can be converted into an image $P \in \mathbb{R}^{M \times L}$. Power estimates are log compressed and scan converted when displaying the image for the $\alpha$th frame acquired.

3rd-Order Eigen-Based Filter

Figure 2:
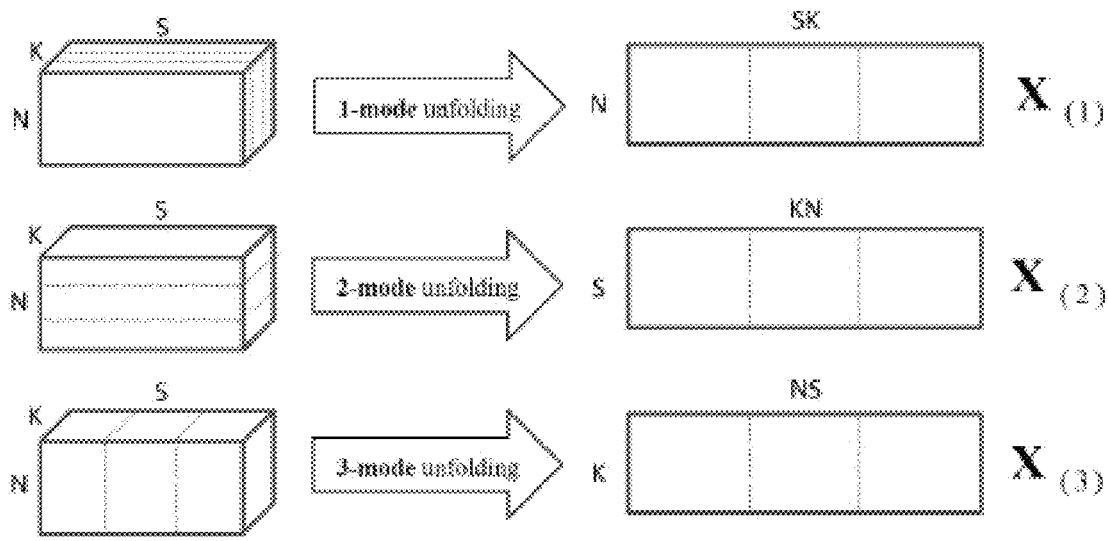
FIG. 2. The figure illustrates 1, 2 and 3-mode unfolding operation of the 3rd-order tensor data X.

SVD methods can be extended to 3-D data by decomposing $X \in \mathbb{C}^{N \times S \times K}$ into three empirical correlation matrices. First, consider the following related to tensor processing:

Unfolding. A 1-mode unfolding operator $X_{(1)} = [X]_1$ arranges elements of tensor $X \in \mathbb{C}^{N \times S \times K}$ into a matrix $X_{(1)} \in \mathbb{C}^{N \times SK}$ where columns of the matrix are slow-time signals. Likewise, 2-mode and 3-mode unfoldings generate the matrix $X_{(2)} \in \mathbb{C}^{S \times KN}$ and $X_{(3)} \in \mathbb{C}^{K \times NS}$ where columns of the matrices are space and frame-time signals, respectively. These are illustrated in FIG. 2.

Empirical Correlation Matrices are found using the unfoldings as follows, $$R_N = [X]_1 [X]_1^\dagger = U\Lambda_N U^\dagger \in \mathbb{C}^{N \times N}$$

$$R_S = [X]_2 [X]_2^\dagger = V\Lambda_S V^\dagger \in \mathbb{C}^{S \times S}$$

$$R_K = [X]_3 [X]_3^\dagger = W\Lambda_K W^\dagger \in \mathbb{C}^{K \times K} \qquad \text{Equation (10)}$$

Subscripts on the correlation matrices indicate the X dimension preserved. $\Lambda_N, \Lambda_S$ and $\Lambda_K$ are diagonal eigenvalue matrices for the three modes, and U, V and W are the corresponding eigenvector matrices.

n-mode Rank of tensor X equals the rank of the matrix generated by n-mode unfolding, $$r_n(X) = r([X]_n), n \in \{1, 2, 3\}. \qquad \text{Equation (11)}$$

Thus, 1-mode, 2-mode and 3-mode rank of X is the same as the rank of $R_N, R_S$ and $R_K$.

Analogous to Eq. (7), the HOSVD of X is $$X = G \times_1 U \times_2 V \times_3 W \qquad \text{Equation (12)}$$

$$= \sum_{i_1=1}^{r_1} \sum_{i_2=1}^{r_2} \sum_{i_3=1}^{r_3} g_{i_1, i_2, i_3} u_{i_1} \times v_{i_2} \times w_{i_3},$$

where x denotes an outer-product operation. See Appendix B below for an element-based description of the outer products.

$G \in \mathbb{C}^{N \times S \times K}$ is a "core tensor" analogous to matrix $\Sigma$ in Eq. (7). The columns of U, V and W are the eigenvectors for the slow-time, spatial and frame-time dimensions, respectively. Also $r_1$, $r_2$, and $r_3$ are the n-mode ranks of G. G is computed using the unitary property of eigenvector matrices, $$G = X x_1 U^\dagger x_2 V^\dagger x_3 W^\dagger. \qquad \text{Equation (13)}$$

Components of G are orthogonal in that the dot product between planes in the array, $$<G_{i_n=\alpha}, G_{i_n=\beta}> = 0, \alpha \neq \beta, \forall n, \forall \alpha, \forall \beta, \qquad \text{Equation (14)}$$

and the squared norm of matrix $\|G_{i_n=j}\|^2$ equals a jth largest eigenvalue of $R_n$ for n=1,2,3.

HOSVD filtering is analogous to that described for SVD filtering in Eq. (8). However, note that the 1,2,3-mode rank of X are not necessarily the same, and its core tensor G is not diagonal. Thus, an advantage of HOSVD filtering is the added flexibility in defining the rank of the clutter and blood subspaces.

The HOSVD filter applied to X (FIG. 3) yields the filtered echo-signal tensor, $$B = \sum_{i_1=c_1+1}^{c_1+b_1} \sum_{i_2=c_2+1}^{c_2+b_2} \sum_{i_3=c_3+1}^{c_3+b_3} g_{i_1,i_2,i_3} u_{i_1} \times v_{i_2} \times w_{i_3}$$

$$= \sum_{i_1=c_1+1}^{c_1+b_1} \sum_{i_2=c_2+1}^{c_2+b_2} \sum_{i_3=c_3+1}^{c_3+b_3} X \times_1 u_{i_1} u_{i_1}^\dagger \times_2 v_{i_2} v_{i_2}^\dagger \times_3 w_{i_3} w_{i_3}^\dagger. \qquad \text{Equation (15)}$$

Constants $c_n$ and $b_n$ are, respectively, the ranks of the clutter and blood subspaces on i-th mode eigenspace. Section 4 describes an approach to finding 3-D regions within the G array that best represents the blood components of echo power.

In contrast with Eqs. (5) and (8), the rank reduction provided by HOSVD filtering in Eq. (15) is not optimal in the least-squares sense. That is, the mean-square error between X and one or more signal components may not be minimized by this filter. Nevertheless, it is a good approximation and can be implemented more simply and quickly than that of iterative methods that can obtain the least-squares solution.

Implementation

Perfusion is assumed constant over the 17 slow-time samples (17 ms) recorded in this study. However the echo-signal mean and covariance matrix in the unfolded X, e.g., Eq. (10), do vary over the 6.4 mm×14.4 mm→200×240=48,000 spatial samples and over the 17 frame-time samples (1.9 s) typically applied to each PD image. Although 100 frames were recorded (11.1 s), blocks of 17 frames are applied to any one estimate. See Table 3 for data acquisition details. Since the number of spatial samples is much larger than either of the time samples, the data are spatially windowed to compute local filters. In this way, an HOSVD filters adapt to properties of recorded data along any of the array axes.

Figure 4:
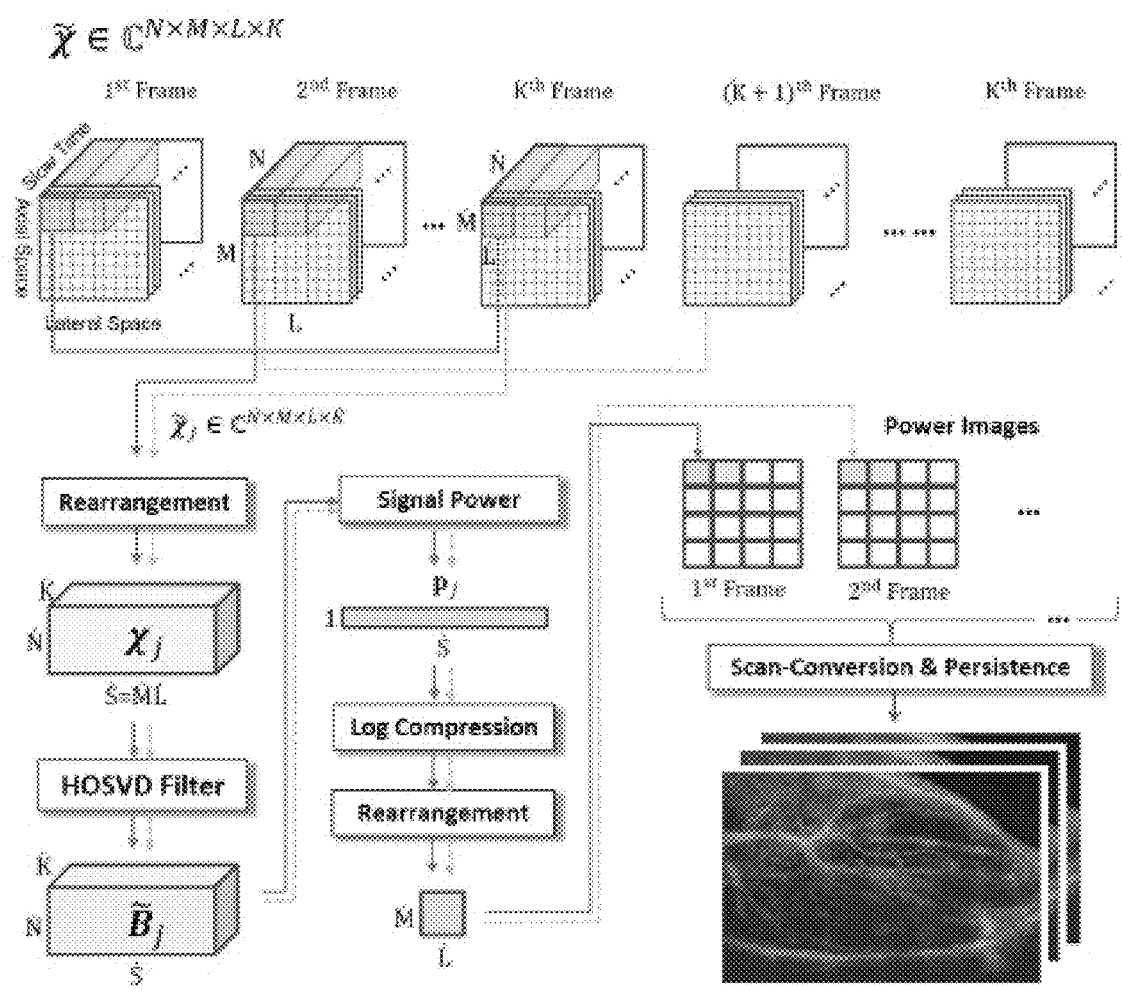
FIG. 4. The sequence of operations leading to the formation of a perfusion image is illustrated. The acquisition data within each window is individually processed. HOSVD filtering isolates the blood-scattering components of the echo signal. Echo power is computed by averaging over slow-time and frame-time axes. The log-compressed power value is assigned a spatial position in the PD image.

Beginning with the 4-D array $X \in \mathbb{C}^{N \times M \times L \times K}$, spatial window $\Omega_j$ of size $N \times M \times \dot{L} \times \dot{K}$ is applied J times to X to make one PD image. Data within the jth window are rearranged into $X_j \in \mathbb{C}^{N \times \dot{S} \times \dot{K}} = \mathbb{C}^{17 \times 224 \times 17}$, where $\dot{S} = M\dot{L}$ for $\dot{M}=14$ and $\dot{L}=16$ samples. Each overlaps adjacent windows by 0.13 mm axially and 0.24 mm laterally. A total of J=1600 spatial windows and filters were applied per 6.4 mm×14.4 mm PD image. We also window data along the frame-time axis if we wish to implement a dynamic sequence of images. FIG. 4 offers a graphical summary. Similar to Eq. (9), the post-filtration signal power within windowed data $B_j \in \mathbb{C}^{N \times \dot{S} \times \dot{K}}$ is computed using $$p_j[i_2] = \frac{1}{N\dot{K}} \sum_{i_1=1}^{N} \sum_{i_3=1}^{\dot{K}} |B_j[i_1, i_2, i_3]|^2, \qquad \text{Equation (16)}$$

where $p_j \in \mathbb{R}^{\dot{S}}$. The elements of vector $p_j$ are log-compressed and scan converted into a spatial segment of size $\dot{M} \times \dot{L}$. These segments are then assembled into a PD image. Final images may sum sequential PD frames formed along the frame-time axis or display them as a dynamic sequence with adjustable persistence. The latter is preferred if perfusion varies over the acquisition time.

In summary, three eigenanalyses are performed on X via Eq. (10). From the three sets of eigenvectors generated, the core tensor is formed via Eq. (13). We then select a region within the core tensor that contains information about perfusion and zero the other elements via Eq. (15). This process yields the perfusion subspace whose elements are squared and summed in Eq. (16) to estimate the signal power mapped into PD images. In vivo experiments below show that the perfusion subspace is confined to a small region within G. Therefore we find it is fast and easy to exhaustively search for values of $c_n$ and $b_n$ in Eq. (15) that yield the "best" perfusion maps shown in the results below.

Appendix A Pulse Sequences

Temporal pulse sampling along a single line of sight is expressed as a continuous-time convolution of two rectangular functions that are sampled by multiplication with comb functions, $\text{comb}(t/T) = T\Sigma_{n=-\infty}^{\infty} \delta(t-nT)$, $$r(t) = \left[\text{rect}\left(\frac{t}{\tau_2}\right) \frac{1}{T_2} \text{comb}\left(\frac{t}{T_2}\right)\right] * \left[\text{rect}\left(\frac{t}{\tau_1}\right) \frac{1}{T_1} \text{comb}\left(\frac{t}{T_1}\right)\right]. \qquad \text{Equation (17)}$$

Figure 37:
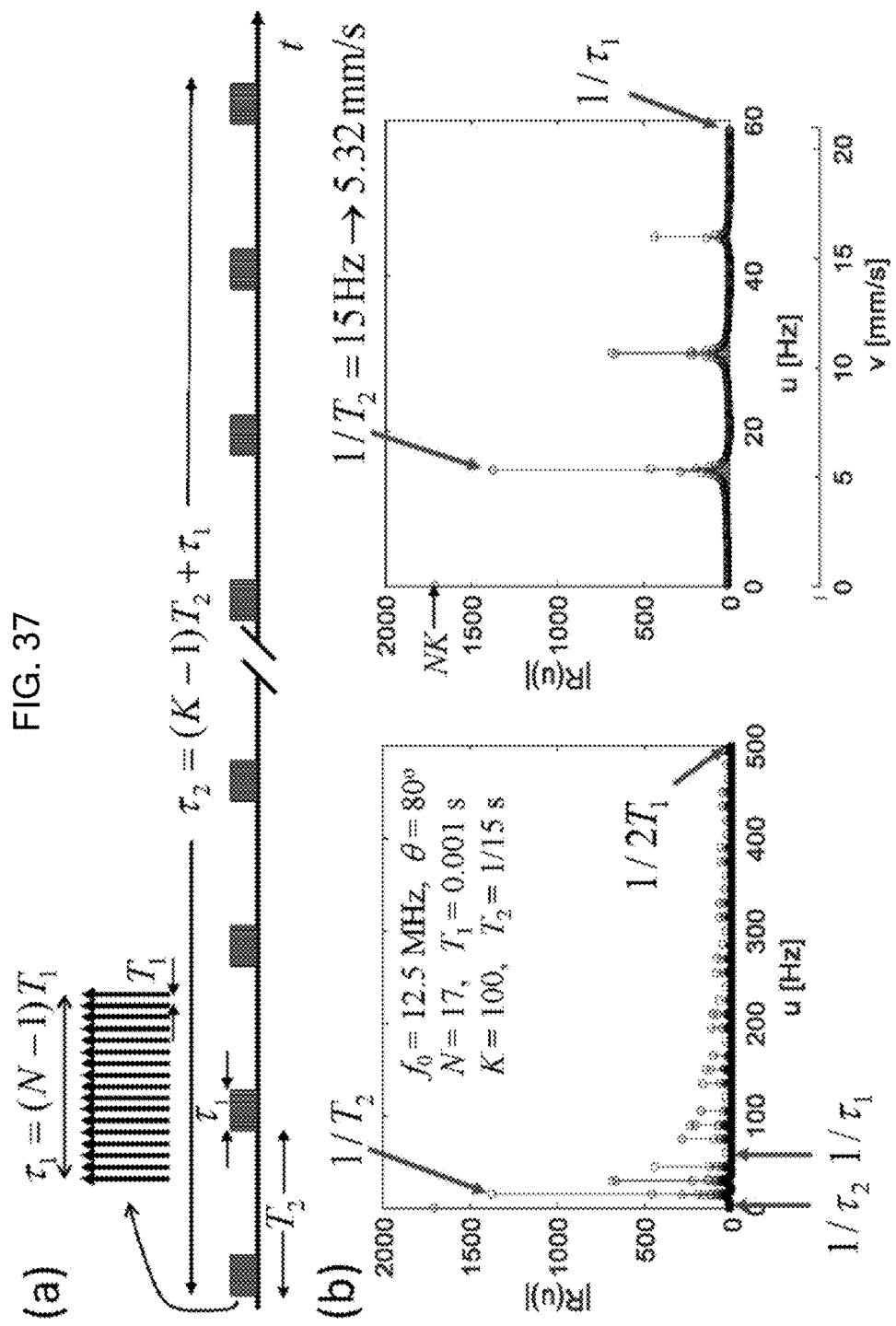
FIG. 37. (a) The temporal pulse sequence r(t) for the 12.5 MHz measurements is sensitive to perfusing RBCs moving at velocities $|\upsilon|<0.6$ mm/s ($|\upsilon|<1.86$ Hz). The echo signal is zero padded 19%. (b) The positive-frequency spectrum $|R(u)|$ in (A2) illustrates sampling along the Doppler frequency axis u for two frequency ranges. Experimental parameters $T_1$; N; $T_2$; K are listed in the figure. The velocity axis $\upsilon$ is found from the u axis via $\upsilon=uc/2f_0 \cos(\theta)=0.323$ u for wave speed c=1.54 mm/µs and Doppler angle θ=79°.

Equation 17 is illustrated in FIG. 37a using parameters of the 12.5 MHz experiment. Note that r(t) is a realignment of the slow-time and frame-time temporal axes in FIG. 24 along a single measurement-time axis, t. One pulse is transmitted at each impulse in r(t), giving NK total pulses along a line of sight. The temporal Fourier transform of r(t) reveals the corresponding sampling in the Doppler frequency domain, $$R(u) = \mathcal{F}\{r(t)\}$$

$$= [\tau_2 \text{sinc}(\tau_2 u) * \text{comb}(T_2 u)][\tau_1 \text{sinc}(\tau_1 u) * \text{comb}(T_1 u)] \qquad \text{Equation (18)}$$

-continued $$= NK \left[ \sum_{n=-\infty}^{\infty} sinc(\tau_2(u-n/T_2)) \right] \left[ \sum_{n=-\infty}^{\infty} sinc(\tau_1(u-n/T_1)) \right]$$

$$= NK \, sinc(\tau_1 u) \left[ \sum_{n=-\infty}^{\infty} sinc(\tau_2(u-n/T_2)) \right] \text{ for } |u| < \frac{1}{2T_1}$$

The limit at $$|u| < \frac{1}{2T_1}$$

in the last line focuses our attention at the spectral frequencies of slow-moving perfusing RBCs.

Equation 18 is illustrated in FIG. 37b.

Converting to a discrete-frequency axis, the frequency (velocity) resolution for 12.5 MHz pulses is nominally $\Delta u = 1/\tau_2 = 0.15$ Hz. ($\Delta \upsilon = 0.05$ mm/s). However we have zero padded the time series 19% so $\Delta u = 1/(1.19\tau_2) = 0.126$ Hz ($\Delta \upsilon = 0.041$ mm/s). Hence, $u[k] = 0.126$ k for $k=0, \pm 1, \pm 2$ .... If no zero padding is applied and we transform a time series with a integer number of frames intervals, e.g., $\tau_2 = KT_2$, the discrete form of (A2) reduces to a sum of Kronecker deltas, $$R[k] = NK \, sinc[(\tau_1/\tau_2)k] \sum_{n=-\infty}^{\infty} \delta[k - Kn]. \qquad \text{Equation (19)}$$

The unpadded sequence has an effective resolution of $(K/\tau_2) = 15$ Hz (4.83 mm/s), leaving one nonzero frequency sample in the range of perfusion imaging, $|\upsilon| < 0.6$ mm/s. Adjusting the zero-pad length, we ensure samples do not just fall at zeros Of the sinc function, as shown on the right side of FIG. 37.

Additional Notation

To distinguish various types of data arrays, the following notation may be used.

1) Scalars can be lower case or capital letters a, b, N, M . . .
2) Column vectors can be bold lower case letters a, b . . .
3) Matrices can be bold capital letters A, B . . .
4) Multidimensional arrays (tensors) can be bold calligraphic capital letters $\mathcal{A}$, $\mathcal{B}$ . . .
5) Array elements: The i th element of vector a can be denoted by $a_i = a[i]$, the (i1, i2)th element of matrix A can be $a_{i1, i2} = A[i1, i2]$, and the (i1, i2, i3)th element of 3D array (for tensor notations, see, e.g., T. G. Kolda and B. W. Bader, "Tensor decompositions and applications," in SIAM Rev., vol. 51, no. 3, pp. 455-500, 2009) A is $a_{i1, i2, i3} = A[i1, i2, i3] = A_{i1, i2, i3}$.

Sets for integers, real numbers, and complex numbers can be represented as Z, R, and C, respectively. For example, $a \in Z_{[0,N]}$ indicates a is an integer scalar and $0 \leq a \leq N$.

Echo Signal Model

First, the spatiotemporal structure of the data array is defined resulting from the narrowband PD acquisition illustrated in FIG. 1. Each beamformed quadrature [in-phase and quadrature (IQ)] echo waveform x(t) is sampled on the fast-time interval T as x(tm) where tm=mT and $m \in Z_{[1,M]}$. M is the number of temporal samples recorded following each pulse transmission. Scaling the time axis, we form the axial waveform $x(z_m) = x(z_0 + ct_m/2)$ where c is the sound speed and $z_0$ is the distance between the transducer surface and the onset of the range gate. Repeatedly transmitting N pulses at each line of site on the slow-time interval T'>MT results in 2D spatiotemporal echo signal $x(t_n, z_m)$, where $t_n = nT'$ and $n \in Z_{[1,N]}$. Scanning laterally, we record L echo lines separated by interval D within each frame. The 3D Doppler frame $x(t_n, z_m, y_l)$ has a slow-time dimension and two spatial dimensions including $y_l$ as the lateral position of the lth echo line; $l \in Z_{[1,L]}$. Finally, K Doppler frames are recorded at frame-time interval T''>T' to form the 4D echo-data array $$\mathcal{X} = x(t_n, z_m, y_l, t_k) \in \mathbb{C}^{N \times M \times L \times K} \qquad \text{Equation (20)}$$

where $t_k = kT''$ and $k \in Z_{[1,K]}$.

Second, we describe a linear model for simulating (1). Echoes from perfused tissues are assumed to arise from discrete RBC and surrounding tissue reflectors, the latter is referred to as tissue clutter. Discrete acquisition time $t = t_{n, m, l, k}$ is the clock time passing during a complete 4D acquisition. Scattering functions $c_i$ (z, y, t) and $b_j$ (z, y, t) define the i th discrete tissue reflector and the j th RBC, respectively, at spatiotemporal location (z, y, t). Furthermore, let h(z, y) be the spatially invariant pulse-echo impulse response of the ultrasonic instrument. Consequently, the echo-data array X can be modeled as a 2D spatial convolution $$X_{n,m,l,k} = \qquad \text{Equation (21)}$$

$$\Gamma \left( \int \int_\Omega dz dy h(z - (z_0 + cmT/2), y - y_l) \times \left[ \sum_{i=1}^{J_c} c_i(z, y, t_{n,m,l,k}) + \sum_{j=1}^{J_b} b_j[z, y, t_{n,m,l,k}] \right] \right) + e_{n,m,l,k}$$

where $\Gamma(\bullet)$ is the operator that converts RF signals to IQ components (see e.g., R. N. McDonough and A. D. Whalen, Detection of Signals in Noise, 2nd ed. San Diego, Calif., USA: Academic, 1995), $\Omega$ is a 2D region indicating the spatial extent of the acquisition (the M and L dimensions in FIG. 1), and $J_c$ and $J_b$ are the number of discrete tissue and blood scatterers, respectively, in a $\Omega$. Also, e is additive white-Gaussian acquisition noise. Equation (21) is more simply expressed as the sum of three 4D arrays describing clutter C, blood B, and noise N sources via $$\mathcal{X} = \mathcal{C} + \mathcal{B} + \mathcal{N}. \qquad \text{Equation (22)}$$

Ratios of signal power between the contributing sources are $$\begin{cases} r_{CB} = 10 \log_{10}(\|\mathcal{C}\|^2 / \|\mathcal{B}\|^2) \\ r_{BN} = 10 \log_{10}(\|\mathcal{B}\|^2 / \|\mathcal{N}\|^2) \end{cases} \qquad \text{Equation (23)}$$

where $\|\bullet\|$ indicates the $l_2$-norm and $r_{CB}$ and $r_{BN}$ are clutter-to-blood and blood-to-noise ratios, respectively, each expressed in decibels, Tissue and Blood Motion The i th tissue scatterer randomly positioned in $\Omega_c \in \Omega$ (see FIG. 2) is represented by the Dirac delta $$c_i(z,y,t)=\alpha_c^{(i)}\delta(z-(z_{c0}+z_c(t))^{(i)}, y-(y_{c0}+y_c(y))^{(i)}) \quad \text{Equation (24)}$$

where $\alpha_c^{(i)} \sim N(m_{\alpha_c}, \sigma_{\alpha_c}^2)$ is a normally distributed echo amplitude assigned to the ith tissue scatterer, and $(z_{c0}^{(i)}, y_{c0}^{(i)}))$ is its position in $\Omega_c$ at t=0. Tissue displacement vector $f_c(t)$, which applies at t>0, describes the temporal movements of all tissue scatterers in relative to the initial positions. It includes the sum of 2-D breathing $\eta(t)$ and muscle vibration $\xi(t)$ vectors $$f_c^{(i)}(t) = (z_c(t), y_c(t))^{(i)} = \eta(t) + \xi(t) \text{ for } t>0$$

and where $$\begin{cases} \eta(t) = \beta\left[\sum_{n'} e^{\frac{-(t-n'\Delta t)^2}{2\sigma_r^2}}, 0\right] \\ \xi(t) = \gamma \sin(\omega_0 t)[\cos(\theta), \sin(\theta)]. \end{cases} \quad \text{Equation (25)}$$

Symbol n' is an integer, $\Delta t$ indicates the interval between breaths, and $\beta$ and $\sigma_r$ specify the range and rate of breathing movement oriented along the z-axis. Parameters $\gamma$, $\omega_0$, and $\theta$ determine the oscillation strength, frequency, and direction, of muscle vibration. The directions of the two sources of clutter movement are neither aligned to each other nor they are synchronous, although each function is applied simultaneously to all scatterers in $\Omega_c$.

Similarly, the position of the jth RBC is $$b_j(z,y,t)=\alpha_b^{(j)}\delta(z-(Z_{b0}+Z_{b(t)})^{(j)}, y-(y_{b0}+y_b(t))^{(j)}) \quad \text{Equation (26)}$$

where the RBC echo amplitude is $\alpha_b^{(j)} \sim N(m_{\alpha_b}, \sigma_{\alpha_b}^2)$ and $(z_{b0}^{(j)}, y_{b0}^{(j)})$ is the initial position within $\Omega_b \in \Omega$.

Blood displacement vector $f_b^{(j)}(t) = (z_b^{(j)}(t), y_b^{(j)}(t))$ describes the temporal movement of the jth RBC at times t>0 relative to its initial position. RBC movement is also modeled as the sum of two 2-D vector sources $$f_b^{(j)}(t) = \eta(t) + \zeta^{(j)}(t) \text{ for } t>0$$

where $$\zeta^{(j)}(t) = t[|\upsilon^{(j)}| \sin \varphi^{(j)}, |\upsilon(j)| \cos \varphi(j)]. \quad \text{Equation (27)}$$

The speed $|\upsilon(j)|$ and the Doppler angle $\varphi^{(j)}$ are constant in| time but vary spatially within Q as illustrated, e.g., by the vascular patterns in FIG. 2. Since respiration is a rigid-body translation of vessels with the surrounding tissues, $\eta(t)$ is the same as that given in (6).

Equations (25) and (27) update (24) and (26) at each time interval. The results of (24) and (26) are summed in (21) and convolved with impulse response h(z, y) to simulate RE echo signals. In this study, h(z, y) is a shift invariant, 2-D Gaussian pulse with sinusoidally modulated amplitude along the z-axis. The IQ components of the RF echo signals composing the 4-D complex-valued array $\mathcal{X}_{n,m,l,k}$ are found by demodulating the analytic RF echo signals, as shown in (21).

Decomposition of Data Array

The slow-time dimension of the data array can be sensitive to vascular flows.

The slow-time dimension of data array $\mathcal{X}$, with values sampled on the order of kilohertz, is most sensitive to echoes from fast vascular flows. Its frame-time dimension, sampled on the order of hertz, is most sensitive to slow spatially incoherent perfusion echoes. The two spatial dimensions provide essential information about the spatiotemporal heterogeneity of primarily tissue echoes. Both the spatial axes can be reordered into a single array axis dimension for the purpose of building a clutter filter. We do this by applying lexicographic transformation operator $\Psi$, resulting in $$\tilde{\mathcal{X}} = \Psi(\mathcal{X}), \text{ such that } \tilde{x}_{n,s,k} \times x_{n,m,l,k} \quad \text{Equation (28)}$$

where $\tilde{\mathcal{X}} \in \mathbb{C}^{N \times S \times K}$, s=m+(l−1)M, and S=ML, Data array X can be decomposed using HOSVD. Reducing the data array from 4D to 3D reduces the HOSVD compute time.

Figure 3:
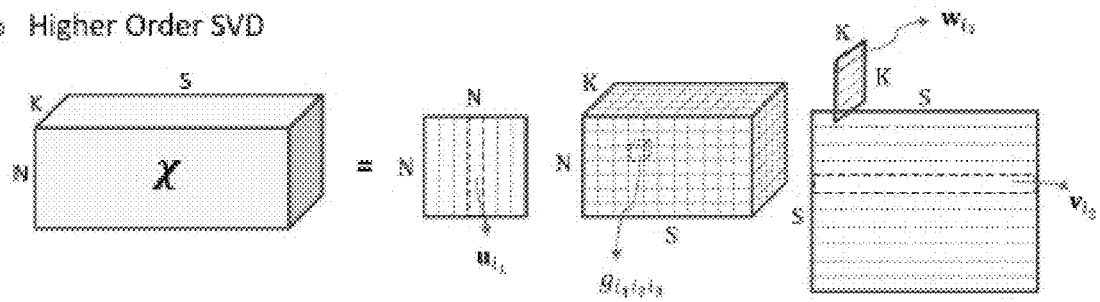
FIG. 3. The top diagram describes HOSVD applied to 3rd-order tensor data X. The bottom diagram illustrates a region in the core tensor being selected to isolate the blood-perfusion signal.
Figure 3:
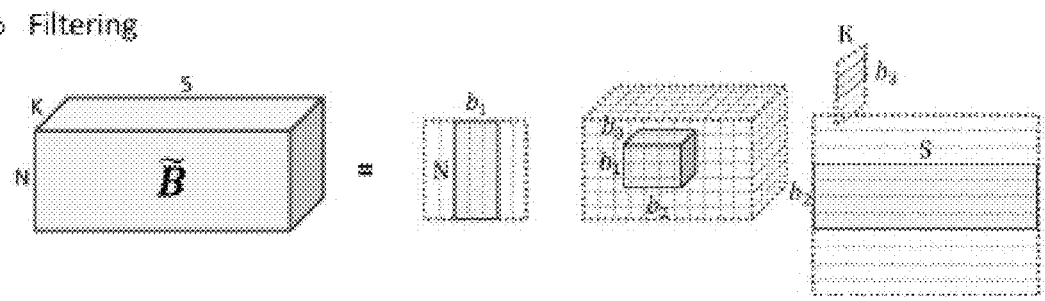

HOSVD is a multilinear generalization of 2D SVD analysis. As shown in FIG. 3, decomposing data array X generates core tensor[1] $\mathcal{G} \in \mathbb{C}^{N \times S \times K}$ with core elements $g_{i_1 i_2 i_3}$ and three orthogonal matrices: $U \in \mathbb{C}^{N \times N}$ whose columns u are slow-time-mode eigenvectors, $V \in \mathbb{C}^{S \times S}$ whose columns v are spatial-mode eigenvectors, and $W \in \mathbb{C}^{K \times K}$ whose columns w are frame-time-inode eigenvectors. The expression can be written

[1] Modal planes in $\mathcal{G}$ are orthogonal; i.e., $\Sigma_{i_1} \Sigma_{i_2}$ gi$_1$, i$_2$, a gi$_1$, i$_2$ b=$\Sigma_{i_1} \Sigma_{i_3}$ gi$_1$, a, i$_3$, gi$_1$, b, i$_3$=$\Sigma_{i_2} \Sigma_{i_3}$ ga, i$_2$, i$_3$, gb, i$_2$, i$_3$=0 unless a=b.

$$\tilde{X} = \mathcal{G} \times_1 U \times_2 V \times_3 W \quad \text{Equation (29)}$$

$$= \sum_{i_1=1}^{N} \sum_{i_2=1}^{S} \sum_{i_3=1}^{K} g_{i_1,i_2,i_3} u_{i_1} \times v_{i_2} \times w_{i_3}$$

where $\times_n$ denotes n-mode outer product. The eigenvalues for each of the three modes are given as $$\begin{cases} \text{Slow-time mode:} & \lambda_{j_1}^{(1)} = \sum_{i_2=1}^{S} \sum_{i_3=1}^{K} |g_{j_1,i_2,i_3}|^2 \\ \text{Spatial mode:} & \lambda_{j_2}^{(2)} = \sum_{i_1=1}^{N} \sum_{i_3=1}^{K} |g_{i_1,j_2,i_3}|^2 \\ \text{Frame-time mode:} & \lambda_{j_3}^{(3)} = \sum_{i_1=1}^{N} \sum_{i_2=1}^{S} |g_{i_1,i_2,j_3}|^2. \end{cases} \quad \text{Equation (30)}$$

Eigenvalues for each mode are arranged in decreasing order.

The main interest is to preserve echo signals originating from blood perfusion while suppressing other echo signal contributions. The echo data can be filtered by identifying the 3D subspace in $\mathcal{G}$ dominated by perfusion echoes and suppressing values outside the perfusion subspace. Since signal power from clutter, blood, and acquisition-noise sources can occupy the same subspace, the filtering process is not straightforward.

Clutter Filtering

The strategy is to classify each core element ($i_1$, $i_2$, $i_3$) as clutter or non-clutter based on one or more of five features described in the following Elements identified as "clutter dominant" are discarded.

Figure 15:
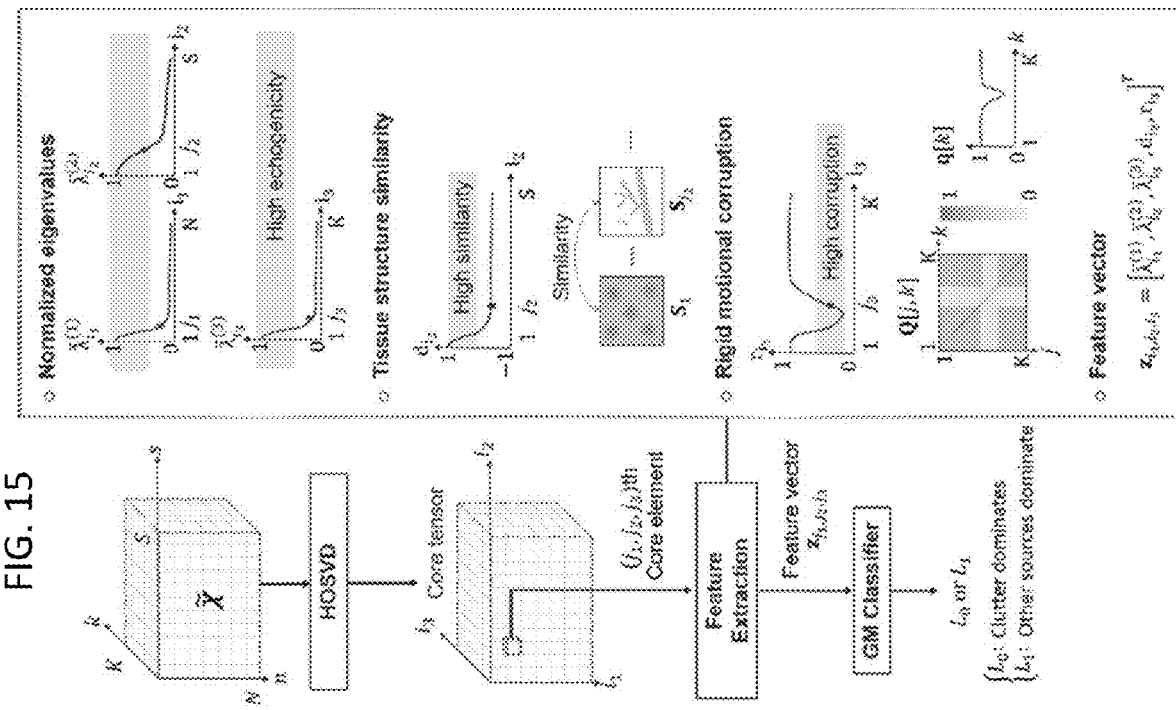
FIG. 15. Classification of each eigenelement for clutter filtering. To determine the state of (j1, j2, j3)th core element, features are extracted from eigenvectors and eigenvalues. Normalized eigenvalues are associated with source echogenicity. The eigen image using spatial eigenvector provides structural information as shown in FIG. 6. Provided that first eigen image $S_1$ most likely involves tissue structure, the correlation between the first image and j2th image informs the contribution of the j2th eigenspace for tissue clutter. The last feature is associated with strong rigid motion. Data acquired for the moment tend to be corrupted by strong clutter. The time points can be recognized by similarity matrix Q obtained by computing the correlation between frame images. The feature measures the contribution of the j3th eigenspace for the time points (corruption). The GM classifier makes a decision using the features.

1) Feature Selection:
a) Normalized Eigenvalues: Three of the five features are from the normalized eigenvalue spectra. The slow-time eigenvalue spectrum is normalized using $$\bar{\lambda}_{i_1}^{(1)} = \frac{\log_{10} \lambda_{i_1}^{(1)} - \log_{10} \lambda_{min}^{(1)}}{\log_{10} \lambda_{max}^{(1)} - \log_{10} \lambda_{min}^{(1)}} \in \mathbb{R}_{[0,1]} \quad \text{Equation (31)}$$

where $\lambda_{max}^{(1)} = \lambda_1^{(1)}$ and $\lambda_{min}^{(1)} = \lambda_N^{(1)}$. Similarly, the normalized spatial and frame-time eigenvalue spectra are $\bar{\lambda}_{i_2}^{(2)}$ and $\bar{\lambda}_{i_3}^{(3)}$, respectively. In each normalized spectrum, the first value is largest and equal to 1. When the clutter is significant, subsequent spectral values at $i_1, i_2, i_3 > 1$ associated with clutter remain close to 1 (FIG. 4, top right). Large eigenvalues arise from the most echogenic components of $\tilde{\mathcal{X}}$ that are typically associated with stationary or rigid-body tissues dynamics.

b) Tissue Structure Similarity: The magnitude of each spatial eigenvector, $s_{i_2} = |v_{i_2}| \in R^{S \times 1}$, which are columns of V, can be reformatted into a 2-D image $S_{i_2} \in R^{M \times L}$. Eigen image $S_1$ is associated with the largest (first) eigenvalue. It resembles the B-mode image for the region of interest. Other eigen images from V which are influenced by tissue clutter will have similar structural patterns. In contrast, eigen images most influenced by blood signals or noise will be appear dissimilar to $S_1$. The fourth feature, d, compares the first eigen image with each of the others using Pearson's correlation coefficient via operator $Y(\bullet)$ to quantify similarity $$d_{i_2} = Y(s_1, s_{i_2}) \quad \text{Equation (32)}$$

$$= \frac{\sum_{n=1}^{S}(s_1[n] - \bar{s}_1)(s_{i_2}[n] - \bar{s}_{i_2})}{\sqrt{\sum_{n=1}^{S}(s_1[n] - \bar{s}_1)^2} \sqrt{\sum_{n=1}^{S}(s_{i_2}[n] - \bar{s}_{i_2})^2}}$$

where $d_{i_2} \in \mathbb{R}_{[-1,1]}$, and $\bar{s}_1$, $\bar{s}_{i_2}$, art the means of all samples in vectors $s_1$, $s_{i_2}$. Large positive d values indicate core elements with significant clutter contributions to $\tilde{\mathcal{X}}$ (see FIG. 15, right).

c) Rigid-Body Motion Corruption: Adding a frame axis to extend the echo-data array enhances the sensitivity to both the blood perfusion and the moving tissue clutter. The magnitude of motion over the frame-time axis is identified by comparing echo power images obtained from the kth Doppler frame using $$P_k[m,\ell] = 10\log_{10}\left(\frac{1}{N}\sum_{n=1}^{N}|X[n,m,\ell,k]|^2\right). \quad \text{Equation (33)}$$

The similarity between the echo power in two frames is $$Q[j,k] = Y(P_j, P_k) \quad \text{Equation (34)}$$

where matrix $Q \in \mathbb{R}^{K \times K}$. The sudden, large-amplitude, coherent motion characteristic of clutter creates distinct patterns in Q (see FIG. 4, right) where echo power is far less correlated. Negative correlations are possible, but, in practice, correlations from rigid-body motion remain positive. The mean correlation between the kth and jth frames is $$q[k] = \frac{1}{K}\sum_{j=1}^{K} Q[j,k] \in \mathbb{R}_{[0,1]}. \quad \text{Equation (35)}$$

Large coherent displacements, like those from breathing, result in small correlation values. Vector q can thus be used as a basis to test if a frame is corrupted by clutter motion. The inner product $$r_{i_3} = \sum_{k=1}^{K} q[k]|w_{i_3}[k]|^2 \in \mathbb{R}_{[0,1]} \quad \text{Equation (36)}$$

provides r, a scalar feature quantifying motion corruption in a data frame. Note that $|w_{i_3}[k]|^2$ results from a Hadamard (elementwise) product of $w_{i_3}$ with itself. Small values of r indicate a frame is corrupted by coherent motion.

Each core tensor element is classified based on the feature vector z computed for that element, from Equations (31), (32), and (36)

$$z_{i_1,i_2,i_3} = [\bar{\lambda}_{i_1}^{(1)}, \bar{\lambda}_{i_2}^{(2)}, \bar{\lambda}_{i_3}^{(3)}, d_{i_2}, r_{i_3}]^T. \quad \text{Equation (37)}$$

2) GM Classifier: Each core element can be classified as clutter dominated $L_0$ or nonclutter dominated $L_1$ using the following likelihood ratio test classifier:

$$D(z) = \begin{cases} L_0, & \text{if } p(z|L_0)/p(z|L_1) > \tau \\ L_1, & \text{if } p(z|L_0)/p(z|L_1) \leq \tau. \end{cases} \quad \text{Equation (38)}$$

Threshold depends on error risks, which can be determined once the clinical risk is defined. $p(z|L_0)$ and $p(z|L_1)$ are probability density functions (pdfs) conditioned on states $L_0$ and $L_1$, viz., $p(z|L_i) \sim \text{Normal}(\bar{z}_i, \Sigma_i)$, $i \in \{0, 1\}$. We will show that both pdfs are found by applying training data.

From simulated echo data with known states, likelihood functions are modeled as linear mixtures of three multivariate Gaussian functions [Gaussian mixture (GM) models]

$$p(z|L_i) = \sum_{j=1}^{3} A_{ij} \frac{1}{\sqrt{(2\pi)^3|\Sigma_{ij}|}} e^{\left(-\frac{1}{2}(z-\bar{z}_{ij})^2 \Sigma_{ij}^{-1}(z-\bar{z}_{ij})\right)} \quad \text{Equation (39)}$$

where $z^\dagger$ is the conjugate transpose of z. Amplitudes $A_{ij}$, mean vectors $\bar{z}_{ij}$, and covariance matrices $\Sigma_{ij}$ are for the ith state and the jth (of three) mixture model functions. A three-component mixture model was found to provide an acceptable compromise between the model accuracy and the computation time as discussed in Section III-A.

3) Training for perfusion data

3) Training: Simulated echo signals are computed from training media similar to the perfused tissue regions illustrated in FIGS. 1 and 2. First, we set the blood and noise terms to zero in (2) to compute the clutter-only component, $C \in \mathbb{C}^{N \times M \times L \times K}$ reformat the result via (9) to find $\bar{C} \in \mathbb{C}^{N \times S \times K}$. Next, (2) is applied to the same model, now including all scattering components, to simulate perfusion data $\tilde{\mathcal{X}}$ with clutter and noise. The 4-D array is reformatted to find $\mathcal{G} \in \mathbb{C}^{N \times S \times K}$ and decomposed with HOSVD to compute core tensor $\tilde{\mathcal{X}} \in \mathbb{C}^{N \times S \times K}$. Rectangular subspaces within $\mathcal{G}$ of increasing size, beginning with element $i_1 = i_2 = i_3 = 1$ and growing to $i_1 = N$, $i_2 = S$, $i_3 = K$, are progressively selected to form all possible estimates of clutter subspace $\hat{\mathcal{G}}_C$. Core elements outside the selected regions are set to zero. Reconstructing the echo data matrix from (10), but using $\hat{\mathcal{G}}_C$ in place of $\mathcal{G}$, we estimate the clutter-only signal, $\hat{c}$. Subspace $\hat{\mathcal{G}}_C$ giving clutter echo signal estimate $\hat{c}$ that most closely matches the known clutter-only signal $\tilde{c}$ becomes the final subspace estimate, $\mathcal{G}_C$. The objective function is $$\mathcal{G}_C = \arg\min_{\hat{\mathcal{G}}_C} \|\tilde{\mathcal{C}} - \hat{\mathcal{C}}\|^2$$

$$\text{w.r.t.} \begin{cases} \hat{\mathcal{C}} = \sum_{(i_1,i_2,i_3)\in\hat{\mathcal{G}}_C} g_{i_1,i_2,i_3} u_{i_1} \times v_{i_2} \times w_{i_3} \\ \hat{\mathcal{G}}_C = \{\forall\, (i_1, i_2, i_3) \mid 0 < i_1 < c_{i_1}, 0 < i_2 < c_{i_2}, 0 < i_3 < c_{i_3}\}. \end{cases}$$

The feature vectors for core elements within $\mathcal{G}_C$ are labeled $L_0$, others are labeled $L_1$. Training results in a hard threshold being set for subspace parsing.

4) Testing

4) Testing: With the knowledge of the clutter subspace from (21), we can estimate the parameters in (20). Specifically, equivalent Matlab R2015b functions "gmdistribution.fit" or "fitgmdist" apply the expectation-maxiraization algorithm to find maximum-likelihood estimates of the three-component GM model parameters, $A_{ij}$, $\bar{z}_{ij}$, and $\Sigma_{ij}$. Finally, combining (19) and (20), we are now prepared to simulate the test data (independent of the training data) to test this clutter filter. First, we discuss a method for filtering acquisition noise.

Noise Filtering

Several techniques for suppressing additive white-Gaussian noise in a data array have been thoroughly studied [21]-[23]. Following clutter filtering, the noise-filtering approach we adopt is to find the blood-signal rank for the correlation matrix of each data-array mode, $r_i$, and to zero eigenvalues beyond $r_i$. In a tensor model, the blood-signal rank can be different for the slow-time, spatial, and frame-time correlation matrices. We adopt a minimum description length method for estimating the blood-signal rank of each matrix. For example, the rank of the slow-time correlation matrix can be estimated as $$r_1 = \arg\min_r -2\log\left\{\frac{\left(\prod_{i=r+1}^{N} [\lambda_i^{(1)}]^{1/(M-r)}\right)^{SK(M-r)}}{\frac{1}{M-r}\sum_{i=r+1}^{M} \lambda_i^{(1)}}\right\} + \quad\text{Equation (41)}$$

$$r(2M - r)\log(SK).$$

Similarly, we estimate $r_2$ and $r_3$. Data are noise filtered by discarding the noise-dominated subspace using the hand threshold $\mathcal{G}_N = \{i_1, i_2, i_3 \mid (i_1 > r_1) \lor (i_2 > r_2) \lor (i_3 > r_3)\}$ where $\lor$ indicates logical "or." What remains is ale blood subspace $\mathcal{G}_B$.

Velocity Discrimination

We found that the slow-time eigenvector can be used to parse speed ranges for blood components of the postfiltered echo signal. The frequency spectrum of each of eigenvector is found using the discrete Fourier transform expression $$U[k] = \left|\frac{1}{N}\sum_{n=1}^{N} u_{i_1}[n] \exp(-i2\pi nk/N)\right| \quad\text{Equation (42)}$$

where $u_{i_1}[n]$ is a nth element of eigenvector $u_{i_1}$. The slow-time frequency $f=k/NT'$ is converted into the axial component of blood speed $\upsilon$ using the Doppler equation $\upsilon=cf/2f_c$, where c and $f_c$ are the wave speed and the pulse center frequency, respectively. The weight indicating contributions to the eigenvector from the speed range $[\upsilon_{min}, \upsilon_{max}]$ is found from $$\omega_{i_1} = \sum_k U[k]\omega[k] \quad\text{Equation (43)}$$

$$\omega[k] = \begin{cases} 1, \text{ if } \upsilon_{min} < \left|\frac{cf}{2f_c}\right| < \upsilon_{max} \\ 0, \text{ otherwise.} \end{cases}$$

The weight is used to apply a soft-threshold in the slow-time mode.

Velocity discrimination combined with clutter and noise suppression yields an estimate of the target blood-echo signal $$\hat{\mathcal{B}} = \sum_{(i_1,i_2,i_3)\in\mathcal{G}_B} g_{i_1,i_2,i_3}(\omega_{i_1} u_{i_1}) \times v_{i_2} \times w_{i_3}. \quad\text{Equation (44)}$$

Filter Scale

Echo frames up to several square centimeters in the area can be recorded for as long as 10 seconds, or up to 30 seconds, to capture the blood perfusion patterns. Because tissue sample are heterogeneous, the data arrays can be divided into statistically homogeneous blocks that may overlap, and a filter can be applied for each.

The jth of J data blocks is expressed as $\mathcal{X}_j \in \mathbb{C}^{\dot{N}\times\dot{M}\times\dot{L}\times\dot{K}}$, where $\dot{N}<N$, $\dot{M}<M$, $\dot{L}<L$, and $\dot{K}<K$. Each block is reshaped into $\tilde{\mathcal{X}}_j \in \mathbb{C}^{\dot{N}\times\dot{S}\times\dot{K}}$, where $\dot{S}=\dot{M}\dot{L}$, and individually processed via HOSVD. The subspace selection for the jth filter is determined only by the statistical characteristics of data in that block.

Methods for Experimental Validation of Perfusion Imaging

A. Echo-Data Array Structure and Filtering for PD Imaging

Each Doppler frame is recorded as complex IQ echo samples and as a function of two spatial axes (axial and lateral) and one temporal axis (slow-time) as shown in FIG. 1. N slow-time samples are acquired at pulse-repetition rate $1/T_1$. A linear array records a region of interest composed of L parallel pulse-echo scan lines each with M axial samples. The 3-D data array for a recorded frame is $\tilde{X}\in\mathbb{C}^{N\times M\times L}$.

We only preserve those data-array dimensions for HOSVD processing that provide some unique signature useful for parsing core-tensor subspaces. Not finding that axial and lateral spatial features are reliably distinctive, we reorder the two spatial axes into one: $\tilde{x}_{n,m,l} \to x_{n,s}$ where $s \triangleq m+(l-1)M$, and $S \triangleq ML$. Expressing each Doppler frame in 2-D as $X\in\mathbb{C}_{N\times S}$ retains the spatial context of any echo information that survives altering. This is the Casorati matrix processed when developing 2-D SVD clutter filters.

We add a third dimension to the data array that is composed of K frames acquired at frame-repetition rate $1/T_2$, yielding $X \in \mathbb{C}^{N \times S \times K}$.

Echo-sample statistics can be non-stationary; e g perfusion can be patchy and temporally fluctuating in ischemic skeletal muscle. Subregions within X can be found that are scrolled along the spatial and frame-time axes, $\dot{X} \in \mathbb{C}^{N \times \dot{S} \times \dot{K}}$, as shown on the right side of FIG. 24. In this way, the clutter filter is both spatially and temporally adaptive.

Applying adaptive 3-D SVD to $\dot{X}$ we generate one core tensor $\dot{\mathcal{G}}$ with elements $g_{n,s,k}$, and eigenvector matrices U, V, and W for each tissue subregion [1], [2]. The nth column of N×N matrix U is the nth slow-time eigenvector $u_n$. Similarly for V and W. The data synthesis equation is $$\dot{X} = \sum_{n=1}^{N} \sum_{s=1}^{\dot{S}} \sum_{k=1}^{\dot{K}} g_{n,s,k} u_n \times v_s \times w_k, \quad \text{Equation (45)}$$

where $u_n \times v_s$ is the outer product of the two vectors.

Filtering requires that we identify for each subregion those core-tensor elements $g_{n,s,k}$ that constitute the blood subspace $\dot{\mathcal{G}}_B$; i.e., elements attributed to echoes from perfusing RBCs. The non-blood singular values are suppressed before echo data are synthesized using $$\dot{X}_B = \sum_{(n,s,k) \in \dot{\mathcal{G}}_B} g_{n,s,k} u_n \times v_s \times w_k. \quad \text{Equation (46)}$$

These filtered echo data are further processed to generate power-Doppler (PD) or color-flow (CF) images via standard techniques [12]. For example, the sth pixel of a PD images is found using the following equation:

$$PD(s) = \frac{1}{N\dot{K}} \sum_{n=1}^{N} \sum_{k=1}^{\dot{K}} |\dot{X}_B(n, s, k)|^2. \quad \text{Equation (47)}$$

B. Phantom Study

Figure 25:
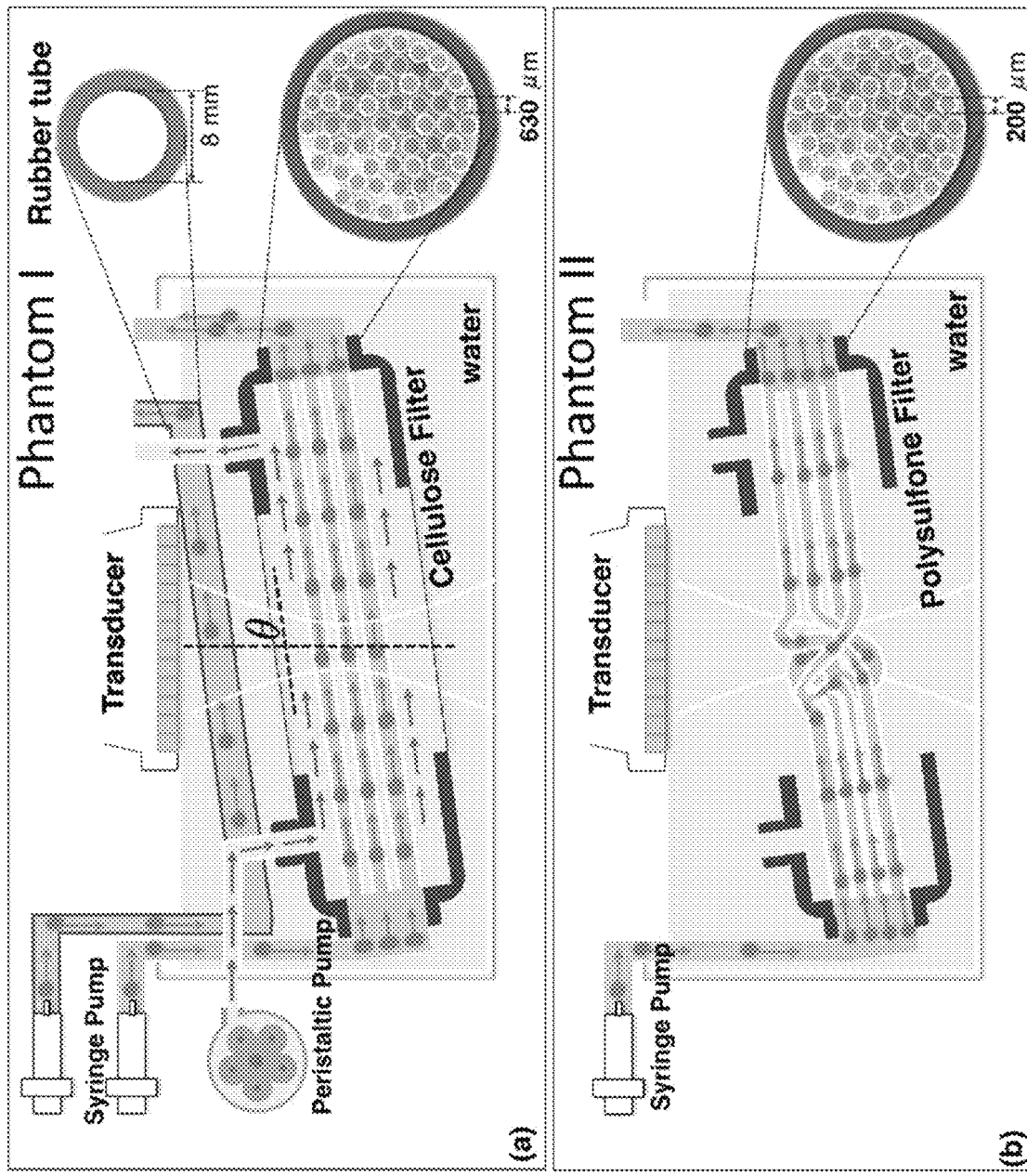
FIG. 25. Two phantoms with different dialysis-cartridge filters were used as perfusion flow phantoms. Both are positioned inside a water tank where a linear array transducer scans from above. A programmable syringe pump injects either degassed water or TM blood into the fibers of the dialysis cartridges at constant flow rate. (a) Phantom I provides directional flow with fibers oriented at a Doppler angle θ=79°±4°. An 8-mm inner diameter latex tube is place above the dialysis cartridges at the same Doppler angle. A portion of the plastic cartridge outer cylinder was removed and covered with paraffin film to form an acoustic window. A peristaltic pump injects water pulses between the fibers and cartridge outer cylinder to create pulsatile clutter motion. (b) Phantom II has a central band of plastic removed from the casing and the two ends pushed together and twisted so the fibers formed a disorganized flow pattern. Moving external clutter was generated by tapping the water tank.

Renal dialysis cartridges were adapted for experiments with vascular-like and perfusion-like flow geometries. The goal was to produce a variety of known flow conditions such that measurement errors associated with fast and slow-speed flows could be assessed using both color-flow and power-Doppler techniques. Details of two phantoms are illustrated in FIG. 25. A calibrated syringe pump determined the net flows. The fluid was either water (control measurements) or tissue-mimicking (TM) blood (CIRS, Norfork, Va. USA); stationary or moving clutter were also present.

1) Phantom I: FIG. 25a illustrates the experiment to test measurements for directional slow-flow geometries. This dialysis cartridge (Spectrum Laboratories Inc., Rancho Dominguez, Calif. USA) contained a bundle of 20 cm-long cellulose fibers with inner and outer diameters 0.63 mm and 0.87 mm, respectively. We cut 6 cm holes into opposing sides near the center of the thick plastic cartridge housing and covered them with paraffin film (Parafilm, Bemis Co. Inc., Neenah Wis., USA) before submerging them in degassed water.

Moving clutter echoes were introduced using a peristaltic pump that injected periodic water pulses at 0.16 Hz into the cartridge outside the flow fibers. The labels 'stationary' or 'moving' clutter in the results indicated the peristaltic pump was turned off or on, respectively. To test the ability of our clutter filters to separate directional flow in a large vessel from directional perfusion, we added an 8 mm diameter thin-walled rubber tube above or alongside the cartridge filter.

2) Phantom II: FIG. 25b illustrates a second experiment, where the dialysis cartidge (B. Braun Medical Inc., Allentown, Pa., USA) contained a bundle of 0.2 mm-diameter flexible polysulfone fibers. We removed an entire band of housing plastic so we could twist and push the cartridge ends together to create a region of nondirectional perfusion-like flow. The peristaltic pump cannot generate moving clutter under these conditions, so clutter movement was generated by tapping the water tank at 0.5 Hz. Polysulfone fibers are more acoustically attenuating than cellulose fibers, but more flexible as needed to simulate non-directional perfusion-like flow.

Both phantoms were scanned with a Vevo 2100 ultrasound imaging system transmitting 12.5 MHz Doppler pulses (FUJIFILM VisualSonics Inc. Toronto, Ontario, Canada) and a Sonix RP system transmitting 5 MHz Doppler pulses (Ultrasonix Medical Corp., Richmond, BC, Canada). The flow rate of the blood-mimicking fluid varies from 0 mL/min to 4 mL/min and the flow direction was reversible. Phantom and experimental acquisition parameters are summarized in Tables 1 and 2, respectively.

TABLE 1

Flow Phantom Parameters

| Parameter | Value |
|---|---|
| Control fluid | degassed water |
| Perfusion fluid | TM blood |
| Flow rate range | 0-4 mL/min |
| Clutter Motion Level 0 | no motion |
| Clutter Motion Level 1 | rotation freq 0.16 Hz |
| Tapping motion clutter | 0.5 Hz |
| Phantom I fiber length | 200 mm |
| Phantom I passing time @ 2 mL/min | 5'5"-5'30" ($\bar{v}'$ = 0.61-0.65 mm/s) |
| Phantom I fiber bundle diameter | 10-12 mm |
| Phantom I fiber inner/outer diameters | 0.63/0.87 mm |
| Phantom II fiber inner diameter | 0.20 mm |
| Phantom II fiber bundle diameter | 60 mm |
| Doppler angle (θ) | 75-83° |

TABLE 2

Acquisition Parameters

| | Vevo 2100 | Sonix RP |
|---|---|---|
| Probe | MS-200 | L14-5 |
| Pulse center frequency ($f_0$) | 12.5 MHz | 5 MHz |
| Slow-time sampling rate ($1/T_1$) | 1 kHz | 1 kHz |
| Slow-time ensemble size (N) | 17 (0.017 s) | 12 (0.012 s) |
| Frame-time sampling rate ($1/T_2$) | 15 Hz | 20 Hz |
| Frame-time ensemble size (K) | 100 (6.7 s) | 130 (7.5 s) |
| Fast-time sample rate (1/T) | 12.5 Ms/s | 20 Ms/s |
| Axial samples/frame (M) | 248 (15.3 mm) | 448 (17.2 mm) |
| Lateral sample/frame (L) | 53 (13.2 mm) | 78 (29.6 mm) |
| Scan-line density | 402 lines/mm | 2.63 lines/mm |
| Spatial samples (S = LM) | 13144 | 34944 |
| Axial sub-block size ($\dot{M}$) | 50 (3.1 mm) | 80 (3.1 mm) |
| Lateral sub-block size ($\dot{L}$) | 30 (7.5 mm) | 20 (7.6 mm) |
| Frame-time sub-block ($\dot{K}$) | 30 (2.0 s) | 40 (2.0 s) |

Both phantoms were scanned with a Vevo 2100 ultrasound imaging system transmitting 12.5 MHz Doppler pulses (FUJIFILM VisualSonics Inc. Toronto, Ontario, Canada) and a Sonix RP system transmitting 5 MHz Doppler pulses (Ultrasonix Medical Corp., Richmond, BC, Canada). The flow rate of the blood-mimicking fluid varies from 0 mL/min to 4 mL/min and the flow direction was reversible. Phantom and experimental acquisition parameters are summarized in Tables 1 and 2, respectively.

C. Flow Speed Estimation

Traditionally, peripheral perfusion may be assessed using ultrasonic PD methods because the slow, non-directional movement of RBCs in the microvasculature may best captured by the net echo power after clutter and noise filtering. Nevertheless, in this section we describe experiments aimed at estimating the speed of TM blood flow in phantom 1 via the spectral centroid. Slow directional flow in phantom fibers offers an opportunity to quantitatively validate our techniques, including the effectiveness of clutter filtering. Using a stopwatch and knowledge of the dialysis-cartridge fiber length, we measured the time of fluid transport through the fibers to estimate the spatial mean velocity for TM blood fluid, $\bar{v}'$ (Table 1).

Acquiring and filtering echo data from phantom 1, we obtain $\dot{X}_B(n, s, k)$ via Eq. (2). We select echo samples following the n=1 pulse transmission within each Doppler frame k at all spatial locations s in the region (see FIG. 1). We then compute the magnitude of the Fourier transform along the frame-time axis (k index). $|\mathcal{F}_k\{\dot{X}_B(n, s, k)\}|$. This process is repeated for all N pulses in the slow-time ensemble and the results are averaged over n to give one frequency spectrum $\xi_s$ for the sth spatial location.

$$\xi_s(u_k) = \frac{1}{N}\sum_{n=1}^{N} |\mathcal{F}_k\{\dot{X}_B(n, s, k)\}|, \qquad \text{Equation (48)}$$

$$s \in \{1, \ldots, \dot{S}\}, k = \{1, \ldots, \dot{K}\}.$$

Note that $\dot{X}_B(k|n, s) \in \mathbb{C}^{\dot{K}\times 1}$ and $\xi_s(u_k) \in \mathbb{R}^{\dot{K}\times 1}$ are both 1-D arrays.

The pulse-Doppler frequency axis $u_k$ is converted into a flow velocity axis $v_k$ by allying the Doppler equation. $v_k = u_k c/(2f_0 \cos \theta)$ for wave speed c, pulse transmission frequency $f_0$, and Doppler angle θ. Using the centroid method, we estimate flow speed at the sfh spatial location via Equation (48), $$\hat{v}_s = \frac{\sum_{k=1}^{\dot{K}} v_k \xi_s(v_k)}{\sum_{k=1}^{\dot{K}} \xi_s(v_k)}. \qquad \text{Equation (49)}$$

Sums are over positive and negative frequencies/velocities.

To avoid aliasing, the frame rate must exceed twice the highest nonzero frequency value, $1/T_2 \geq 2|u_{max}|$. Combining this expression with the Doppler equation, we find $1/T_2 \geq (4f_0|v_{max}| \cos \theta)/c$, where $|v_{max}|$ is the highest velocity present in the echo signal. Since $|v_{max}| \leq c/(4f_0 T_2 \cos \theta)$, in situations where the $T_2$ could not be reduced further, we adjusted Doppler angle θ.

Color-flow images are formed in a standard way by remapping estimates into a 2-D image plane, $\hat{v}_s \rightarrow \hat{v}_{m,l}$, and then superimposing them as a color overlay onto grayscale B-mode images. The spatial-mean velocity $\bar{v} = \sum_{s=1}^{\dot{S}} \hat{v}_s/\dot{S}$ for a region of relatively homogeneous flow is also found.

Example 1

Echo data were recorded using a VevoR 2100 system and a MS400 linear array (FUJIFILM VisualSonics Inc. Toronto, Ontario, Canada). The transducer transmits 2-cycle pulses with a 24 MHz center frequency. All processing was implemented in Matlab 2013b on an Intel processor i5-4300U CPU, 2.50 GHz. The highest computational burden may be filter construction, which was performed using a truncation technique to minimize running time. The average time to compute the 1600 windows for one PD image frame was 19.1 s.

In Vivo Perfusion Imaging

Figure 5:
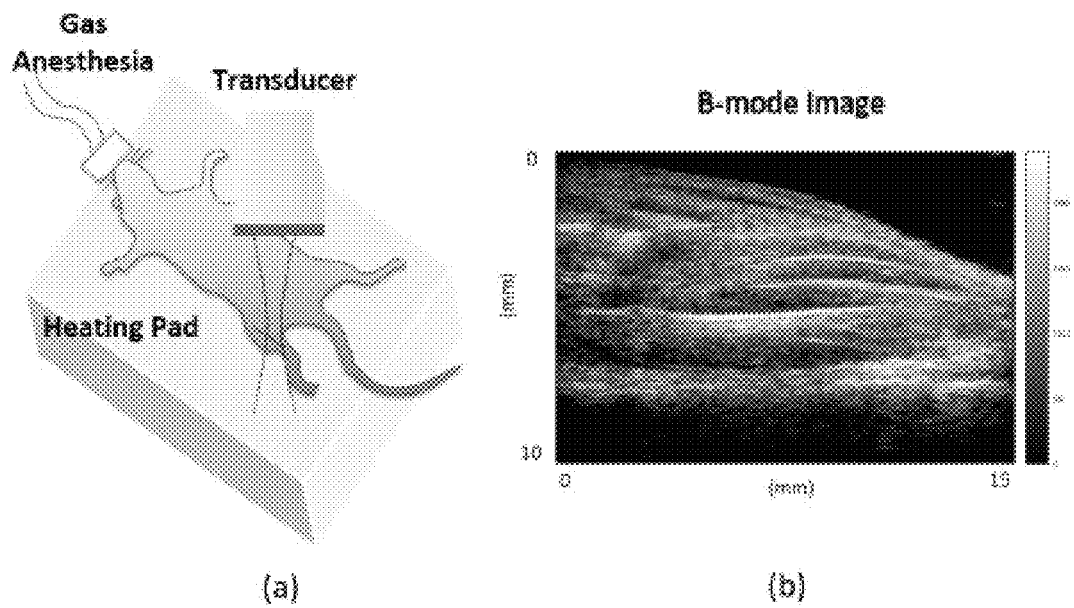
FIG. 5. (a) An anesthetized mouse placed on a heated surface in a supine position is scanned with a linear array. (b) A longitudinal cross-section of the hindlimb is displayed as a B-mode image.

A murine model of partial hindlimb ischemia was used to study the feasibility of our methods for in vivo perfusion imaging (FIG. 5). Each mouse was anesthetized with 1.5% isofluorane vaporized in $O_2$ at a rate of 1 L/min via nose cone. Each animal underwent hindlimb occlusion of the right femoral artery, without disturbing non-femoral peripheral flow to the right leg or any blood flow to the left leg. Briefly, the anesthetized mouse was placed on a 37° C. heating pad, a small incision was made on the right leg to expose the femoral vasculature, and dual ligation of the femoral artery was performed distal to the profundus branch to induce unilateral hindlimb ischemia. To confirm the occlusion and the reduction of blood flow in ischemic hindlimb, animals were imaged with a Laser Doppler Imager (moorLDI, Moor Instruments, UK) before, and immediately after ligation. For US scanning at 24 hrs post-surgery, the anesthetized animal was placed in a supine position with hindlimbs extended, and the transducer scanned the shaved inner hindlimb along a longitudinal cross section that included muscle, bone and, vasculature.

FIG. 5b displays a B-mode view of the anatomy. Although measurements were made on three mice, we will show results of scanning contralateral limbs of two mice specifically to compare methods. All experiments were performed with the approval of the Institutional Animal Care and Use Committee of the University of Illinois at Urbana-Champaign following the principles outlined by the American Physiological Society on research animal use.

TABLE 3

Acquisition parameters

| PARAMETER | VALUE |
| --- | --- |
| System | Visualsonics Vevo 2100 |
| Probe type | MS 400 |
| Pulse center frequency | 24.0 MHz |
| Doppler pulse length | 2 cycles |
| Fast-time sample size (axial length) | 200-272 (6.4-8.7 mm) |
| Fast-time sampling rate | 24.0 MHz |
| Slow-time sample size (scan time) | 17 (0.017 ms) |
| Slow-time sampling rate | 1.0 kHz |
| Frame-time sample size (scan time) | 100 (11 s) |
| Frame-time sampling rate | 9 Hz |
| Scan-line numbers (lateral length) | 240-250 (14.40-15.00 mm) |
| Scan-line density | 16.67 lines/mm |

Results

We recorded 100 sequential Doppler frames (11.1 s) from the right (ischemic) and left (healthy control) hindlimbs one day after right femoral-artery ligation. Only the first 17 frames are included in each of the PD images shown below.

Images in FIGS. 6-10 are from one animal, while the left image in FIG. 11 is from a second animal undergoing identical procedures.

First-Order Filter

We begin by processing only the first Doppler frame in the array; specifically, $X=X_{i_1=1} \in \mathbb{C}^{17 \times 200 \cdot 240 \times 1}$. Applying the spatial window described in Section 2.4, the data matrix used to form the jth spatial window for first-order eigenfilters was $X_j \in \mathbb{C}^{17 \times 14 \cdot 16}$. Computing the temporal correlation matrix in Eq. (3) and filtering the data using Eq. (5), we constructed the perfusion images found in FIG. 6.

Figure 6:
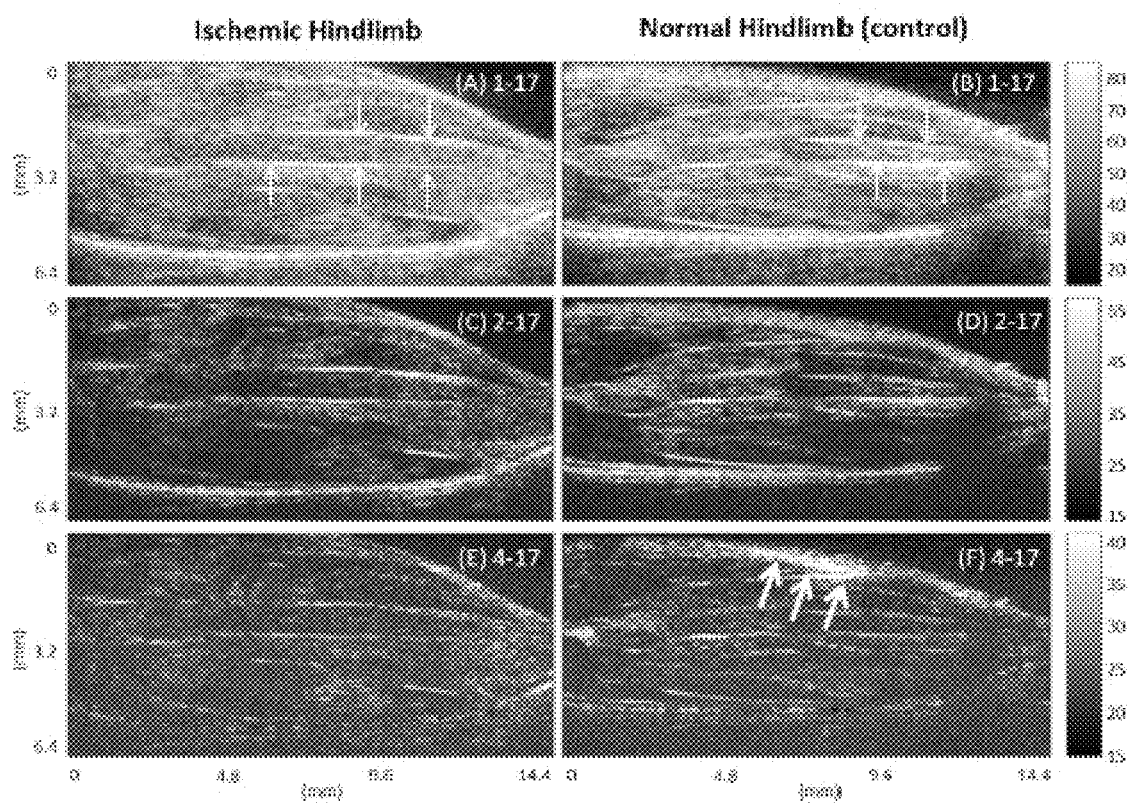
FIG. 6. Power Doppler (PD) images are shown without a B-mode component. These images are formed using a first-order eigenfilter and slow-time eigenbases. Left and right columns are images of ischemic and normal hindlimbs, respectively. Thin arrows indicate bone echoes and thick arrows indicate fast arterial flow. The numbers at the top of each image indicate the range of indices passed through the filter in the summation of Eq. (5). Since the possible range is 1-17, lower rows are more heavily filtered images.

The first row FIGS. 6 (A) and (B), displays images obtained without filtering to show the full clutter component in the PD signal. Arrows indicate echoes from bone surfaces. The second row FIGS. 6 (C) and (D) are filtered images formed by discarding the first (most energetic) slow-time eigen-component and preserving eigen-components 2-17. Third row images, FIGS. 6 (E) and (F), discard the first three slow-time eigen-components, leaving 4-17. Discarding the three most energetic eigenvalues removes many of the clutter echoes from both images, although the bone reflections remain. More importantly, there is no apparent discriminability between the ischemic and control states except for the appearance of a segment of arterial flow as indicated by the larger arrows in (F) near the proximal skin surface of the control hindlimb.

Second-Order Filter

Figure 7:
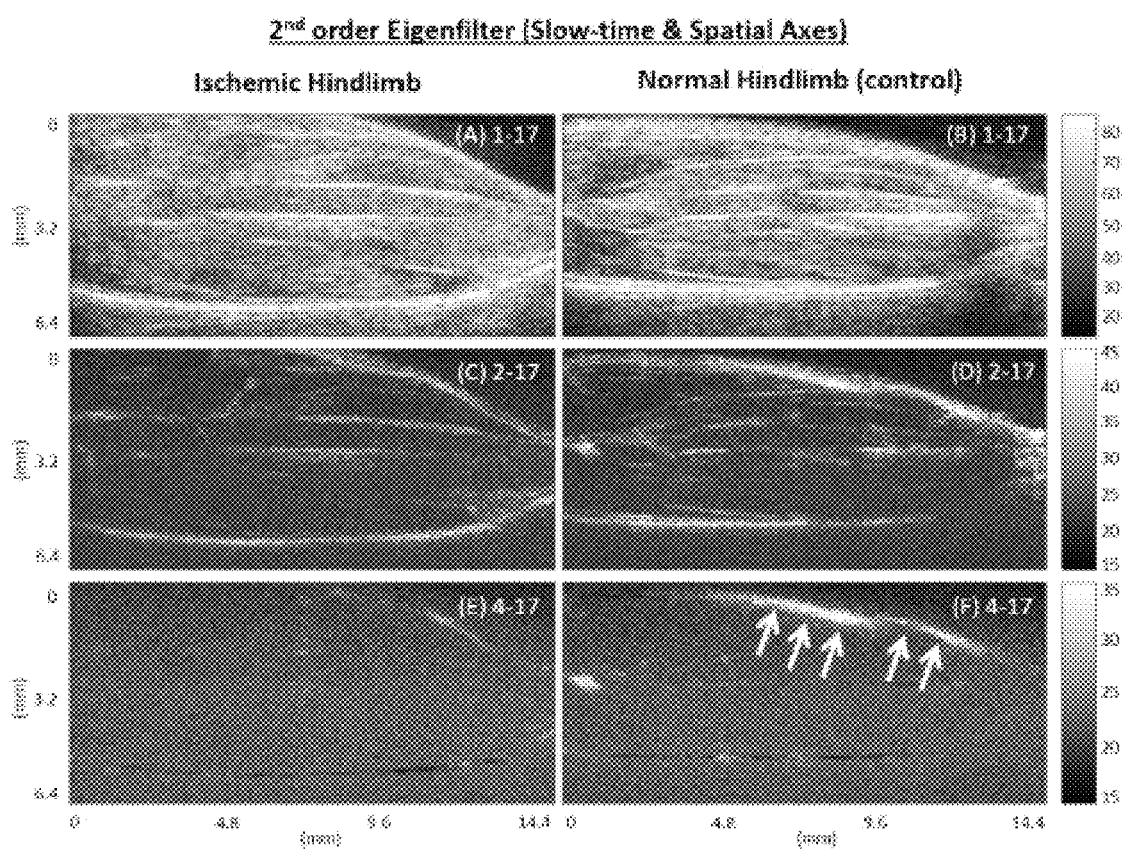
FIG. 7. PD images using a 2nd-order SVD filter based on slow-time and spatial eigenbases to show primarily arterial flow. Left and right columns are images of ischemic and normal hindlimbs, respectively. Thick arrows indicate a region with fast arterial flow. The numbers at the top of each image indicate the range of indices passed through the filter in the summation of Eq. (8). Possible range: 1-17.
Figure 8:
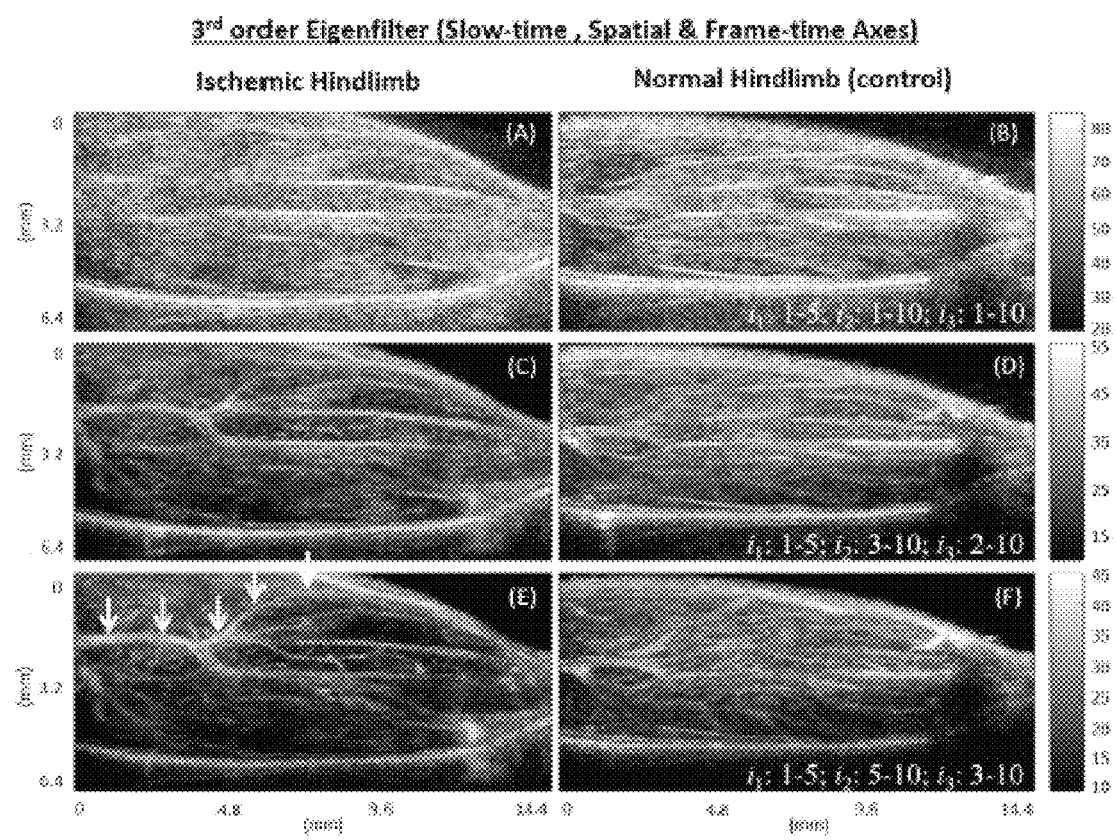
FIG. 8. PD images using the full 3-D data array and HOSVD filter to show perfusion. Left and right columns are images of ischemic and normal hindlimbs, respectively. Filter parameters shown at the bottom of an image apply to the normal and ischemic images in that row. As filter parameters change, vascular structures emerge (arrows in (E) point to one branch) while clutter and noise components fade. The normal flow image (F) is uniformly perfused, although the signal strength near the bottom surface of the leg is low because of acoustic attenuation. In contrast, the ischemic hindlimb in (E) with lost femoral-arterial flow shows perfusion-deficit patches and prominent vessels that now contain low-speed blood flow from the remaining peripheral vessels. Note that the same echo data are used to form images in FIGS. 6-8.

The same data were processed by the second-order SVD filter via Eq. (8). FIG. 7 shows the resulting PD images using slow-time and spatial eigenbases. As in FIG. 6, the three rows describe three levels of filtering given by numbers in the upper right corner. Virtually all echoes are eliminated in images (E) and (F) except for the arterial flow near the skin surface in the control hindlimb. Comparing FIGS. 6 and 7, we see the effectiveness of including the spatial axis of the data array for clutter suppression. However, the slow-time axis offers very little sensitivity to perfusion signals; the remaining signal power indicates a segment of arterial flow (arrows).

Third-Order Filter

We again analyzed the same echo data array but now employing all three dimensions using the HOSVD filters of Eq. (15). In the bottom row of FIG. 8, we see the emergence of vascular structures that are not at all apparent with 1-D and 2-D filters in FIGS. 6 and 7. There are three sets of filter indices, $i_1$, $i_2$, $i_3$, that specify the ranges in G passed by the 3-D filter. These are given at the bottom of the images, where values shown apply to both images in that row. Here we see perfusion and slow vascular flow but very little fast flow or clutter. The advantages brought to bear in these results are three fold. First, the use of frame-time data enhances SNCR for perfusion. Second, employing all three data-array axes increases the effectiveness of clutter filtering. Third, we use more data than that applied to the results of FIGS. 6 and 7, which greatly suppresses acquisition noise.

Figure 9:
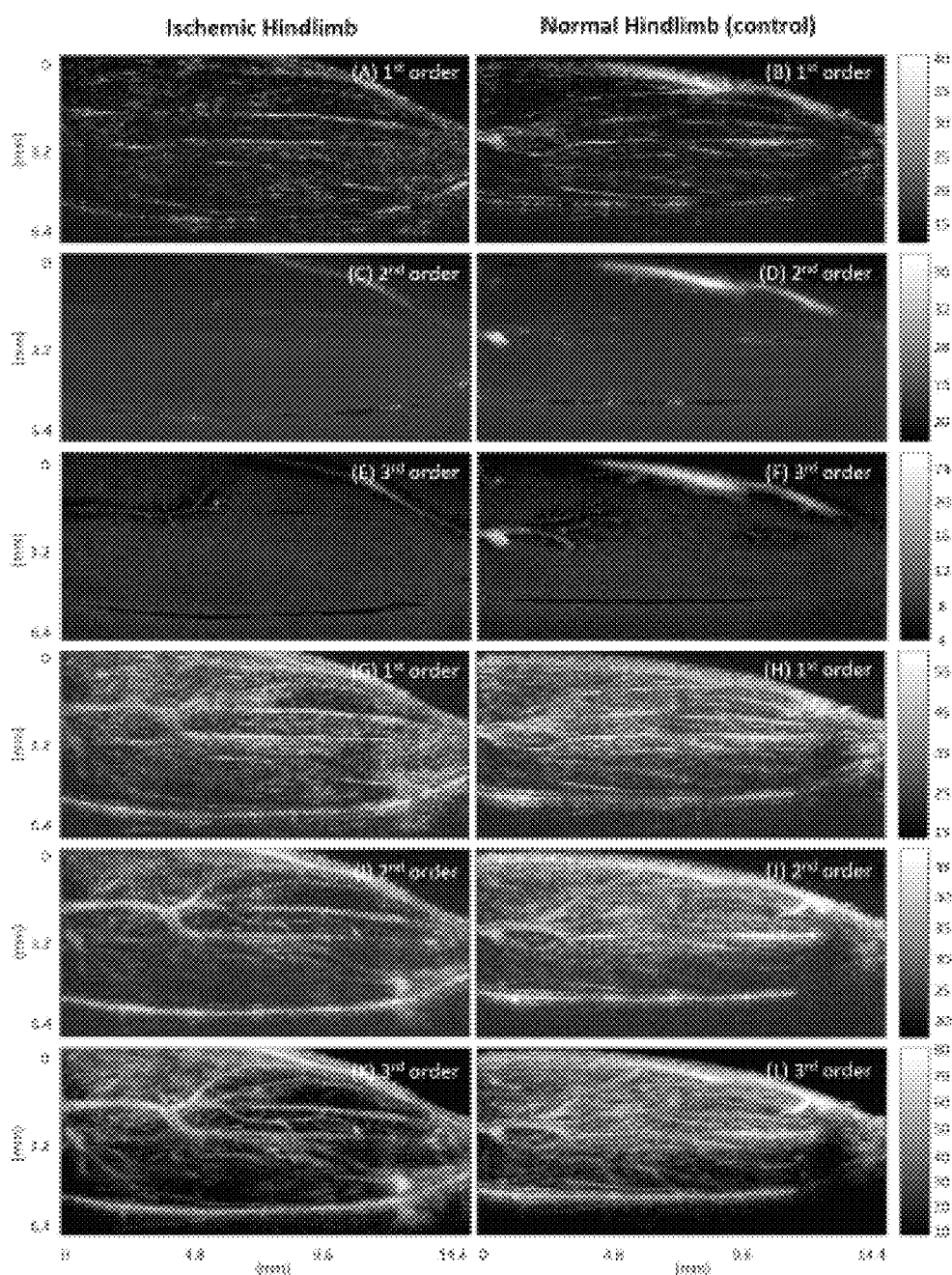
FIG. 9. Comparisons of the visually clearest examples of first, second, and third-order filters applied to the slow-time data axis (A-F) to display arterial flow and to the frame-time data axis (G-L) to display perfusion. Each image is based on same 17 frames of echo data.

In FIG. 9, we compare results of first, second, and third-order clutter filters for displaying the slow-time arterial flow (first three rows of images) and frame-time perfusion (last three rows of images). All results were obtained from the same echo-data array, viz., $X \in \mathbb{C}^{7 \times 200 \cdot 240 \times 17}$. For the first and second-order filters, 17 post-filtered images were averaged over either the slow-time or the frame-time axes to take full advantage of all echo data. The third-order filter first decomposes the entire data array before projecting onto the appropriate subspace. The entire echo-data array influences each image displayed in FIG. 9. In each case, we selected filter parameters that provided the clearest visualization of RBC movement. From one set of recorded echo data, we can see the effects of filter order and data-array axis (eigen-basis) on the ability to visualize fast or slow-flow patterns in normal and ischemic hindlimbs. In particular, compare the noise levels in the third-order filter results with first and second-order results. A significant, noticeable contrast improvement was observed. The full impact of using 3-D data may be appreciated when we threshold and color code the power signals before overlaying them on the B-mode image (FIG. 10) as may be conventionally displayed for clinical applications. We used a blue color map to display the slow-time-axis power (arterial flows) seen in FIGS. 9 (E) and (F) and a red color map to display the frame-time-axis power (blood perfusion) from FIGS. 9 (K) and (L). Colored PD images were displayed in the third row of FIG. 10. The inset shows 160 pin-dia vessels are clearly resolved.

The first and second rows of FIG. 10 display FIR-filtered PD images, and the third row shows HOSVD-filtered images. All were computed from the same echo-data array. We applied a fixed 25 Hz high-pass FIR filter in (A) and (B) and a 150 Hz high-pass FIR filter in (C) and (D). While surface vessels and bone artifacts can be seen in the 25 Hz FIR-filtered and the HOSVD images of FIG. 10, only HOSVD images show slow flow within interior vessels of the ischemic hindlimb and uniformly perfused muscle in proximal regions of healthy controls. Sensitivity was reduced in distal muscle regions of all images as sound attenuation reduced SNCR.

Appendix B

This appendix briefly explains the outer-product notation used above. The n-mode outer product of $I_N$-dimensional tensor $A \in \mathbb{C}^{I_1 \times I_2 \times \ldots \times I_{n-1} \times I_n \times I_{n+1} \times \ldots \times I_N}$ and matrix $Z \in \mathbb{C}^{J_n \times I_n}$ is $$D = A \times_n Z \in \mathbb{C}^{I_1 \times \ldots \times I_{n-1} \times J_n \times I_{n+1} \times \ldots \times I_N}$$

where an element of tensor D is $$d_{i_1 \ldots i_{n-1} j_n i_{n+1} \ldots i_N} = \Sigma_{i_n=1}^{I_n} a_{i_1 \ldots i_N} z_{j_n i_n},$$

The $(l_1, l_2, l_3)$-th element of $X \in \mathbb{C}^{N \times S \times K}$ is $$x_{l_1, l_2, l_3} = \Sigma_{i_1=1}^{N} \Sigma_{i_2=1}^{S} \Sigma_{i_3=1}^{K} g_{i_1, i_2, i_3} u_{l_1, i_1} v_{l_2, i_2} w_{l_3, i_3},$$

which corresponds to a second line of Eq. (12).

Example 2

Figure 16:
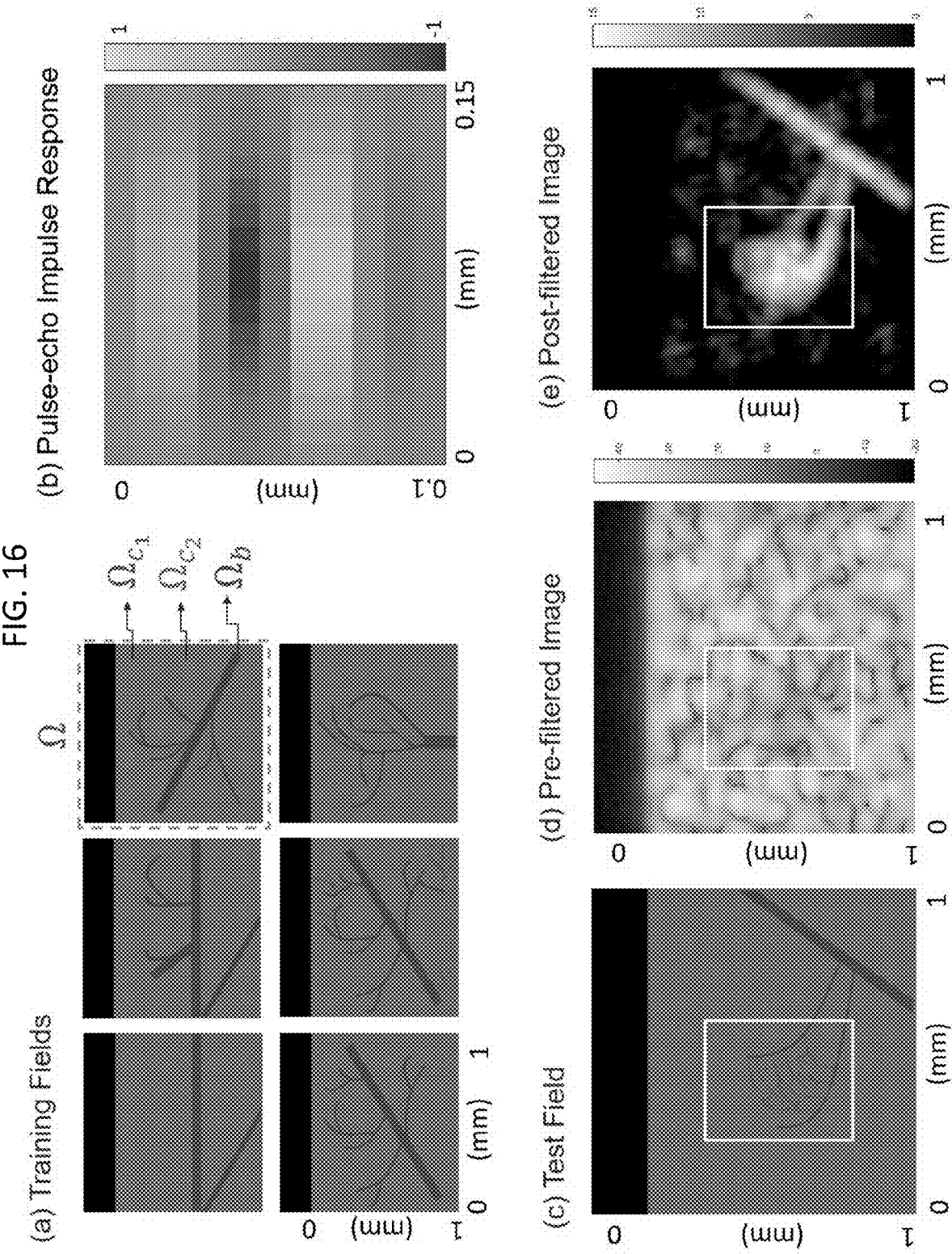
FIG. 16. Examples of training and testing fields that were used to develop a clutter filter classifier are shown with echo simulations. (a) Training fields. (b) Pulse-echo impulse response. (c) Test field. (d) Prefiltered image. (e) Postfiltered image. In (a), each of the six fields shown is composed of tissue $\Omega_{c1}$, $\Omega_{c2}$, and vascular $\Omega_b$, regions. A 15-MHz pulse-echo impulse response is illustrated in (b). For the test field in (c), the prefiltered and postfiltered PD images are shown in (d) and (e) for 15-MHz pulses. White boxes: regions containing fine vascular structures.

Simulation. Simulation data can be used to illustrate a clutter filter GM classifier embodiment of this invention. A classifier was trained and tested using simulation data and then applied in the phantom and in vivo tumor studies shown in the following. FIG. 16(a) illustrates 6 of 12 heterogeneous regions Ω from which echo data were simulated for classifier training. The size of each field was 1 mm×1 mm and vessel diameters ranged between 10 and 100 μm. The center frequency of pulse transmissions was either 10 or 15 MHz. Point scatterers were initially uniformly distributed in tissue regions $\Omega_c$ and vascular regions $\Omega_b$. Tissue regions were further divided into $\Omega_{c1}$ and $\Omega_{c2}$ with different echogenicity. Displacements of all scatterers over time follow the tissue and blood motion functions described above. Included in the 12 training fields, clutter-to blood ratios were varied over the range 15 dB<$r_{CB}$<40 dB and the blood-to-noise ratios over the range 5 dB<$r_{BN}$<30 dB via Equation (23). For training, 1800 data arrays were produced from the 12 regions and multiple combinations of parameters. All modeling and analysis parameters are summarized in Tables 4 and 5.

TABLE 4

Echo Data Simulation Parameters

| Category/Function | Parameter | Value/Range |
|---|---|---|
| Tissue scatterers $c_i$ (•) in field $\Omega_{c_1}$ | Numbers $J_{c_1}$ | 4000 |
| | Echo amplitude mean $\bar{\alpha}_{c_1}$ | 15 |
| | Echo amplitude STD | 1 |
| Tissue scatterers $c_i$ (•) in field $\Omega_{c_2}$ | Numbers $J_{c_2}$ | 1200 |
| | Echo amplitude mean $\bar{\alpha}_{c_2}$ | 25 |
| | Echo amplitude STD | 1 |
| Blood scatterers $b_i$ (•) in field $\Omega_b$ | Numbers $J_b$ | 1000 |
| | Echo amplitude mean $\bar{\alpha}_b$ | 1, 2, 3, 4 |
| | Echo amplitude STD | 1 |
| Source power ratio | Clutter-to-blood $\tau_{CB}$ | 15-40 dB |
| | Blood-to-noise $\tau_{BN}$ | 5-30 dB |
| Rigid-body motion ($\eta(t)$) | Amplitude $\beta$ | 0-400 μm |
| | Breath interval $t_0$ | 10 s |
| | Interval $\sigma$ | 0.5 s |
| Vibration ($\xi(t)$) | Amplitude $\gamma$ | 0-60 μm |
| | Frequency $w_0$ | 7.5 rad/s |
| | Direction $\theta$ | 0-2π rad |
| Blood flow ($\zeta(t)$) | Speed | 1-3 mm/s |
| Pulse-echo impulse response ($h(z, y)$) | Pulse cycles | 2 |
| | Bandwidth | 60% |
| | F-number | 1.2 |

TABLE 5

Experimental Parameters

| Parameter | Simulation | Phantom | In-vivo Tumor |
|---|---|---|---|
| Axial samples (M) | 52 | 100 | 168-272 |
| Axial sampling rate | 40.0 MHz | 12.5 MHz | 24.0 MHz |
| Axial size | 1 mm | 6.2 mm | 5.4-8.7 mm |
| Slow-time samples (N) | 15 | 17 | 17 |
| Slow-time sampling rate | 1.0 kHz | 1.0 KHz | 1.0 kHz |
| Frame-time samples (K) | 30 | 30 | 30 |
| Frame-time sampling rate | 20 Hz | 15 Hz | 10-15 Hz |
| Scan-line numbers (L) | 50 | 53 | 120-234 |
| Scan-line density | 50/mm | 4/mm | 16.67/mm |
| Lateral size | 1 mm | 13.2 mm | 7-14 mm |
| Spatial samples (S = LM) | 2.6k | 5.3k | 20k-64k |
| Sub-block size ($\dot{N} \times \dot{S} \times \dot{K}$) | 17 × 2.6k × 30 | 17 × 576 × 30 | 17 × 2.5k × 30 |
| Slow-time division ($J_1$) | 1 | 1 | 1 |
| Spatial division ($J_2$) | 1 | 15 | 400 |
| Frame-time division ($J_3$) | 1 | 1 | 1 |
| Block numbers (J = $J_1 J_2 J_3$) | 1 | 15 | 400 |
| Classification threshold ($\tau$) | 1 | 1 | 1 |

Training and testing data were simulated using identical parameters, although the data sets are statistically independent of each other. FIG. 16(c) displays one of the testing fields. Array data were processed for HOSVD clutter filtering followed by noise filtering. FIGS. 16(d) and (e) show that vascular structures are clearly visualized in the postfiltered PD map but not in the prefiltered PD map. The 50-μm vessels are not resolved at 15 MHz.

Figure 17:
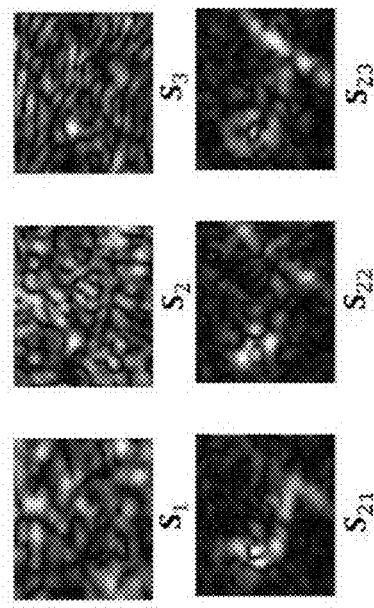
FIG. 17. Measured components of feature vector z analogous to those diagramed in FIG. 4. These measurements are from echo simulations based on the test field of FIG. 16(c). (a) Contributions of the eigenvalues for clutter (open circles) and blood ($\Delta$) signals are shown. Only the first 40 components of the spatial eigen mode are shown. (b) Six eigen images $S_1$, $S_2$, $S_3$, $S_{21}$, $S_{22}$, and $S_{23}$, and the similarity measures $d_{i2}$. (c) Mean correlation coefficients q[k] between the kth frame and others are plotted. (d) Contribution of the $i_3$th frame-time eigenvector ($w_{i3}$) to the rigid-motion corruption coefficient $r_{i3}$.
Figure 17:
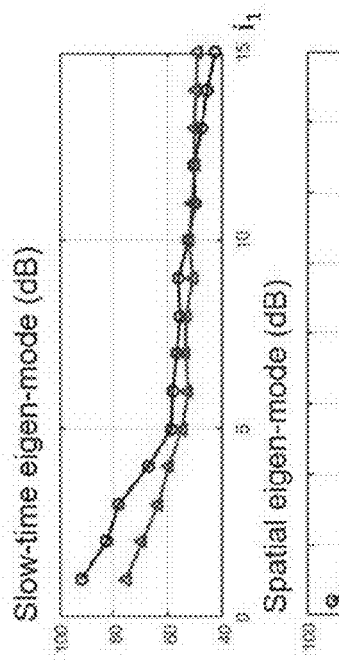
Figure 17:
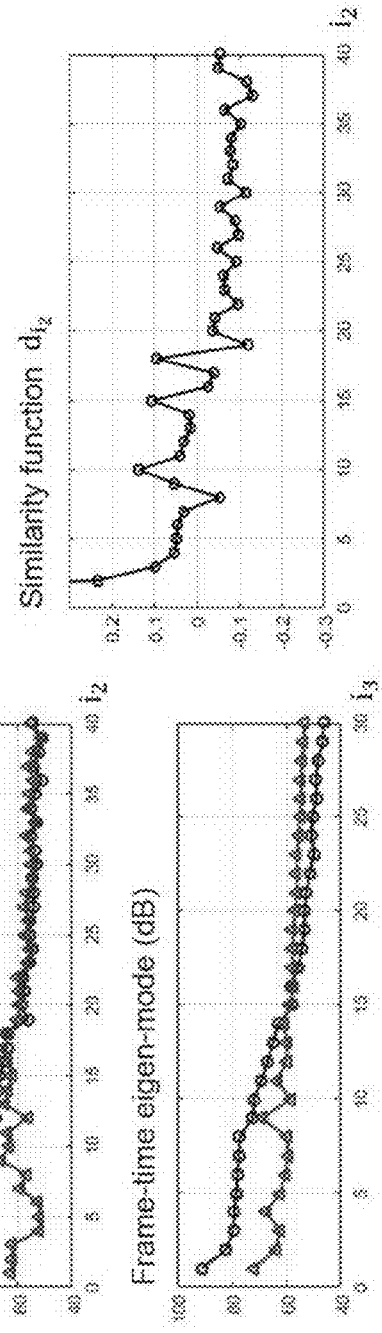
Figure 17:
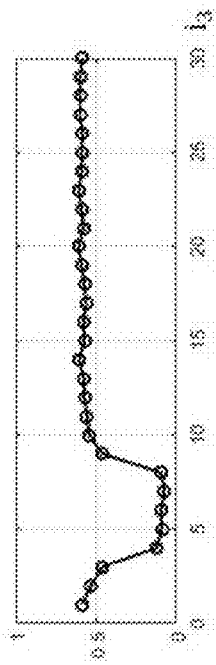
Figure 17:
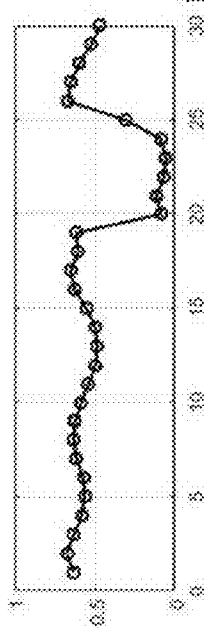

FIG. 17 shows an embodiment from echo simulations of classification feature vector z components. FIG. 17(a) shows significant overlap between the blood and clutter components, except for the largest eigenvalues where clutter dominates. FIG. 17(b) displays the first three and middle three eigen images, $\{S_{i_2}|i_2=1, 2, 3, 21, 22, 23\}$. The first three eigen images show tissue-related speckle because their eigenvectors are mostly influenced by tissue scattering (clutter). In contrast, vessel-like patterns found in the object of FIG. 16(c) appear in eigenimages 21-23, showing how those eigenvalues are dominated by vascular flow. Finally, the dip in frame-time correlation in FIG. 17(d) identifies those frames most corrupted by a rigid body motion that simulates the effects of breathing.

1) Errors in Blood-Signal Estimation.

1) Errors in Blood-Signal Estimation: Simulation enables direct error estimation as states are known. Let fractional error be defined as $\epsilon = \|\mathcal{B} - \hat{\mathcal{B}}\|^2 / \|\mathcal{B}\|^2$ where $\|\mathcal{B}\|$ is the known blood-echo power-echo power [see (2) and (3)] and $\|\hat{\mathcal{B}}\|$ is the estimated power from Equation (44). When the clutter and noise filters are highly effective, $\epsilon \cong 0$.

Conversely, if filters are poorly designed and they remove all of the blood signal, then $\epsilon \cong 1$. Although it is possible to obtain error values greater than 1, in practice, we find $0 < \epsilon < 1$ as shown in the following.

We measure two fractional errors: $\epsilon_{best}$ computes $\hat{\mathcal{B}}$ from the training data while $\epsilon_{GM}$ computes $\hat{\mathcal{B}}$ using the testing data. Since $\epsilon_{best}$ uses exactly known training data, these errors are unavoidably generated by applying a hard threshold to data where the clutter and blood subspaces overlap. $\epsilon_{GM}$ are obtained under testing conditions and, consequently, a more practical measure of filter performance.

Figure 18:
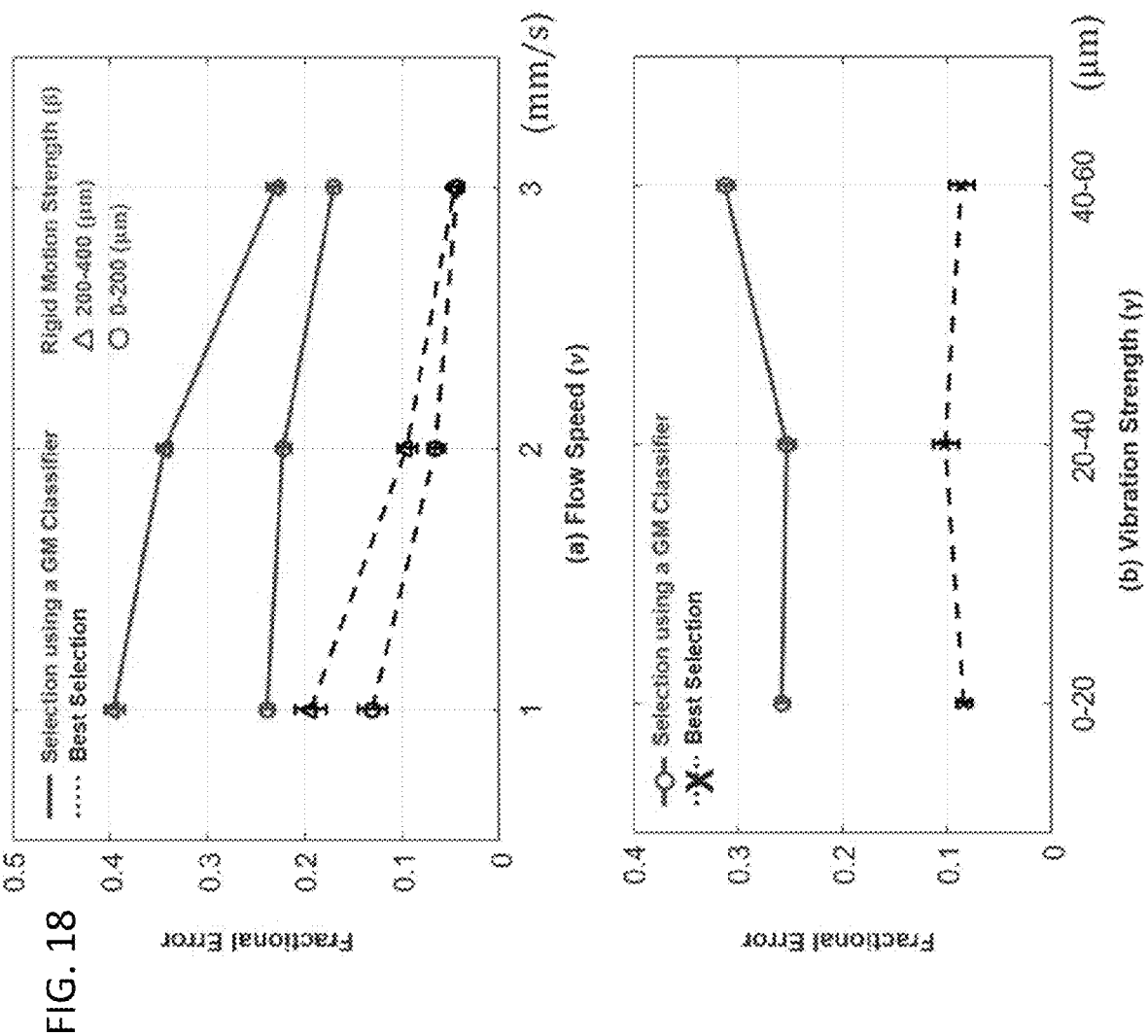
FIG. 18. Fractional errors $\epsilon_{GM}$ and $\epsilon_{best}$ as functions of (a) flow speed for clutter amplitudes $\beta$ and (b) vibration strengths $\gamma$ at 2 mm/s flow speed. Points and error bars denote sample means and standard deviations of the mean, respectively. Large clutter motion and slow blood speeds generate the largest classification errors because of subspace overlap.

FIG. 18 illustrates how classification errors are influenced by clutter motion and flow speed. For the full range of conditions, $\beta < 400$ μm, $\gamma < 60$ μm, and $v < 3$ mm/s, classification errors, $\epsilon GM - \epsilon best$, remain relatively constant between 0.1 and 0.2. However, increasing the rigid-body clutter amplitude expands the extent of the clutter subspace in the core tensor. This larger clutter eigen-bandwidth increases the overlap between the clutter and blood subspaces, thus increasing the fractional error. Alternatively, faster blood-flow speeds reduce the clutter-blood subspace overlap by shifting and expanding the blood subspace to smaller eigenvalue (larger index elements, $i_3$).

Flow Phantom

Figure 19:
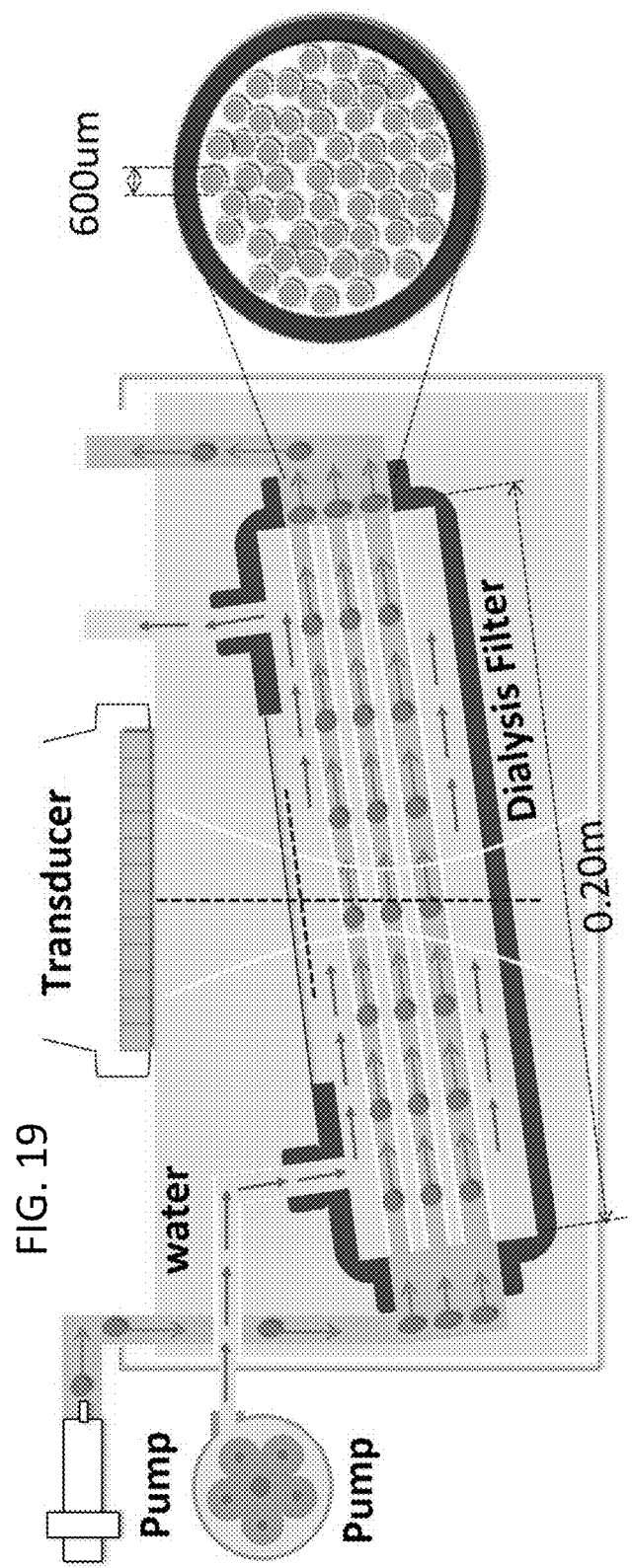
FIG. 19. Flow phantom mimicking blood circulation consists of a dialysis cartridge and two pumping systems. A syringe pump infuses either water (control state) or BM fluid (perfusion state) constantly into 0.6 mm fibers. A peristaltic pump circulates water pulses outside the fibers for clutter motion. A linear transducer scans the cartridge through an acoustic window for echo acquisition.

A phantom study was conducted to assess microvascular flow estimation under experimental conditions. FIG. 19 shows a dialysis cartridge containing a bundle of 0.6-mm inner diameter cellulose fibers (Spectrum Laboratories Inc., Rancho Dominguez, Calif., USA). Flow in the fibers was controlled by a programmable syringe pump injecting at a constant rate either pure water for the control state or blood-mimicking (BM) fluid (CIRS, Norfork, Va., USA) for test states. In addition, pulsatile water flow was generated outside the fibers using a peristaltic pump to induce sinusoidal clutter motion at frequencies between 0 and 0.5 Hz. A portion of the thick plastic case protecting the cellulose fibers was removed and the area was wrapped with paraffin film (Parafilm, Bemis Company Inc., Neenah, Wis., USA) to provide an acoustic window and housing structure for pulsatile clutter generation. The cartridge was immersed in degassed water for ultrasound scanning. A Vevo 2100 system with an MS200 linear array operated at 12.5 MHz (FUJIFILM VisualSonics Inc., Toronto, Ontario, Canada) was used to acquire IQ echo data in the color-flow mode for offline processing.

Five flow states were compared: control state i=1 has stationary water in the fibers at 0 mL/min; i=2 has stationary BM fluid at 0 mL/min; i=3 has BM fluid at 1 mL/min; i=4 has BM fluid at 2 mL/min; and i=5 has BM fluid at 3 mL/min. At each flow state, we acquired data at four clutter motion levels: j=1 is no motion (peristaltic pump off), j=2 is pumping with rotation frequency 0.16 Hz, j=3 at 0.33 Hz, and j=4 is 0.5 Hz. These values span the 12-20 breath/min range. There were 12 acquisitions recorded per state and motion level, each 2 s in duration (30 Doppler frames). PD maps $P_k$ were formed for regions 6.2 mm axially by 13.2 mm laterally (see white boxes in FIG. 20). All experimental and filter parameters are summarized in a column of Table 5 labeled "phantom."

Figure 20:
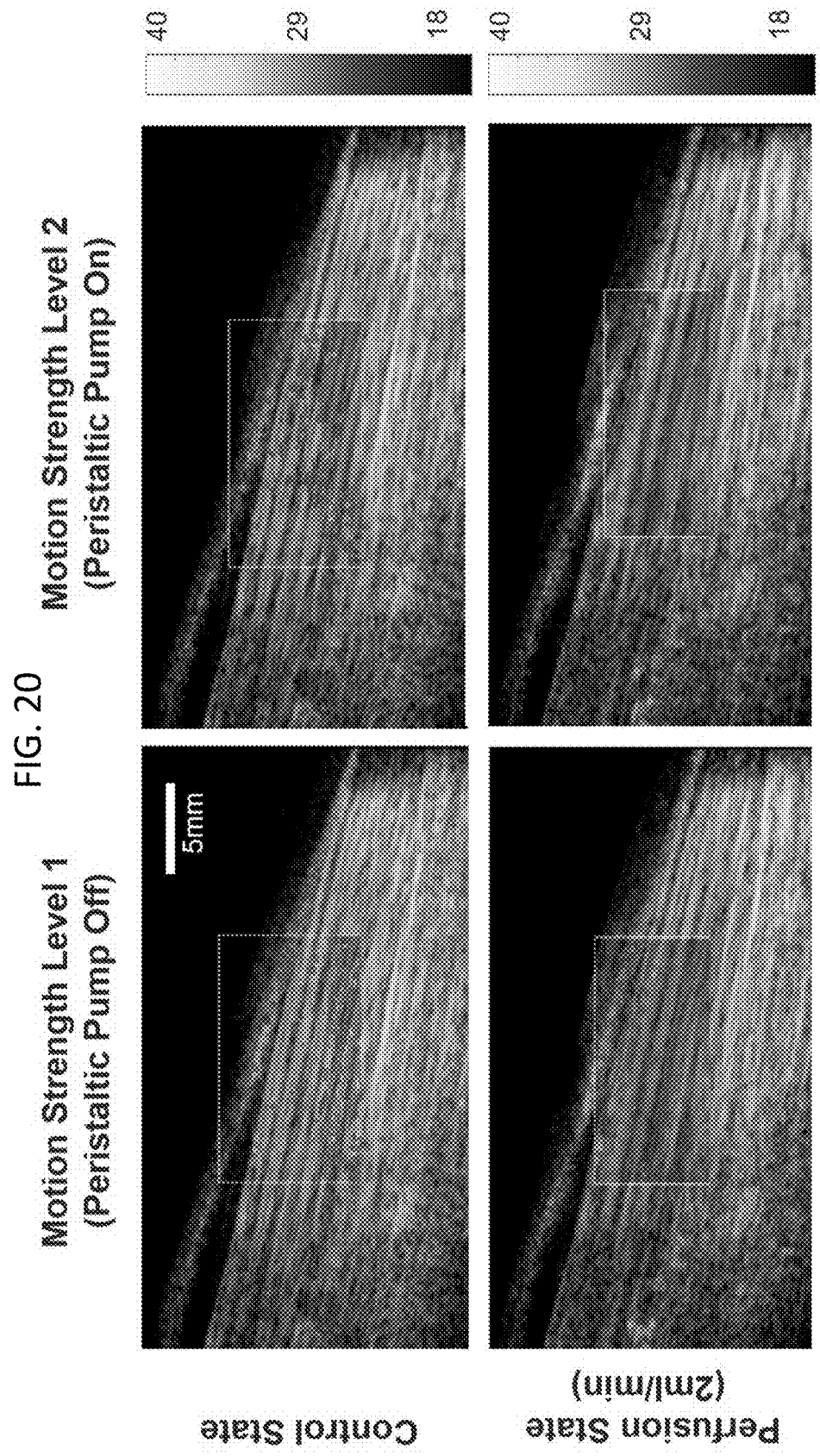
FIG. 20. PD images of 0.6 mm diameter cellulose-fiber flow phantom at 12.5 MHz. Each is a filtered PD map superimposed on the corresponding B-mode image. Columns display two clutter levels. Rows display the control and 2 mL/min flow states. Color bar: signal power.
Figure 21:
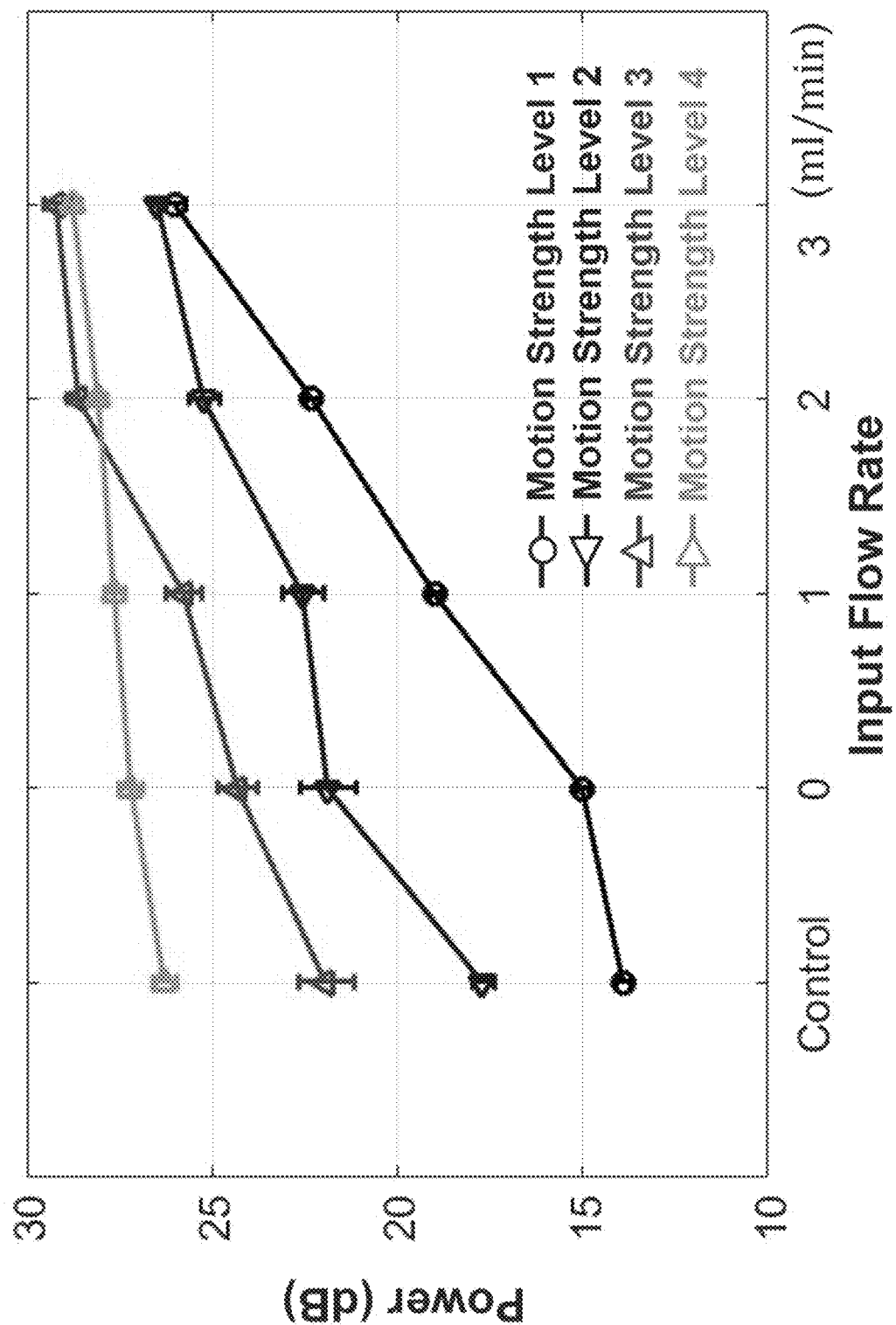
FIG. 21. Postfiltered echo power versus input flow for four clutter levels. Error bar: standard errors from averaging results of 12 acquisitions.

FIG. 20 shows examples of PD maps superimposed on their B-mode images for two clutter levels. Postfilter signal power was found to increase with the clutter level. The changes were quantified by computing the pixel average $s_{i,j,k}=(1/ML)\Sigma_{(m,l)} P_k[m,1]$ for every PD image FIG. 21 shows values for the 12 acquisitions, $\bar{s}_{ij}=(1/12)\Sigma_{k=1}^{12}$ sijk, for the flow state i and live clutter motion level j. We see that the posifilter signal power (dB) increases linearly with the flow rate. Unfortunately, the rate of increase depends on the clutter motion level.

The slope change with the clutter level in FIG. 21 is consistent with our findings in the simulation results. Increasing the levels of the clutter energy for fixed flow states increases the overlap of the blood and clutter subspaces within the core tensor. The overlap is high for the slower flow velocities. Because we employ a hard threshold, the increase in postfilter signal power with the clutter level at the smallest blood speeds is expected. High-amplitude rigid-body clutter motion generates an incomplete separation of tissue and blood signals with the effect of reducing PD image contrast as discussed in the following.

In Vivo Tumor Study

Figure 22:
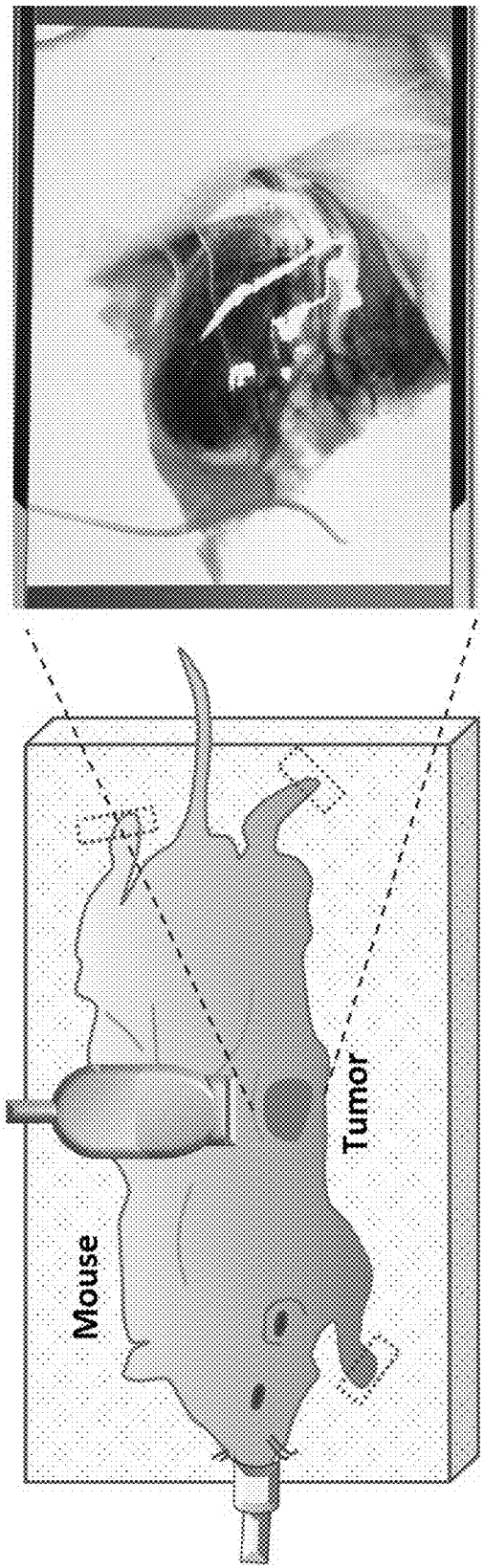
FIG. 22. Murine model of melanoma is illustrated. A mouse implanted with tumor cells is scanned in a prone position. Data are acquired at 24 MHz with the Vevo 2100 over 3 weeks.

To further test our imaging methods, we scanned implanted mouse melanomas, in vivo. Tumor cells injected subcutaneously into the flank of male black C57BL/6 mice (Charles River Laboratories, Skokie, Ill., USA) were investigated over time as tumors grew in size and vasculature. FIG. 22 illustrates the scan positioning. Echo data were acquired 1, 2, and 3 weeks post-implantation using the Vevo 2100 system and the MS400 transducer at 24 MHz (see Table 5). Mice anesthetized with 1%-3% isofluorane is scanned to acquire 3 s of echo data (30 sequential Doppler frames at 10-Hz frame rate). The 24-MHz pulses provide high-B-mode spatial and contrast resolutions, allowing tumors to be readily located as hypoechoic regions. The clutter filter classifier that was trained using the simulation data was applied to the tumor data to identify core elements belonging to the clutter subspace. We also applied the methods above to set velocity windows for slow flow (<4 mm/min) and fast flow (>4 mm/min) regions. The PD map was determined from the blood signal measured using Equation (44).

FIG. 23 displays one example of low- and high-flow PD images acquired at weeks 1-3. 1 week post-implantation, the small nascent tumor appears as a hypoechoic region of the enhanced perfusion. The tumor grows rapidly after 1 week and increasing its microvascular density. This tumor has only a few larger vessels with higher velocity flows. Note that the breathing rate of the anesthetized mouse was slowed, making it easy to acquire 3 s of echo data between the breaths. In this example, the clutter was primarily from the stationary and vibrating tissues.

Example 3

Results obtained at 12.5 MHz and 5.0 MHz applied the acquisition parameters listed in Table 2 and clutter filter parameters listed in Table 6. The higher pulse frequency provides greater sensitivity and spatial resolution to flow echoes but less penetration in attenuating media. A validation frequency range of 5-12.5 MHz spans most of clinical imaging. Note the number of samples in the spatial sub-block window used to develop clutter filters was adjusted so the spatial areas applied at both pulse frequencies were about the same. Similarly, the numbers of pulses per frame and the number of frames recorded were adjusted to give roughly equal numbers at 5 and 12.5 MHz.

A. Flow Speed Measurements

FIG. 26 summarizes velocity estimation experiments using Phantom I. Negative velocities indicate flow away from the transducer (opposing the direction indicated in FIG. 25).

The results indicated that spatial-average velocity r) closely tracks the independent stopwatch measurements $\bar{v}'$. Deviations of $\bar{v}$ from $\bar{v}'$ can be attributed to several sources. First, frame rate adjustments for the 12.5 MHz (5 MHz) measurements were limited such that aliasing along the frame-time axis was significant at flows greater than ~3 mL/min (~4 mL/min). Frame-time aliasing acts to bias these speed estimates low.

In contrast, power Doppler measurements are not affected by aliasing effects. Second, in the presence of moving clutter, speed estimates are biased high, especially at 5 MHz and at the lowest flows where clutter-driven movement of TM blood is indistinguishable from flow. Under these conditions, clutter and blood subspaces are only weakly separable. Third, a few cellulose fibers ruptured from forces generated by the peristaltic pump. Ruptured fibers release TM blood into the region surrounding fibers that flows along the fibers. Escaping TM blood contributes echoes but not to fiber flow, and hence it becomes a clutter source. Despite these limitations, measurements are sensitive to fiber flows up to 3 or 4 mL/min depending on the pulse frequency.

B. Color Flow Images

Figure 27:
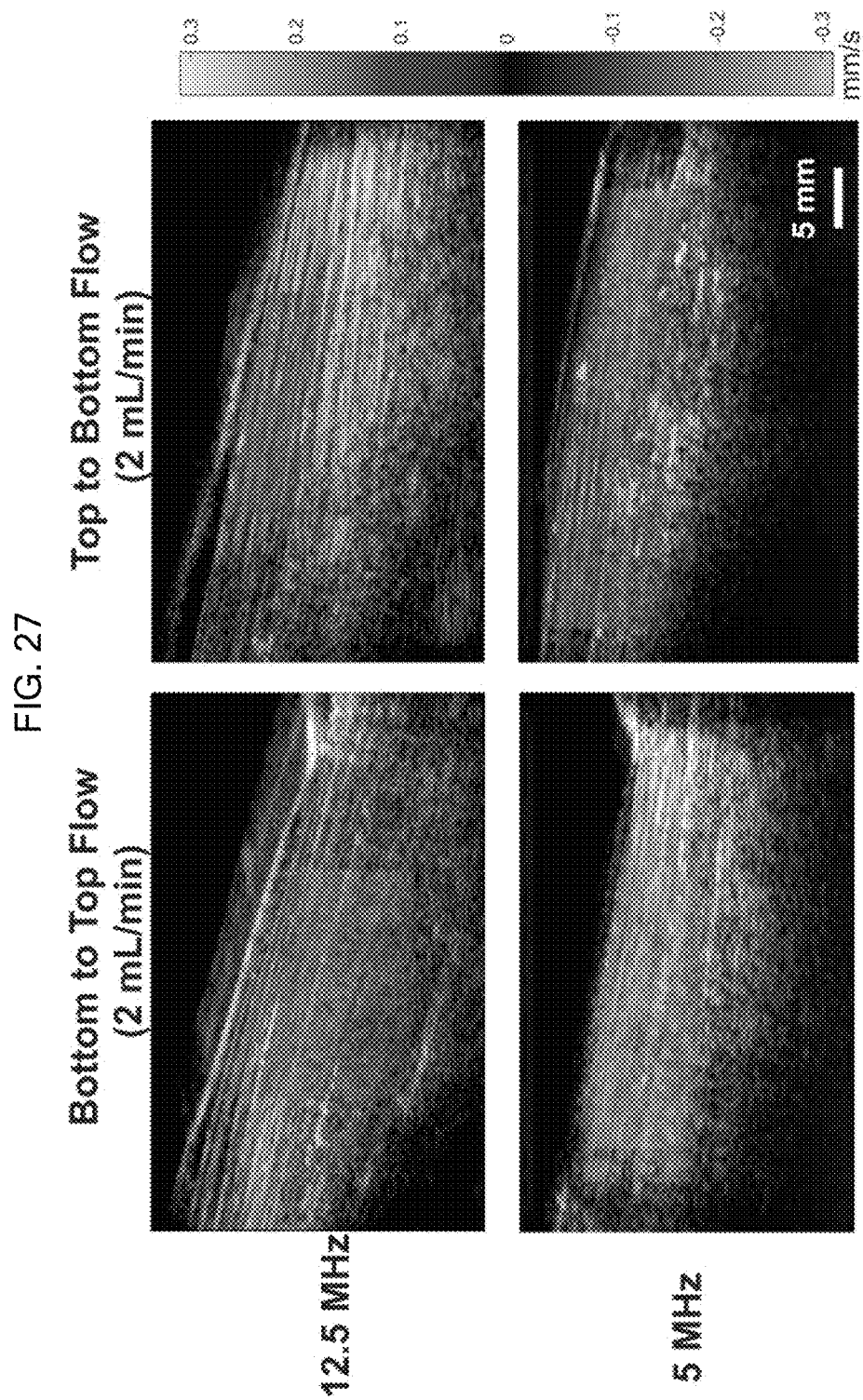
FIG. 27. CF images of Phantom I (directional fibers) for stationary clutter. Images at 5 MHz and 12.5 MHz correspond to the average velocity measurements indicated in FIG. 26.

FIG. 27 shows color flow (CF) images of Phantom I. The directionality of the fibers yield fairly uniform velocity maps of the 2 mL/min flows in both directions. Images with moving clutter were similar to those shown in FIG. 27 having stationary clutter. All clutter filter parameters are listed in Table 6. In Table 6, numbers in the last two columns define subspace eigenbandwidths for clutter filter pass bands of the three data array dimensions, which can vary under different experimental conditions.

TABLE 6

Clutter Filter Thresholds

| Phantom | $f_o$ | Data Array Dimension | Stationary Clutter | Moving Clutter |
|---|---|---|---|---|
| I | 12.5 MHz | Slow-time | 1-5 | 1-5 |
|  |  | Frame-time | 3-20 | 7-25 |
|  |  | Spatial | 5-30 | 8-30 |
| I | 3 MHz | Slow-time | 1-5 | 1-5 |
|  |  | Frame-time | 3-10 | 7-14 |
|  |  | Spatial | 5-20 | 7-25 |
| II | 5 MHz | Slow-time | 1-3 | 1-3 |
|  |  | Frame-time | 3-20 | 5-20 |
|  |  | Spatial | 10-30 | 20-40 |

C. Power-Doppler Images

Figure 28:
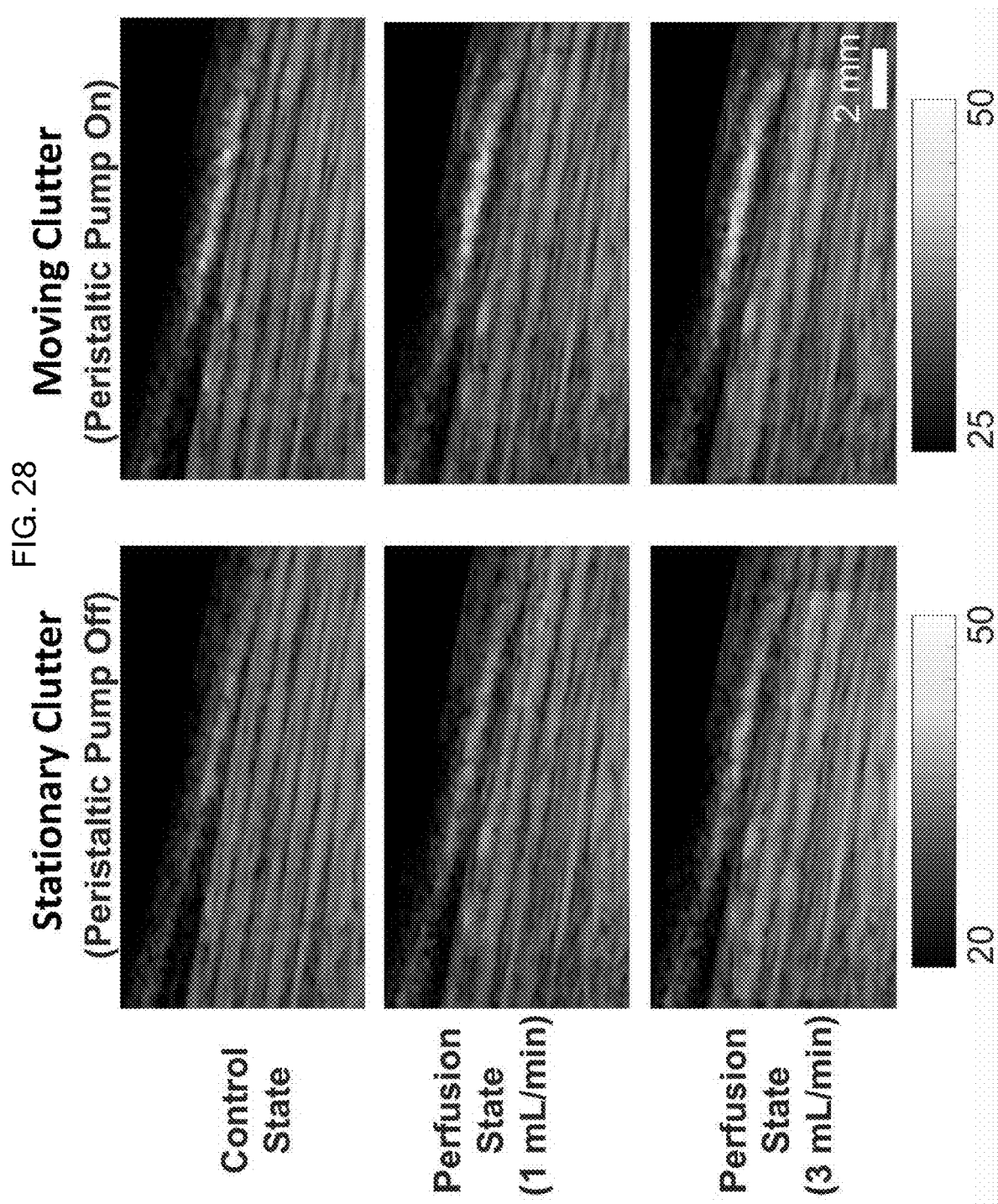
FIG. 28. PD images of Phantom I with stationary (left) and moving (right) clutter for three flow states. The view is magnified 2× compared with CF images in FIG. 27.

PD images in FIG. 28 illustrate additional properties of our approach to slow-flow imaging. First, the method can be effective at showing qualitatively the staged increase in echo power with increased flow. The top row of images are a control state with stationary water in the fibers. The second and third rows include flowing TM blood in the fibers. No flow is appropriately indicated in the control for stationary clutter. However, flow is indicated in the most proximal single fiber of the control state where echo strength and clutter motion are both large. These physical features significantly expand the clutter eigenbandwidth of the echo signal into the blood subspace for that fiber. Although we adjusted filter parameters as shown in Table 6, suppressing additional spatial and frametime eigenvectors would inappropriately reduce the indication of true flow at 1 and 3 mL/min found in rows 2 and 3 of FIG. 28. This may be a particularly challenging filtering task that nicely illustrates conditions where the clutter eigenbandwidth expands to overlap the blood subspace. Similar results are found at 5 MHz (not shown) except the fibers are not resolved. Our inability to separate the clutter and blood subspaces at 5 MHz and 12.5 MHz are shown in FIG. 29. The power of postfiltered signal increases linearly with flow rate. However, the estimated power was significantly biased high with the existence of moving clutter.

D. Clutter Filter Thresholds

Statistical methods for selecting SVD clutter-filter thresholds can be used for decompositions that involve Casorati matrices in 2D (adaptive spatiotemporal) and 3D (the GM-MDL classifier). However, threshold values reported in Table 6 were found using a method based on visual inspection of eigenvectors, which we now describe.

1) Slow time: Slow-time eigenvectors $U=(u_1, \ldots, u_N)$ offer little information about separating clutter and perfusing blood subspaces. The first 3-5 slow-time eigenvectors are included and averaged while the others are discarded to reject noise. U does not help with clutter rejection.

2) Spatial: Spatial eigenvectors $V=(v_1, \ldots, v_s, \ldots, v_S)$ are very informative about subspace parsing once they are reordered into "eigenimages." Reshaping each eigenvector $v_s$ into an M×L image v[m, l], we find that those in the clutter subspace bear a resemblance to the B-mode image, while those in blood and noise-dominated subspaces describe those spatial modes to the extent a subspaces is dominated by a single physical source.

Figure 30:
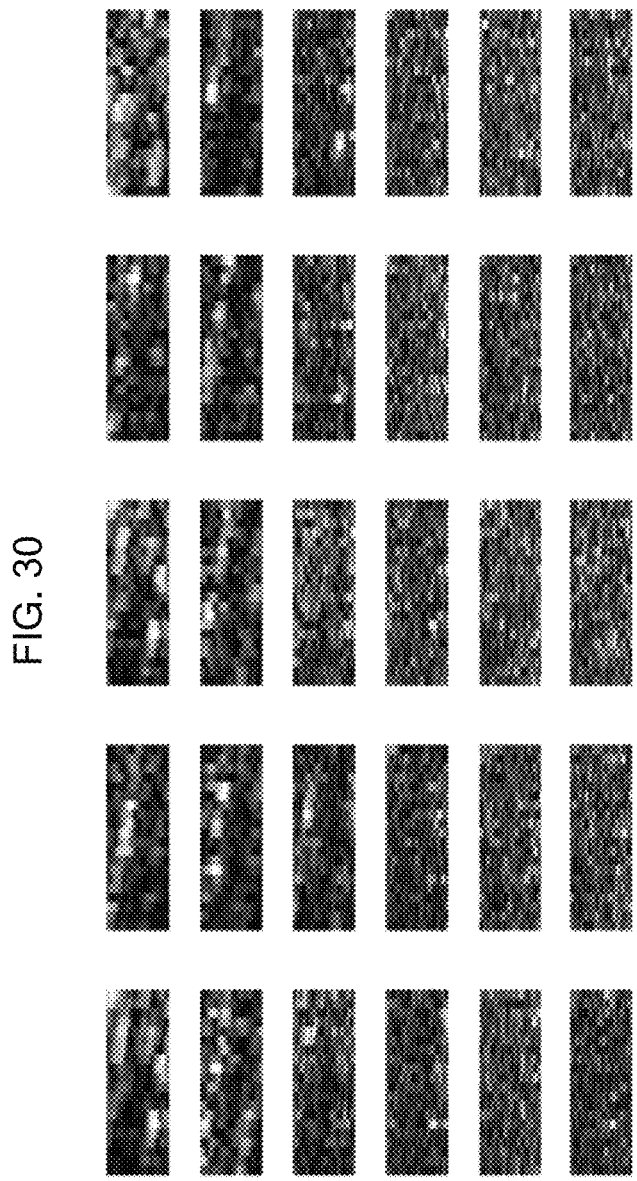
FIG. 30. Eigenimages corresponding to the largest 30 spatial eigenvalues for phantom I at $f_0$=5 MHz and 2 mL/min flow rate.

The first 30 eigenimages from a phantom I experiment with directional fibers and stationary clutter are shown in FIG. 30. Notice how eigenimages 1-10 show a diagonal linear pattern similar to that of stationary clutter as seen in FIGS. 27 and 28, while 21-30 have the appearance of spatial white noise. The blood subspace lies between the clutter and noise spatial subspaces but they are not distinct, in part, because clutter and flow movements are along the fibers. The first 30 eigenimages of phantom I with moving (water pulses along fibers) or stationary clutter look very similar.

The eigenimage patterns for phantom II, where fibers are not spatially aligned, are quite different as seen in FIG. 31. We display the first 50 eigenimages under four conditions including flow rates of 0 and 5 mL/min and with stationary and moving clutter. Recall the moving clutter in phantom II was a spoon tapping one location on the plastic phantom exterior.

For no flow and stationary clutter (upper left images of FIG. 31), we selected the first five eigenimages as the clutter subspace. These eigenvectors correspond to the five largest singular values along the spatial axis of the 3-D core matrix. The linear patterns of phantom I in the clutter subspace of FIG. 30 are gone from these first five eigenimages of FIG. 31 because flow fibers are not aligned in phantom II. The next six eigenimages appear dark but have bright pixels in their upper left corner; these were selected as the blood subspace. The remainder were deemed noise. Adding moving clutter but no flow to phantom II (upper right images), the clutter and blood subspaces are each extended as movement increases the eigenbandwidth for these components of the Doppler spectrum. Consider that even without 'flow,' clutter movements cause the TM blood within fibers to move.

Similar eigenimage patterns are seen when flow increases to 5 mL/min (lower two image blocks in FIG. 31), except that the motions related to clutter or flow act to increase the extent of each of those subspaces. While the selection of the exact blood subspace may seem arbitrary from this example, our choices are based on trends observed from many phantom experiments. The clearer separability between the three component subspaces in phantom II compared to phantom I is partially due to the more distinct spatial movements between clutter and flow in phantom II. There spatially coherent waves from a clutter point source are distinct from spatially incoherent flow within tangled fibers.

A second distinguishing feature, which is less obvious, may be related to the bright few pixels near the upper left corner in most of the clutter and blood subspaces that do not appear reliably in noise eigenimages. The bright focal pattern identifies a point source of motion (tapping spoon) appearing only in eigenimages within clutter and blood subspace that comprise the echo-signal bandwidth.

Once the blood subspace is identified, the core tensor can be filtered along the spatial eigenvalue axis by zeroing eigenvalues outside the blood subspaces, as indicated in FIG. 31, before resynthesizing the echo signal via Equation (46).

Figure 32:
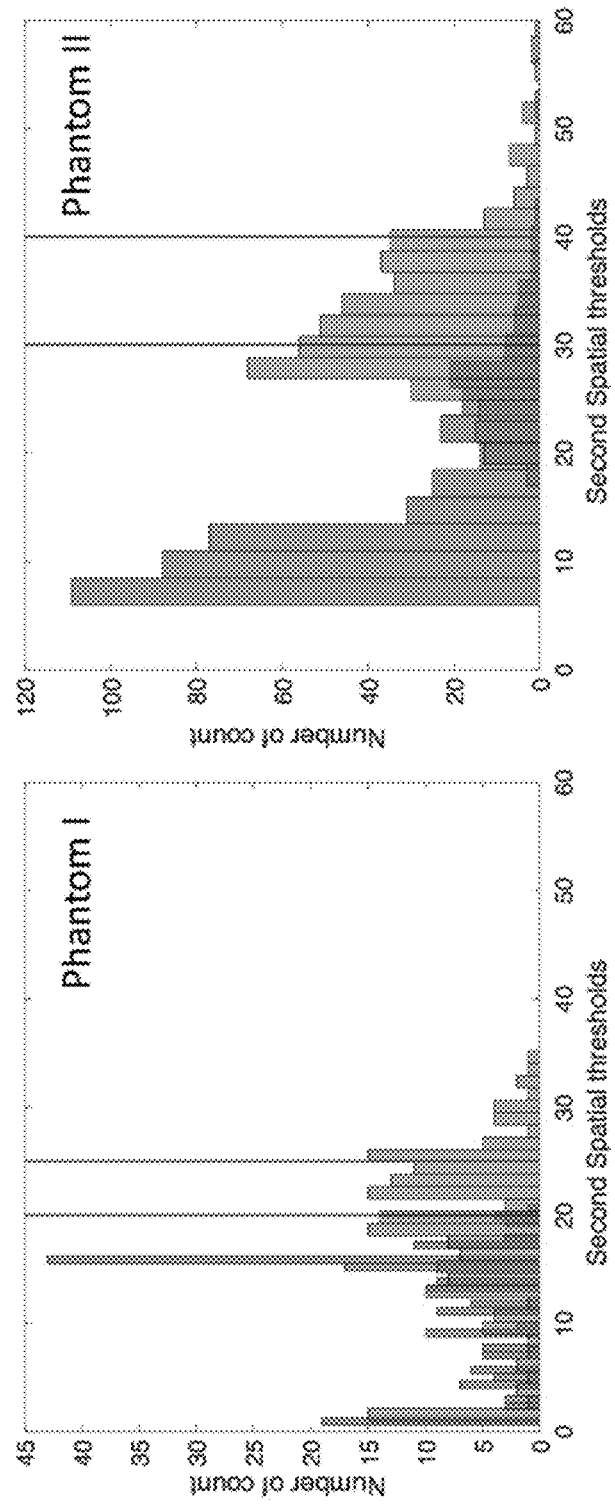
FIG. 32. Left and right plots are histograms of the spatial thresholds set for echo-signal filtering using phantoms I and II, respectively. The horizontal axis is the spatial threshold value at the blood-noise boundary while the vertical axis is the number of spatial segments at that threshold. Blue and orange bins indicate the thresholds set for stationary and moving clutter, respectively, using the GM-MDL statistical classifier, which varies thresholds at every subregion where a clutter filter is computed in an image field. The blue and red vertical lines indicate the fixed visual upper thresholds for the spatial-dimension with stationary and moving clutter, respectively.

3) Comparison of filter threshold parameters I: FIG. 32 compares the fixed upper-filter thresholds (two vertical lines) with histograms of upper thresholds determined by the GMMDL statistical classifier. This is the boundary along the spatial eigenvector axis that separates blood and noise-dominated subspaces. Note that the MDL component of the filter classifies a blood-noise boundary for every eigenvector independently. So, we define a histograms of 'threshold values' for the many spatial subregion in a PD or CF image in FIG. 32. Histograms show a clearer discrimination of blood flow from noise in phantom II where flow is spatially disorganized. We expected the spatially directed flow in phantom I would better separate flow from white noise based only on the spatial characteristics of these two sources. It seems, however, that clutter motion emerging from a focal point in phantom II provides unique spatial-mode features that helps separate blood and noise subspaces. This strong clutter component leaks into the blood subspace but not the noise subspace and that aids both clutter and noise rejection.

These histogram values can be compared with two vertical lines that are the fixed threshold based on the appearance of eigenimages. Clearly the fixed threshold aligns with the statistical classifier as expected since both are based on eigenstate features of the echo data.

4) Frame time: The frame-time eigenvector matrix $W=(w_1, \ldots, w_k, \ldots, w_K)$ can provide additional information for parsing subspaces. These temporal characteristics are best revealed in the frequency/velocity-axis domain. Specifically, we find the frequency spectrum for each column in W, i.e., $|\mathcal{F}\{w_k\}|$, convert the frequency axis to velocity, and map results into an image of frame-time eigenspectra as displayed in the first two columns of FIG. 10. Eigenspectra illustrate the relationship between the frame-time eigenindex and the Doppler frequency axis.

For phantom I scanned at 12.5 MHz with stationary clutter, we excluded the first two frame-time eigenvectors in the filter bandpass as the clutter subspace. This is indicated by the leftmost dotted line in each eigenspectra. Stationary clutter occupies a very narrowband subspace along the frame-time axis. When there is no flow, the eigenspectra (top two rows) appear as white noise except in the clutter subspace. As flow increases beyond 1 mL/min toward (or away from) the transducer, we find a linear pattern in the eigenspectra along positive (negative) frequencies until aliasing occurs near eigenindex 20 (the rightmost dotted lines). The dotted lines bound the eigenbandpass for the frame-time axis. As flow increases further, aliased echo power enters this eigenbandpass.

Figure 33:
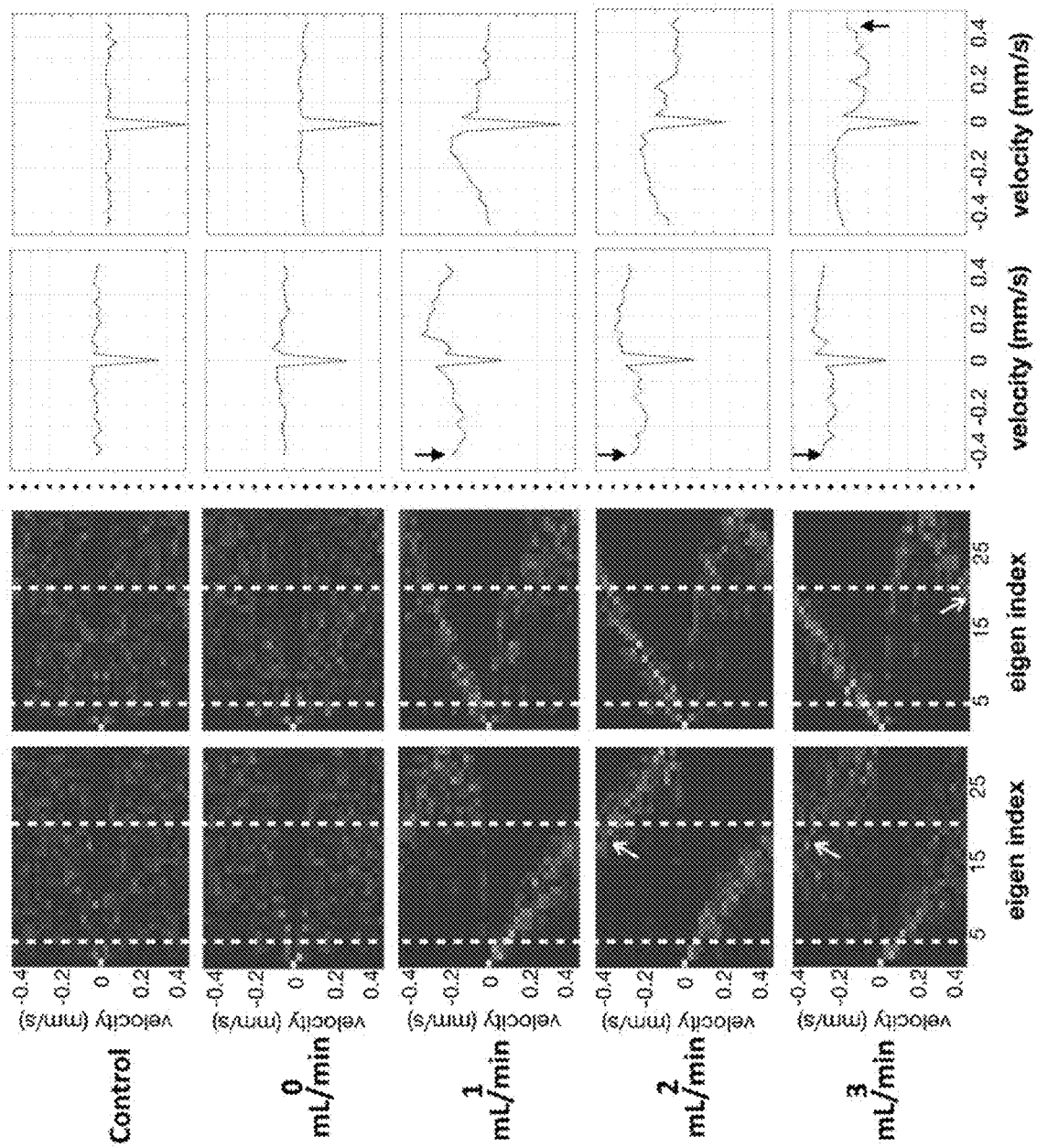
FIG. 33. These data are acquired at 12.5 MHz with phantom I and stationary clutter. The leftmost two columns are pre-filtered frame-time eigenspectral found by computing the frequency spectrum of each column of matrix W (horizontal axis labeled eigen index) and converting the frequency axis to velocity (vertical axis). Spectral power along positive velocities (first column) specifies flow toward the transducer; that along negative velocities indicates flow away from the transducer (second column). The rightmost two columns are post-filtered Doppler spectra [dB] found by summing prefiltered eigenspectra on the left between the dotted white lines. The third column corresponds to the first column and the fourth to the second. Arrows on eigenspectra indicate the wraparound points for aliasing, while those in Doppler spectra show the associated boost in high-frequency power.

Summing the eigenspectra along the velocity axis and between the two filter thresholds, we obtain the Doppler spectra [amplitude converted to dB] on the right hand side of FIG. 33. Its centroid from Equation (49) is our estimate of velocity. Doppler spectra exhibit low spectral values near zero velocity because the filter eliminates the first two eigenvectors.

When moving clutter is present, the first six eigenvectors are excluded at 12.5 MHz (Table 6). Frame-time filter settings aim to exclude non-blood-flow signal power, but they also serve to avoid aliasing for the CF imaging option. However, in PD images, the high-index filter threshold is increased to capture aliased blood-flow power provided the eigenvalues exceed values found in the noise-only subspace.

E. Comparison of Filter Threshold Parameters II

Figure 34:
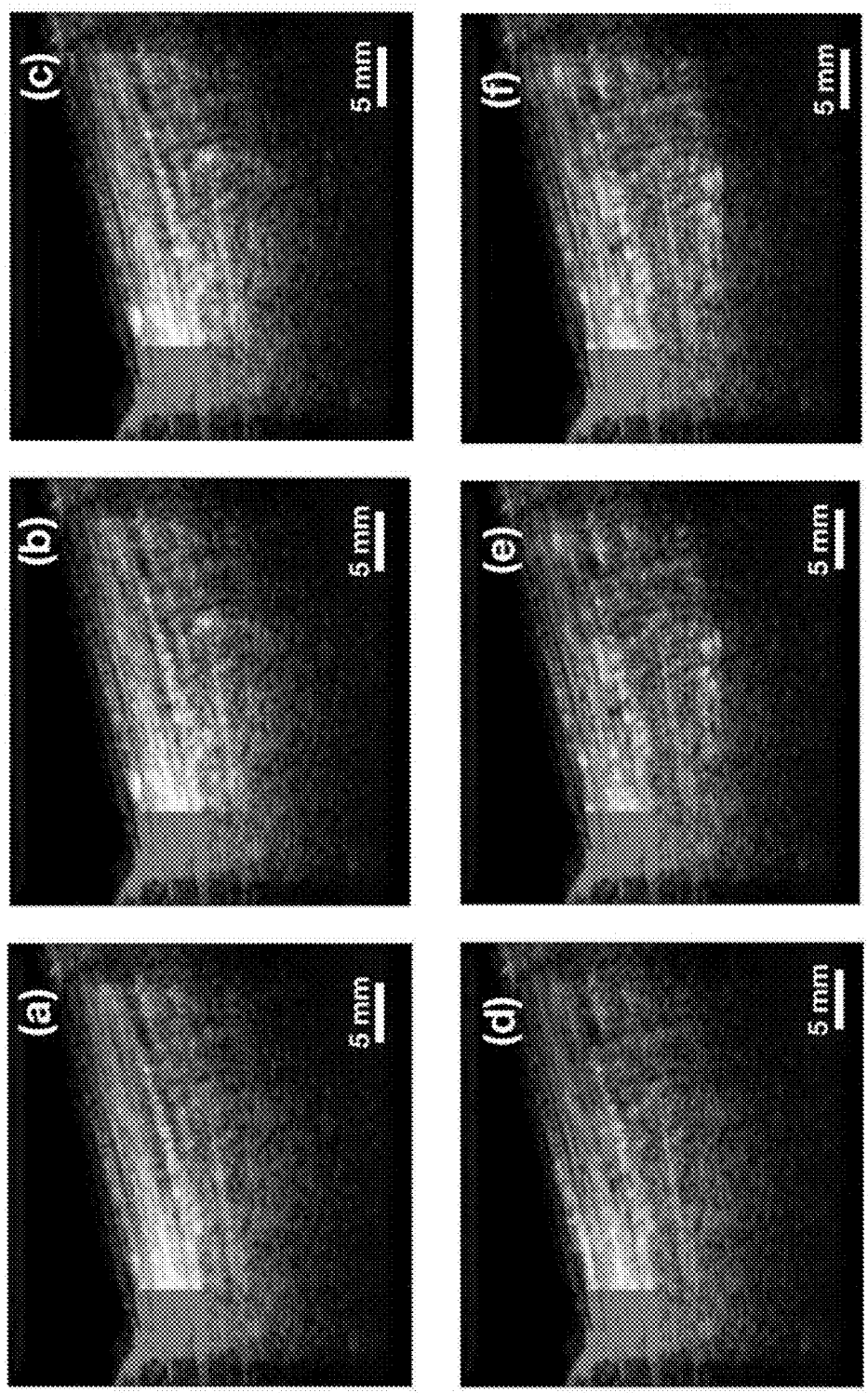
FIG. 34. First and second rows are 5 MHz PD images of phantom I at a 3 mL/min flow rate with stationary and moving clutter, respectively. a) and d) are processed with the fixed thresholds listed in Table 6. b) and e) are processed with the adaptive spatiotemporal auto-thresholding method. c) and f) are processed using the GM classifier clutter filter with MDL noise filtering.

PD phantom images found by applying our fixed visual thresholding method described above are compared to those of the adaptive spatiotemporal method and the GM-MDL statistical classifier in FIG. 34. These results show that fixed visual thresholding tends to be more conservative; i.e., more aggressive at clutter rejection than the others. However, this is only an observed trend given the limited data available. The principal advantage of the visual thresholding method can be to provide an operator with filter parameter settings based on eigenvector features that align with our knowledge of the physics of echo formation.

F. Velocity Discrimination from PD Estimates

Figure 35:
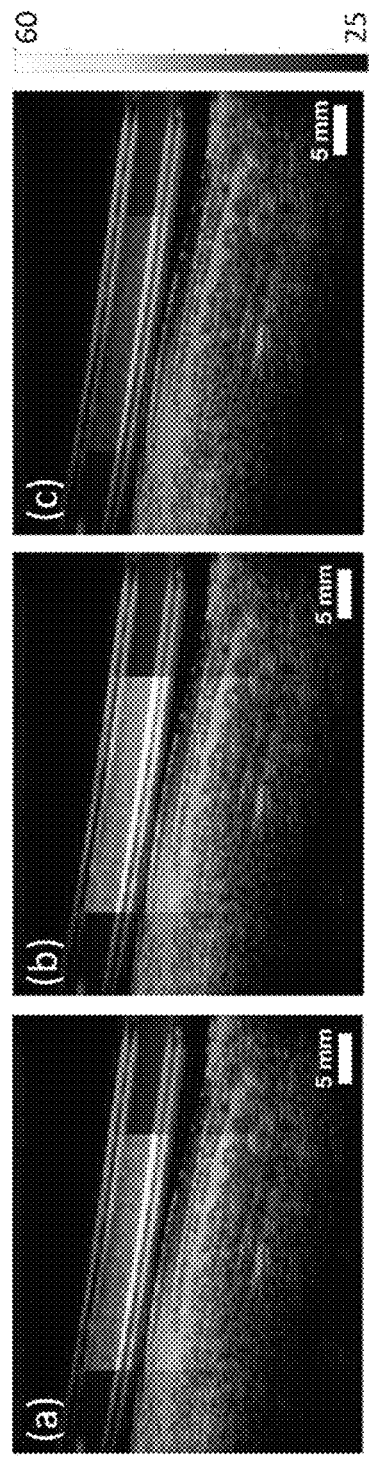
FIG. 35. Three 5 MHz PD images with velocity discrimination are shown for phantom I where an 8-mm flow tube was added proximal to the flow fibers. In both structures we introduce TM blood at a rate of 4 mL/min using separate sources. Fluid speed in the tube is expected to be higher than in the fibers because of differences in resistance to flow. Images display axial flow speed ranges from (a) 0.0-0.6 mm/s, (b) 0.6-1.3 mm/s, and (c) 1.6-2.0 mm/s. Power is measured in dB.

In most in vivo perfusion imaging situations, the Doppler angle is poorly defined making accurate angle correction impossible and hence velocity accuracy unreliable. Thus, there are situations where it would be helpful to partition signal power from PD images into velocity ranges. Aspects of this invention provide methods for rendering PD images according to velocity ranges along the slow-time axis. We now apply the same technique along the frame-time axis using eigenspectra. The experimental results are given in FIG. 35.

We added an 8-mm-diameter flow tube alongside the cellulose fibers in Phantom I. Each is attached to its own syringe pump, and both are set to 4 mL/min. With the low flow resistance in the 8 mm tube we expect to measure a higher TM blood speed than in the cellulose fibers. We measured a mean axial flow speed inside the rubber tube of 1.2 mm/s and inside the cellulose fibers of 0.4 mm/s. None of the measurements are corrected for Doppler angle as we assume θ is unknown. We see that the low resistance of the tube generates the greatest PD amplitude and the largest velocity.

FIG. 36 illustrates the velocity discrimination processing along the frame-time axis for slow-time discrimination. Other elements of clutter filter are unchanged. We apply a lower clutter bound at eigenindex 3 and an upper anti-aliasing bound at eigenindex 25. Furthermore, we bound the frequency-axis range between the three frequency ranges described in FIG. 35, which is indicated by $\pm(\upsilon_{min}, \upsilon_{max})$. We then synthesize the echo signal using Equation (46) and compute signal power via Equation (47).

All publications, patents and literature specifically mentioned herein are incorporated by reference for all purposes.

While the present invention may be susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims herein for interpreting the scope of the invention.

The system and methods are described with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the system and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

What is claimed is:

1. A method for imaging flow of a fluid in an object of interest, the method comprising:
    acquiring beamformed ultrasound echo data from the object of interest comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension;
    re-ordering the spatiotemporal data array into a three-dimensional perfusion data array having one combined spatial dimension, one slow-time dimension, and one frame-time dimension, wherein the axial and lateral dimensions are combined into the one combined spatial dimension;
    filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and
    forming an ultrasound image of the object of interest from the filtered perfusion data array.

2. The method of claim 1, wherein the fluid is blood and the method is performed without the use of a contrast agent.

3. The method of claim 1, wherein the echo data is acquired upon transmitting a focused ultrasound beam into the object of interest.

4. The method of claim 1, wherein filtering the perfusion data array with an eigen passband clutter filter comprises the steps:
unfolding the perfusion data array into three empirical correlation matrices based on slow-time signals, spatial signals, and frame-time signals;
calculating eigenvectors for each of the three empirical correlation matrices of the perfusion data array, wherein the eigenvectors are columns of a core tensor; and
selecting a subspace within the core tensor that contains signals from the slowly moving and/or spatially disorganized fluid in the object of interest and zeroing the rest of the core tensor.

5. The method of claim 4, wherein the clutter filter partitions an echo data subspace of spatially coherent tissue movements from an echo data subspace of spatially incoherent fluid perfusion.

6. The method of claim 4, wherein the filtering enhances the sensitivity of imaging perfusion of the fluid within the object of interest by identifying a subspace in the perfusion array data that isolates perfusion signals and by projecting the echo data onto the subspace before computing the image of the object of interest.

7. The method of claim 4, wherein selecting a subspace within the core tensor that contains signals from the slowly moving and/or spatially disorganized fluid in the object of interest comprises visually selecting an eigenvector passband according to the steps:
a) eliminating one or more initial spatial eigenvectors having a uniform spatial signal spectrum, which are dominated by clutter;
b) selecting a passband range of slow-time signal eigenvectors, wherein the passband range begins after initial eigenvectors having non-zero signals only at zero frequency, and wherein the passband range ends before a linear slow-time spectral pattern appears in a spectral region of the slow-time eigenvectors of a comparative control sample;
c) selecting a passband range of frame-time signal eigenvectors, wherein the passband range spans an asymmetric linear frame-time spectral pattern in the object of interest.

8. The method of claim 4, wherein selecting a subspace within the core tensor that contains signals from the slowly moving and/or spatially disorganized fluid in the object of interest comprises using a classifier which identifies and eliminates core elements of the core tensor that are predominantly from a clutter source based on energy and similarity features according to the following steps performed on comparative training data similar to the echo data of the object of interest:
a) calculating normalized eigenvalue energy of the slow-time, spatial, and frame-time dimensions and discarding a high eigenvalue energy region;
b) calculating a Pearson's correlation coefficient to quantify similarity of spatial images from spatial eigenvectors of the slow-time dimension and discarding a high similarity region;
c) calculating a coherent motion corruption scalar factor from the frame-time dimension echo power images and discarding a corrupt region;
d) classifying and eliminating core elements above a classifier threshold as being clutter dominated, wherein the classifier threshold is calculated from a combination of steps a), b), and c) using the comparative training data.

9. The method of claim 4, wherein selecting a subspace within the core tensor that contains signals from the slowly moving and/or spatially disorganized fluid in the object of interest comprises visually selecting core tensor eigenimages of the perfusion data array according to the steps:
a) averaging slow-time spatial eigenimages 3-5 and discarding others;
b) retaining a series of fluid flow spatial eigenimages which appear visibly dark and appear after initial eigenimages that are bright, and discarding noise eigenimages beyond the fluid flow spatial eigenimages; and
c) discarding the first two frame-time eigenimages and discarding frame-time eigenimages having the appearance of aliasing.

10. The method of claim 4, further comprising the step of noise filtering after clutter filtering, wherein noise filtering is performed by discarding noise dominated subspace of the core tensor.

11. The method of claim 1, wherein the echo data is acquired by Doppler mode, the imaging is color-flow or power-Doppler imaging, and wherein the frame-time dimension is sampled at a rate about 100 to 1,000 times slower than the slow-time dimension.

12. The method of claim 1, wherein the echo data is acquired over a period up to about 10 seconds, or up to about 30 seconds.

13. The method of claim 1, wherein the echo data is obtained from transducer ultrasound pulses having from 3 to 32 MHz center frequency.

14. The method of claim 13, wherein the ultrasound pulses have at least 5 mm tissue penetration.

15. The method of claim 4, wherein forming an image of the object of interest comprises the steps:
calculating the signal power of the subspace of spatially incoherent fluid perfusion; and
mapping the signal power into the image of the object of interest.

16. The method of claim 1, further comprising fluid velocity discrimination, wherein velocity is calculated from a post-filtered slow-time echo signal.

17. The method of claim 1, wherein the object of interest is a tissue, a blood vessel, a microvascular structure, a vascular network, an organ, an appendage, or a tumor.

18. The method of claim 1, wherein the imaging shows peripheral muscle blood perfusion to assess microvascular damage from ischemia or chronic metabolic disorders.

19. An apparatus for ultrasound imaging, comprising:
an ultrasound probe for transmitting ultrasound pulses and receiving ultrasound echo signals and transferring ultrasound echo signals to a processor;
a processor for carrying out the steps:
acquiring beamformed ultrasound echo data from the ultrasound probe, the data comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension;
re-ordering the spatiotemporal data array into a three-dimensional perfusion data array having one combined spatial dimension, one slow-time dimension, and one frame-time dimension, wherein the axial and lateral dimensions are combined into the one combined spatial dimension;

filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array; and a display for displaying the ultrasound image.

20. The apparatus of claim 19, wherein the fluid is blood, the echo data is acquired by Doppler mode, the imaging is color-flow or power-Doppler imaging, and the object of interest is a tissue, a blood vessel, a microvascular structure, a vascular network, an organ, an appendage, or a tumor.

21. The apparatus of claim 19, wherein the transmitted ultrasound pulses are formed into a focused beam.

22. The apparatus of claim 19, wherein the frame-time dimension has a sampling rate about 100 times slower than a sampling rate of the slow-time dimension.

23. The apparatus of claim 19, wherein the probe comprises a transducer for RF pulses having from 3 to 32 MHz center frequency.

24. The apparatus of claim 19, wherein filtering the perfusion data array with an eigen passband clutter filter comprises the steps:

unfolding the perfusion data array into three empirical correlation matrices based on slow-time signals, spatial signals, and frame-time signals;

calculating eigenvectors for each of the three empirical correlation matrices of the perfusion data array, wherein the eigenvectors are columns of a core tensor; and selecting a subspace within the core tensor that contains signals from the slowly moving and/or spatially disorganized fluid in the object of interest and zeroing the rest of the core tensor.

25. The apparatus of claim 24, wherein selecting a subspace within the core tensor that contains signals from the slowly moving and/or spatially disorganized fluid in the object of interest comprises using a classifier which identifies and eliminates core elements of the core tensor that are predominantly from a clutter source based on energy and similarity features according to the following steps performed using comparative training data similar to the echo data from object of interest:

a) calculating normalized eigenvalue energy of the slow-time, spatial, and frame-time dimensions and discarding a high eigenvalue energy region;

b) calculating a Pearson's correlation coefficient to quantify similarity of spatial images from spatial eigenvectors of the slow-time dimension and discarding a high similarity region;

c) calculating a coherent motion corruption scalar factor from the frame-time dimension echo power images and discarding a corrupt region;

d) classifying and eliminating core elements above a classifier threshold as being clutter dominated, wherein the classifier threshold is calculated from a combination of steps a), b), and c) using the comparative training data.

26. The apparatus of claim 19, further comprising the processor executing noise filtering after clutter filtering, wherein noise filtering is performed by discarding noise dominated subspace of the core tensor.

27. A non-transitory machine-readable storage medium having stored therein instructions for execution by a processor which cause the processor to perform the steps of a method for imaging an object of interest containing a fluid, the method comprising:

acquiring beamformed ultrasound echo data comprising a spatiotemporal data array, wherein the spatiotemporal data array comprises two-dimensional spatial data comprising axial and lateral dimensions, a third dimension comprising a temporal slow-time dimension, and a fourth dimension comprising a temporal frame-time dimension;

re-ordering the spatiotemporal data array into a three-dimensional perfusion data array having one combined spatial dimension, one slow-time dimension, and one frame-time dimension, wherein the axial and lateral dimensions are combined into the one combined spatial dimension;

filtering the perfusion data array with an eigen passband clutter filter, wherein the clutter filter preserves the three dimensions of the perfusion data array, and wherein the clutter filter isolates echo data power from slowly moving and/or spatially disorganized fluid in the object of interest and suppresses clutter power; and forming an ultrasound image of the object of interest from the filtered perfusion data array.

28. The storage medium of claim 27, wherein filtering the perfusion data array with an eigen passband clutter filter comprises the steps:

unfolding the perfusion data array into three empirical correlation matrices based on slow-time signals, spatial signals, and frame-time signals;

calculating eigenvectors for each of the three empirical correlation matrices of the perfusion data array, wherein the eigenvectors are columns of a core tensor; and selecting a subspace within the core tensor that contains signals from the slowly moving and/or spatially disorganized fluid in the object of interest and zeroing the rest of the core tensor.

29. The storage medium of claim 28, wherein selecting a subspace within the core tensor that contains signals from the slowly moving and/or spatially disorganized fluid in the object of interest comprises using a classifier which identifies and eliminates core elements of the core tensor that are predominantly from a clutter source based on energy and similarity features according to the following steps performed on comparative training data similar to the object of interest:

a) calculating normalized eigenvalue energy of the slow-time, spatial, and frame-time dimensions and discarding a high eigenvalue energy region;

b) calculating a Pearson's correlation coefficient to quantify similarity of spatial images from spatial eigenvectors of the slow-time dimension and discarding a high similarity region;

c) calculating a coherent motion corruption scalar factor from the frame-time dimension echo power images and discarding a corrupt region;

d) classifying and eliminating core elements above a classifier threshold as being clutter dominated, wherein the classifier threshold is calculated from a combination of steps a), b), and c) using the comparative training data.

* * * * *